Figure 1:
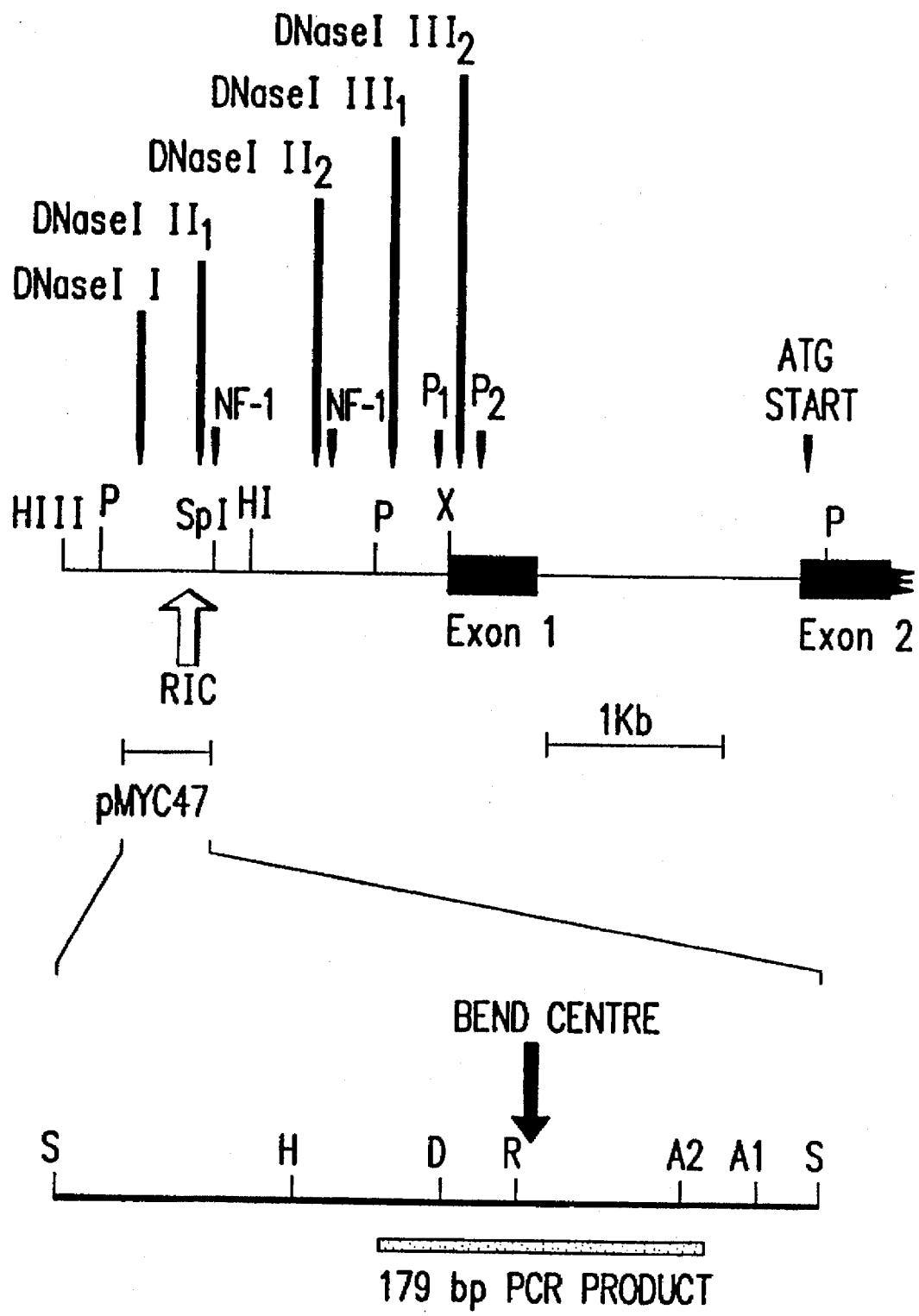

United States Patent [19]
Johnson et al.

[11] Patent Number: 5,672,479
[45] Date of Patent: Sep. 30, 1997

[54] METHODS FOR IDENTIFYING COMPOUNDS THAT BIND TO PUR PROTEIN

[75] Inventors: Edward M. Johnson, New York, N.Y.; Andrew D. Bergemann, Boston, Mass.

[73] Assignee: Mount Sinai School of Medicine, New York, N.Y.

[21] Appl. No.: 486,421

[22] Filed: Jun. 7, 1995

Related U.S. Application Data

[60] Division of Ser. No. 470,911, Jun. 6, 1995, which is a continuation-in-part of Ser. No. 14,943, Feb. 2, 1993, Pat. No. 5,545,551, which is a continuation-in-part of Ser. No. 938,189, Aug. 28, 1992.

[51] Int. Cl.$^6$ .................. G01N 33/53; G01N 33/574; C07K 2/00; C12N 15/00
[52] U.S. Cl. .................. 435/7.1; 435/7.23; 435/7.71; 435/7.93; 530/300; 530/358; 935/39; 935/41
[58] Field of Search .................. 435/7.1, 7.23, 435/7.71, 7.93; 530/300, 358; 935/39, 41

[56] References Cited

PUBLICATIONS

Wobbe et al., 1987, "Replication of Simian Virus 40 Origin-containing DNA in vitro With Purified Protein" Proc. Natl. Acad. Sci. USA 84:1834–1838.

Traut, W. and Fanning, E., 1988, "Sequence Specific Interactions Between a Cellular DNA-binding Protein and the Simian Virus 40 Origin of DNA Replication" Mol. Cell. Biol. 8:903–911.

Vassilev, L. and Johnson, E.M. 1989, "Mapping Initiation Sites of DNA Replication in vivo Using Polymerase Chain Reaction Amplification of Nascent Strand Segments" Nucl. Acids Res. 17:7693–7705.

Caddle, M.S. et al., 1990, "Intramolecular DNA Triplexes, Bent DNA and DNA Unwinding Elements in the Initiation Region of an Amplified Dihydrofolate Reductase Replicon" J. Mol. Biol. 211:19–33.

Vassilev, L. and Johnson, E.M., 1990, "An Initiation Zone of Chromosomal DNA Replication Located Upstream of the c–myc Gene in Proliferating HeLa Cells" Mol. Cell. Biol. 10:4899–4904.

Dailey, L. et al., 1990, "Purification of RIP60 and RIP100, Mammalian Proteins with Origin Specific DNA–binding and ATP–Dependent DNA Helicase Activity" Mol. Cell. Biol. 10:6225–6235.

Caddle, M.S. et al., 1990, "RIP60, a Mammalian Origin–Binding Protein, Enhances DNA Bending Near the Dihydrofolate Reductase Origin of Replication" Mol. Cell. Biol. 10:6236–6243.

Hofmann, J. F.–X. and Gasser, S.M., 1991, "Identification and Purification of a Protein that Binds the Yeast ARS Consensus Sequence" Cell 64:951–960.

Gutierrez et al., 1991, "Mechanism of Stimulation of DNA Replication by Bacteriophage $\phi$29 Single–Standed DNA–binding Protein p5" J. Biol. Chem., 266:2104–2111.

Erdile et al., 1991, "Characterization of a cDNA Encoding the 70–kDa Single–stranded DNA–binding Subunit of Human Replication Protein A and the Role of the Protein in DNA Replication" J. Biol. Chem., 266:12090–12098.

Bergemann, A.D. and Johnson, E.M., 1992, "The HeLa PUR Factor Binds Single–Stranded DNA at a Specific Element Conserved in Gene Flanking Regions and Origins of DNA Replication" Mol. Cell. Biol. 12:1257–1265.

Bergemann, A.D. and Johnson, E.M., 1992, "Sequence of cDNA Comprising the Human pur Gene and Sequence–Specific–Single–Stranded–DNA–Binding Properties of the Encoded Protein" Mol. Cell. Biol. 12:5673–5682.

Primary Examiner—Mindy Fleisher
Assistant Examiner—Bonnie D. Weiss
Attorney, Agent, or Firm—Pennie & Edmonds

[57] ABSTRACT

The present invention relates to the PUR protein, nucleotide sequences and expression vectors encoding PUR, and to methods for inhibiting PUR activity. Inhibitors of PUR activity may be used to treat hyperproliferative diseases such as cancer.

12 Claims, 28 Drawing Sheets

562 TACTATATTC ACTTAACACT TGAACGCTGA GCTGCAAACT -1724
602 CAACGGGTAA TAACCCATCT TGAACAGCGT ACATGCTATA -1684
642 CACACACCCC TTTCCCCCGA ATTGTTTTCT CTTTTGGAGG -1644
682 TGGTGGAGGG AGAGAAAAGT TTACTTAAAA TGCCTTTGGG -1604
722 TGAGGGACCA AGGATGAGAA GAATGTTTTT TGTTTTTCAT -1564
762 GCCGTGGAAT AACACAAAAT AAAAAATCCC GAGGGAATAT -1524
802 ACATTATATA TTAAATATAG ATCATTTCAG -1494

FIG.8

```
-59  CGACTGAGGCGGCGGGCGGAGCGGCAGGCGGCGGCGGCCGCGGCAGCGGAGCGCAGCATC

1  ATG GCG GAC CGA GAC AGC GGC AGC GAG CAG GGT GGT GCG GCG CTG
     Met Ala Asp Arg Asp Ser Gly Ser Glu Gln Gly Gly Ala Ala Leu

46  GGT TCG GGC GGC TCC CTG GGG CAC CCC GGC TCG GGC TCA GGC TCC
     Gly Ser Gly Gly Ser Leu Gly His Pro Gly Ser Gly Ser Gly Ser

91  GGC GGG GGC GGT GGT GGC GGC GGG GGC GGC GGC GGC AGT GGC GGC
     Gly Gly Gly Gly Gly Gly Gly Gly Gly Gly Gly Gly Ser Gly Gly

136  GGC GGC GGC GGG GCC CCA GGG GGG CTG CAG CAC GAG ACG CAG GAG
     Gly Gly Gly Gly Ala Pro Gly Gly Leu Gln His Glu Thr Gln Glu

181  CTG GCC TCC AAG CGG GTG GAC ATC CAG AAC AAG CGC TTC TAC CTG
     Leu Ala Ser Lys Arg Val Asp Ile Gln Asn Lys Arg Phe Tyr Leu

226  GAC GTG AAG CAG AAC GCC AAG GGC CGC TTC CTG AAG ATC GCC GAG
     Asp Val Lys Gln Asn Ala Lys Gly Arg Phe Leu Lys Ile Ala Glu

271  GTG GGC GCG GGC GGC AAC AAG AGC CGC CTT ACT CTC TCC ATG TCA
     Val Gly Ala Gly Gly Asn Lys Ser Arg Leu Thr Leu Ser Met Ser

316  GTG GCC GTG GAG TTC CGC GAC TAC CTG GGC GAC TTC ATC GAG CAC
     Val Ala Val Glu Phe Arg Asp Tyr Leu Gly Asp Phe Ile Glu His

361  TAC GCG CAG CTG GGC CCC AGC CAG CCG CCG GAC CTG GCC CAG GCG
     Tyr Ala Gln Leu Gly Pro Ser Gln Pro Pro Asp Leu Ala Gln Ala

406  CAG GAC GAG CCG CGC CGG GCG CTC AAA AGC GAG TTC CTG GTG CGC
     Gln Asp Glu Pro Arg Arg Ala Leu Lys Ser Glu Phe Leu Val Arg

451  GAG AAC CGC AAG TAC TAC ATG GAT CTC AAG GAG AAC CAG CGC GGC
     Glu Asn Arg Lys Tyr Tyr Met Asp Leu Lys Glu Asn Gln Arg Gly

496  CGC TTC CTG CGC ATC CGC CAG ACG GTC AAC CGG GGG CCT GGC CTG
     Arg Phe Leu Arg Ile Arg Gln Thr Val Asn Arg Gly Pro Gly Leu
```

FIG.10A

```
541  GGC TCC ACG CAG GGC CAG ACC ATT GCG CTG CCC GCG CAG GGG CTC
     Gly Ser Thr Gln Gly Gln Thr Ile Ala Leu Pro Ala Gln Gly Leu

586  ATC GAG TTC CGT GAC GCT CTG GCC AAG CTC ATC GAC GAC TAC GGA
     Ile Glu Phe Arg Asp Ala Leu Ala Lys Leu Ile Asp Asp Tyr Gly

631  GTG GAG GAG GAG CCG GCC GAG CTG CCC GAG GGC ACC TCC TTG ACT
     Val Glu Glu Glu Pro Ala Glu Leu Pro Glu Gly Thr Ser Leu Thr

676  GTG GAC AAC AAG CGC TTC TTC TTC GAT GTG GGC TCC AAC AAG TAC
     Val Asp Asn Lys Arg Phe Phe Phe Asp Val Gly Ser Asn Lys Tyr

721  GGC GTG TTT ATG CGA GTG AGC GAG GTG AAG CCC ACC TAT CGC AAC
     Gly Val Phe Met Arg Val Ser Glu Val Lys Pro Thr Tyr Arg Asn

766  TCC ATC ACC GTC CCC TAC AAG GTG TGG GCC AAG TTC GGA CAC ACC
     Ser Ile Thr Val Pro Tyr Lys Val Trp Ala Lys Phe Gly His Thr

811  TTC TGC AAG TAC TCG GAG GAG ATG AAG AAG ATT CAA GAG AAG CAG
     Phe Cys Lys Tyr Ser Glu Glu Met Lys Lys Ile Gln Glu Lys Gln

856  AGG GAG AAG CGG GCT GCC TGT GAG CAG CTT CAC CAG CAG CAA CAG
     Arg Glu Lys Arg Ala Ala Cys Glu Gln Leu His Gln Gln Gln Gln

901  CAG CAG CAG GAG GAG ACC GCC GCT GCC ACT CTG CTA CTG CAG GGT
     Gln Gln Gln Glu Glu Thr Ala Ala Ala Thr Leu Leu Leu Gln Gly

946  GAG GAA GAA GGG GAA GAA GAT TGATCAAACAGAATGAAACCCCCACACACAC
     Glu Glu Glu Gly Glu Glu Asp End

998  ACACATGCATACACACACACACAGCCACACACACAGAAAATATACTGTAAAGAAAGA

1057 GAGAAAATAAAAAGTTAAAAAGTTAAAAA
```

FIG. 10B

FIG. 11

Motif I, Purα, Purβ:

| | | | | | | | | | | | | | | | | | | | | | | |
|---|---|---|---|---|---|---|---|---|---|---|---|---|---|---|---|---|---|---|---|---|---|---|
| Rep αIa | V | D | I | Q | N | K | R | F | Y | L | D | V | K | Q | N | A | K | G | R | F | L | K | I |
| Rep αIb | L | V | R | Q | N | R | K | Y | Y | M | D | L | K | E | N | Q | G | R | F | L | R | I |
| Rep αIc | L | T | V | D | D | N | K | R | F | F | D | V | G | S | N | Y | G | V | F | M | R | V |
| Rep βI  | T | V | D | S | K | R | F | F | F | D | V | G | C | N | K | Y | G | V | F | L | R | L |

Motif II, Purα:

| | | | | | | | | | | | | | | | | | | | | | | | | |
|---|---|---|---|---|---|---|---|---|---|---|---|---|---|---|---|---|---|---|---|---|---|---|---|---|
| Rep αIIa | A | V | E | F | R | D | Y | L | G | D | F | I | E | H | Y | A | – | Q | L | G | E | E | P | S | Q | P | P | D |
| Rep αIIb | L | I | E | F | R | D | A | L | A | K | L | D | D | Y | G | V | A | E | E | P | A | E | L | P | E |

FIG. 17

| | | | | | | | | | | | | | | |
|---|---|---|---|---|---|---|---|---|---|---|---|---|---|---|
| Purβ | P | S | Y | R | N | A | I | T | V | P | F | W | G | K | F | G | A | F | C | R | Y | A | D | E | M |
| ERG-B | P | S | Y | D | S | V | R | R | G | A | W | N | M | N | S | G | L | N | K | S | | | | | |
| HAGEMON FACTOR | A | T | Y | R | N | V | T | A | E | Q | A | R | N | W | G | H | A | F | C | | | | | | |
| T-ANTIGEN | P | T | Y | G | T | D | E | W | E | Q | W | W | N | A | F | N | E | E | N | L | F | C | S | E | E | M |
| Purα | P | P | T | Y | R | N | S | I | T | V | R | Y | K | V | K | A | W | F | G | K | H | T | F | C | K | Y | S | E | E | M |

PORTION OF SV40 T-ANTIGEN Rb PROTEIN BINDING SITE

Probe: Labeled upTAR ol.    Anti-Tat ab

METHODS FOR IDENTIFYING COMPOUNDS THAT BIND TO PUR PROTEIN

This is a division of application Ser. No. 08/470,911, filed Jun. 6, 1995 which is a continuation-in-part of Ser. No. 08/014,943, filed Feb. 2, 1993, now U.S. Pat. No. 5,545,551, which is a continuation-in-part of Ser. No. 07/938,189, filed Aug. 28, 1992.

This invention was made, in part, with government support under grants CA55219-01 from the National Institutes of Health. The government may have certain rights in the invention.

TABLE OF CONTENTS

1. Introduction
2. Background Of The Invention
   2.1. Regulation of Eukaryotic DNA Replication
   2.2. Role of The Retinoblastoma Gene Product In Regulation Of Cell Cycle
   2.3. HIV-1 And Neurological Disease
3. Summary Of The Invention
4. Description Of The Drawings 5. Detailed Description
   5.1. The PUR Element
   5.2. The PUR Protein
      5.2.1. Isolation And Cloning Of PUR DNA
      5.2.2. Construction Of Expression Vectors Containing The Pur Coding Sequence
      5.2.3. Identification Of Transfectants Or Transformants Expressing The PUR Gene Product
      5.2.4. The PUR Protein
      5.2.5. The PUR Protein Binds The Retinoblastoma Gene Product (PRB)
      5.2.6. A Role For PUR In Regulation Of Viral Gene Expression
   5.3. Inhibitors Of PUR Protein
      5.3.1. PUR Antibodies
      5.3.2. Anti-Sense RNA And Ribozymes
      5.3.3. Triplex DNA Formation
      5.3.4. Pur-Related Derivatives, Analogues, And Peptides
      5.3.5. Screening Assay
   5.4. Uses Of PUR Protein And Its Inhibitors
   5.5. Diagnostic Methods For Detecting PUR Related Disorders
   5.6. Gene Therapy
6. Example: Identification And Characterization Of The PUR Protein And Its Sequence Element
   6.1. Materials And Methods
      6.1.1. Plasmids And Oligonucleotides Used
      6.1.2. Gel Shift Assays
      6.1.3. Determination Of The Molecular Weight Of The DNA-Binding Protein
      6.1.4. Methylation Interference Analysis
      6.1.5. DNA Synthesis Assays
   6.2. Results
      6.2.1. A Region Of Stably Bent DNA 1.65 kb Upstream Of The c-myc P1 Promoter
      6.2.2. Protein Specifically Bound To A Purine-Rich Sequence Element Adjacent To The DNA Bend
      6.2.3. UV Irradiation Cross-Links A Polypeptide With The Single-Stranded 24-mer Containing The Pur Element
      6.2.4. Methylation Interference Analysis Of Contact Points For Protein Binding To The Pur Element
      6.2.5. A Pattern Of Guanosine Bases Is Required For Single-Strand Binding Specificity
      6.2.6. PUR Factor Preferentially Binds A Single-Stranded Versus Double-Stranded PUR Element
      6.2.7. A Consensus PUR Element Conserved In Eukaryotes
      6.2.8. PUR Element Oligonucleotides Delay The Onset of DNA Replication In Serum Stimulated Human Fibroblasts
7. Example: Cloning and Sequencing PUR Gene
   7.1. Materials and methods
      7.1.1. Oligonucleotides used
      7.1.2. Screening of Expression Libraries For Proteins With Affinity For The Llabeled, Ssingle-stranded PUR Element
      7.1.3. Determination and Analysis Of The Nucleotide Sequence of PURα
      7.1.4. DNA Binding Studies Of The PUR-lacZ Fusion Protein
      7.1.5. Tissue Culture, Poly(a)$^+$ RNA Preparation, And Hybridization Analysis
      7.1.6. 5' And 3' Extension Of PURα mRNA
      7.1.7. Screening Libraries By DNA—DNA Hybridization
      7.1.8. GST-PUR Fusion Proteins
      7.1.9. PUR Protein Binding The Retinoblastoma Protein
   7.2. Results
      7.2.1. Isolation Of PUR Clones From A λGT11 Expression Library Based On Affinity For The PUR Element
      7.2.2. Specificity Of Single-stranded DNA Binding By PURα

Example: Association Of PUR Protein With HIV Tat Protein and Tat Responsive Viral Expression elements
   8.1. Materials And Methods
      8.1.1. Detection Of A Tat-PURα Complex In Human Glioblastoma Cells Expressing The HIV-1 Tat Gene
      8.1.2. Binding of PUR To The JCV UPTAR PUR Element In The Presence Or Absence Of Tat
      8.1.3. Association Of Tat And PURα Proteins In The Presence Or Absence Of The JCV UPTAR Element
   8.2. Results
      8.2.1. Complex Formation Between Tat-PURα

Example: Localization Of PURα Gene
   9.1. Materials and Methods
      9.1.1. Preparation of probes
      9.1.2. Fluorescence In Situ Hybridization (FISH)
      9.1.3. Hybridization To DNA Of Human-hamster Hybrid Cells Bearing Individual Human Chromosomes
   9.2. Results
      9.2.1. Chromosome Localization Of PURα By FISH
      9.2.2. Hybridization Analysis Of Genomic DNA From Human-hamster Hybrid Cell Lines Bearing Individual Human Chromosomes 5 or 6

1. INTRODUCTION

The present invention relates to the PUR protein, to nucleotide sequences and expression vectors encoding PUR, and to methods for inhibiting PUR activity. The PUR protein binds specifically to single stranded DNA in regions that coincide with eukaryotic origins of DNA replication, and the 5' flanking regions of a number of cellular oncogenes that are frequently found amplified in cancer. It was also found that the PUR protein is associated with the retinoblastoma suppressor protein, which plays a critical role in the regulation of cell proliferation. Mapping studies localize the purα gene to a region of the genome that is frequently deleted in various proliferative disorders, further indicating a role for PUR in regulation of cell proliferation. Additionally, the PUR protein binds to viral transcriptional elements which demonstrates a role for PUR protein in the regulation of viral gene expression.

Included in the invention are reagents that inhibit PUR activity. These reagents may be useful for treatment of viral diseases or treatment of hyper-proliferative diseases such as cancers that result from amplification and/or overexpression of cellular oncogenes.

2. BACKGROUND OF THE INVENTION

2.1. REGULATION OF EUKARYOTIC DNA REPLICATION

Cell division is a carefully regulated process that involves two events, the duplication of genomic DNA and the physical division of the two daughter cells. Before each new cell division cycle, a decision must be made by the cell of whether to proceed through a new round of DNA replication or withdraw from the cell cycle into a quiescent non-proliferating state. When regulation of this process breaks down the result is uncontrolled cell proliferation which may lead to diseases such as cancer.

Investigators of eukaryotic DNA replication have been faced with the challenge of identifying and characterizing both the specific chromosomal origins of replication and the regulatory proteins that control initiation of replication. Elucidation of the molecular mechanisms regulating DNA replication should lead to the development of therapeutic applications directed at inhibiting DNA replication and cell division.

Studies of DNA replication in mammalian cells has been difficult, due in part to the lack of suitable methods for mapping origins in large and complex genomes. In less complex organisms, such as prokaryotes, yeast and DNA tumor viruses, recent developments have lead to the identification of both cis-acting elements and polypeptides that bind specifically to these elements.

Several proteins from prokaryotes have been characterized which play a role in DNA replication and which bind to single-stranded DNA. The amino acids involved in DNA binding by certain of these proteins have been identified (Gutierrez et al., 1991 J. Biol. Chem. 266, 2104–2111). However, none of these single-stranded DNA binding proteins is known to have any sequence specificity.

In yeast, Saccharomyces cerevisae, cis-acting replication origins, referred to as ARS elements (autonomous replicating sequences), have been identified by their ability to allow extrachromosomal maintenance of plasmids. In general, yeast ARS sequences have a significantly higher A+T content than average chromosomal DNA. Recently a 67 Kd protein, referred to as ACBP (ARS-consensus binding protein) has been purified from yeast cell extracts and shown to bind preferentially to the T-rich single stranded DNA sequences found at the 3' end of the yeast ARS element (Hofmann and Gasser, 1991 Cell 64:951–960).

In a number of DNA tumor viruses, the sequences required for autonomous replication have also been mapped. Perhaps, the best studied of these viruses is Simian Virus 40 (SV40) and a single-stranded DNA-binding protein referred to as RP-Ab is required for replication initiated at the SV40 origin in vitro (Wobbe et al., 1987 Proc. Natl. Acad. Sci. 84:1834–1838; Erdile et al., 1991 J. Biol. Chem. 266:12090–12098). No sequence specificity has been reported for DNA binding by RP-A.

These results raise the possibility that sequence-specific, single-stranded-DNA binding proteins may serve an important function in the initiation of DNA replication. At this time, however, no amino acid sequence has been reported for any mammalian protein known to bind specifically to a single-stranded DNA element.

2.2. ROLE OF THE RETINOBLASTOMA GENE PRODUCT IN REGULATION OF CELL CYCLE

The product of the retinoblastoma tumor suppressor gene (pRB) operates to regulate progression through the cell cycle (Weinberg, R., 1995, Cell 81:323–330). The main function of pRB is to transmit proliferative signals to the transcriptional machinery mediating expression of genes necessary for progression through the cell cycle.

pRB binds to a number of cellular proteins and the association of pRB with these cellular proteins has been shown to be important in the regulation of pRB. In addition, pRB is differentially phosphorylated during different phases of the cell cycle. The phosphorylation of pRB alters its activity, causing it to release several cellular proteins with which it is associated, and allowing the cell to progress from the G1 to the S-phase of the cell cycle (Cobrinik et al., 1992, Trends Biochem. Sci. 17:312–315). For example, when pRB is under phosphorylated it binds to the E2F transcription factor (Chellappan et al., 1991, Cell 65:1053–1061). Phosphorylation of pRB leads to release of E2F, thereby enabling E2F to transactivate genes, the transcription of which it controls.

When pRB fails to undergo phosphorylation, progression through the cell cycle is blocked, highlighting the critical role pRB plays in the regulation of cell proliferation. The importance of pRB is further illustrated by the diverse body of evidence that indicates that disruption of retinoblastoma function is responsible for the pathogenesis of many human tumors. For example, in retinoblastomas, in small lung carcinomas, and in many sarcomas and bladder carcinomas, retinoblastoma function is lost through mutations in the retinoblastoma tumor suppressor gene (Horowitz et al., 1990, PNAS USA 87:2775–2779).

Identification of cellular proteins that associate with pRB and regulate its activity during the cell cycle will provide useful targets for use in screening assays designed to identify therapeutic reagents that regulate cell proliferation.

2.3. HIV-1 AND NEUROLOGICAL DISEASE

Human immunodeficiency virus type I (HIV-1) infection can lead to severe immunosuppression, in addition to depletion of CD4-positive T-lymphocytes, and other clinical syndromes. More than 60% of all HIV-1 infected individuals suffer from a series of devastating clinical disorders of the central nervous system (CNS) caused by direct infection and/or reactivation of other opportunistic pathogens in the cells of brain.

JC virus (JCV) is a DNA papovavirus that is widespread in latent form in humans. In brains of individuals infected with HIV-1, JCV is activated, leading to the progressive multifocal leukoencephalopathy (PML), a formerly rare disease that almost exclusively occurred in persons with underlying lymphoma and chronic lymphocytic leukemia (Berger et al., 1995, J. Neurovirology 1:5–18). This neurodegenerative disease is now seen with increasing frequency and is estimated to arise in more than 8% of all HIV-1 infected individuals.

The high incidence of PML among AIDS individuals in comparison to the other immunocompromised patients implies that the presence of HIV-1 in the brain may, directly or indirectly contribute to the pathogenesis of this disease. In support of this model, earlier in vitro studies have indicated direct intercommunication between HIV-1 and JCV through the HIV-1 encoded regulatory protein, Tat (Tada et al., 1990, Proc. Natl. Acad. Sci. USA 87:3479–3483). The Tat protein presumably possesses the ability to augment transcription of the JCV late promoter in human glial cells.

The tat gene of the human immunodeficiency virus type 1 (HIV-1) encodes a protein that transactivates transcription of the HIV-1 LTR promoter and is required for viral replication (Arya, S.K., 1989, Science 229:69–73). The Tat protein binds a cis-acting RNA target sequence termed TAR, positioned in the transcribed 5' leader (+1 to +59) (Berkhout, B., 1989, Cell 59:273–282). The mechanism by which Tat activates transcription is not completely understood. Several observations suggest that Tat may exert a primary effect on elongation, although effects on elongation and initiation may be mechanistically linked. The amino-terminal portion of Tat comprises a transactivation domain (Southgate, C. et al., 1991, Genes Dev. 5:2496–2507). By tethering Tat and Tat deletion mutants to upstream DNA sites as GAL4/Tat fusion proteins, it had been demonstrated that the RNA-binding domain of Tat is not required for transactivation. This implies that the major function of TAR is to bring Tat in contact with the promoter, most likely in conjunction with a cellular TAR-binding protein. Whereas Tat binds a U-rich bulge in the secondary structure of TAR, sequences in a nearby RNA loop are also essential for transactivation, and it is thought that the loop region may bind cellular factor(s) involved in activation.

The 5' leaders of certain of the late JCV transcripts contain elements homologous to TAR, and transcription of these mRNAs is strongly stimulated by Tat (Kenney et al., 1986, J. Virol. 58:210–219; Tada, H. et al., 1990, Proc. Natl. Acad. Sci. USA 87:3479–3483). Furthermore, JCV transcriptional activation by Tat requires interaction with a cellular protein and the Tat-responsive element located in the JCV late region promoter upstream of the transcriptional start sites (Chowdhury, M. et al., 1993, Oncogene 8:887–892).

Identification of cellular protein(s) that interact with Tat protein to activate viral transcription will facilitate the screening and identification of therapeutic molecules designed to inhibit this interaction. Such molecules will have therapeutic value in the treatment of viral disease.

3. SUMMARY OF THE INVENTION

The present invention relates to the PUR gene and the biologically active polypeptide coded for by the PUR DNA sequence. The present invention also relates to inhibitors of PUR activity which may include neutralizing anti-PUR antibodies, anti-sense RNA and ribozyme molecules that are specifically targeted to prevent translation of PUR mRNA and to derivatives, analogues and PUR related polypeptides that inhibit PUR activity. Also included in the invention are reagents that interfere with the specific DNA/protein interaction between the PUR protein and PUR element, such as oligonucleotides that bind and form triplex helical structures at the PUR element.

The invention is based, in part, on the discovery and characterization of the PUR element consensus DNA sequence. The location of PUR elements is found to coincide with regions of DNA that are believed to represent origins of replication. The PUR element is also found 5' to a number of cellular genes including the frequently amplified c-myc, int-2 and lck oncogenes suggesting that PUR elements may also function to regulate gene expression.

The invention is also based on the isolation and characterization of a cDNA clone coding for a cellular factor, referred to as the PUR protein, which binds in a sequence specific manner to single-stranded PUR element DNA sequence. In addition, the invention is based on the discovery that the PUR protein binds specifically to the retinoblastoma protein, herein referred to as pRB protein. The retinoblastoma gene is perhaps the most extensively studied of the tumor suppressor genes. Current interest in pRB is based on observations that inactivation of pRB frees cells from the normal growth constraints imposed by a functional pRB. Inactivation of pRB results in uncontrolled cell proliferation and tumor cell growth. The invention also relates to methods for controlling the cell cycle by manipulating the interaction of PUR and/or pRB so that their activity is regulated. Inhibition of PUR protein activity may be of therapeutic value in the treatment of hyperproliferative diseases such as cancers which result from amplification or over expression of cellular oncogenes.

Gene mapping experiments have localized the purα gene to the 5q31 region of the genome. Interestingly, this region of the genome is frequently deleted in a number of proliferative disorders. Included in the present invention are diagnostic methods developed to detect mutations in the pur gene and/or aberrant expression of the PUR protein.

Also included in the invention are reagents that interfere with the specific association between PUR and the HIV encoded Tat protein. In addition, reagents that inhibit the binding of PUR to Tat responsive viral transcriptional elements are included in the invention.

The invention is based on the discovery that the PUR protein binds specifically and with high affinity to the virally encoded HIV Tat protein. In addition, the Pur-Tat complex was found to bind specifically to a region of the JCV late promoter, thereby indicating a role for PUR protein in the regulation of viral gene expression.

4. DESCRIPTION OF THE DRAWINGS

FIG. 1. Structural features in a region of DNA bending upstream of the human c-myc gene. Positions of DNase 1-hypersensitive sites and CTF/NF-1 consensus binding sites are indicated by solid arrows at the top (Siebenlist et al., 1984, Cell 37:381–391). The open arrow (RIC) denotes the center of a zone of initiation of DNA replication (Vassilev, L., and E. M. Johnson, 1990, Mol. Cell. Biol. 10:4899–4904). The position of the 467-bp insert of plasmid pMYC47 is indicated and expanded below, showing the bend center as identified in FIG. 2. pMYC47 contains a tandem duplicate of this fragment. Restriction endonuclease cleavage sites are abbreviated as follows: HIII, HindIII; P, PstI; Spl, SpeI; HI, HpaI; X, XhoI; S, Sau3AI; H, HaeIII; D, DdeI; R, RsaI; A12, AvaII; A1, AvaI.

Figure 2A:
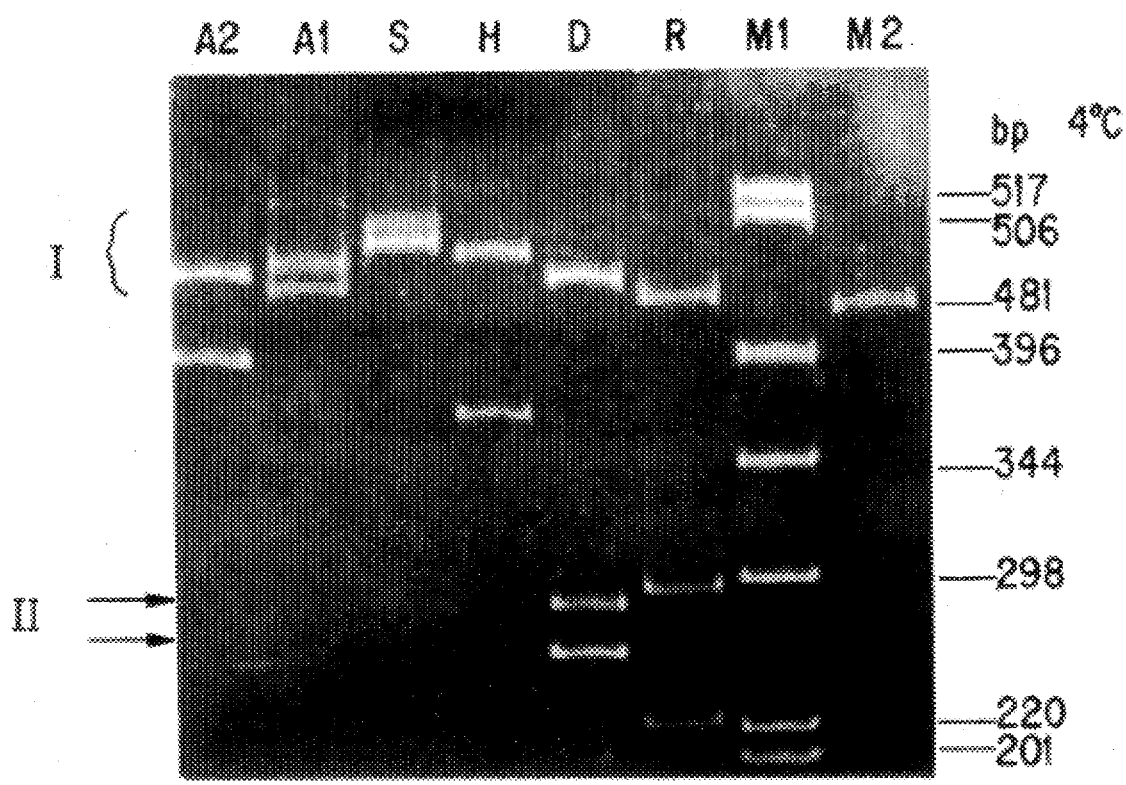

FIGS. 2A and B. Location of an intrinsically bent DNA segment upstream of the c-myc gene. A tandemly duplicated 467-bp Sau3A1 fragment mapped as in FIG. 1 (−1970 to −1504 from the P1 transcription start site), was cloned in plasmid pMYC47 and excised for bending analysis. It yields a 973-bp fragment including polylinker sequences. The tandem repeat was treated with single-site restriction enzymes to yield circular permutations of the 467-bp fragment. Enzymes are abbreviated as in FIG. 1. Lane M1 contains markers from the Bethesda Research Laboratories 1-kb ladder; lane M2 contains the 481-bp Bgl1-Xmn1 fragment of pUC19. Asterisks indicate two marker bands which are themselves more than 10% retarded due to bending (Stellwagen, N. C., 1983, Biochemistry 22:6186–6193). (A) Polyacrylamide gel electrophoresis showing anomalous migration of 467-bp fragments at 4° C.

(I, bracket at left). (The top band in lane S is a partial digestion product.) In lane D (Dde1 digest), two fragments of 252 and 254 bp, are also produced from the original 973-bp plus polylinker sequences. One of these is retarded relative to the other at 4° C. (II, arrows at left). (B) Elimination of bending at 60° C. No anomalous migration of the 467-bp fragments is seen (I), and the 252- and 254-bp fragments now migrate together (II).

Figure 3:
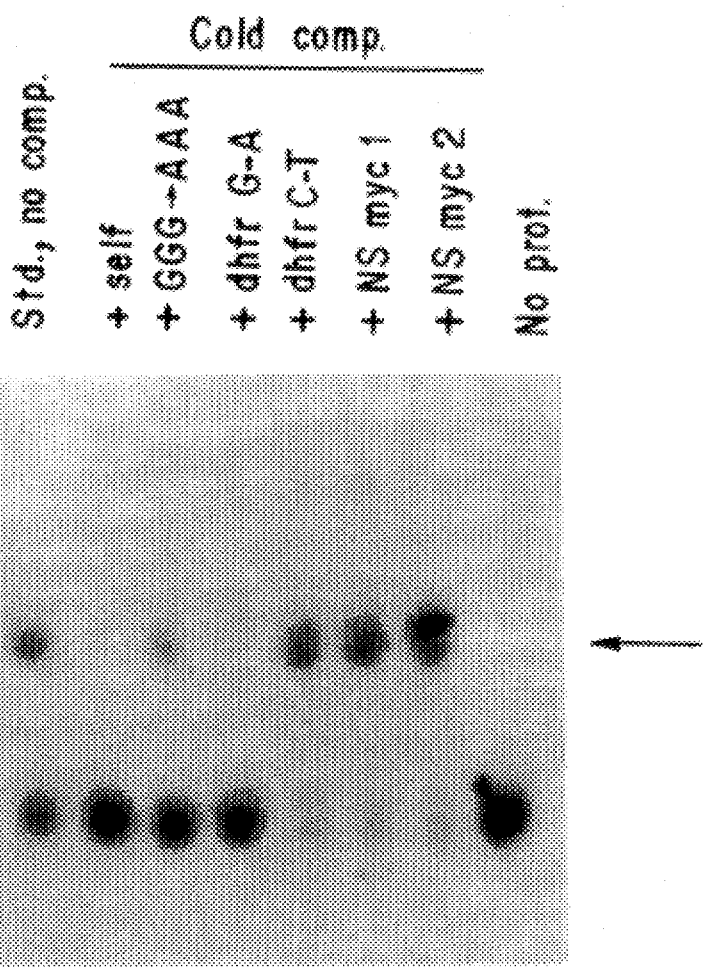

FIG. 3. Specificity of protein binding to the purine-rich strand of an element near the center of DNA bending. The probe is end-labeled single-stranded 24-mer MF0677, described in Section 6.1.1, corresponding to the purine-rich strand of nucleotides −1648 to −1625 upstream of the human c-myc P1 transcription start site. The left lane is the standard gel band shift binding reaction, described in Section 6.1.3, with no added competitor; the right lane is the reaction with an added HeLa nuclear extract. Unlabeled competitors are at 100X excess. Self, 24-mer MF0677; GGG>AAA, MM0677, the 24-mer mutated as indicated; dhfr G-A, DR3529 (purine-rich 24-mer from the hamster dhfr replication initiation locus); dhfr C-T, DF3506, (pyrimidine-rich complement to DR3529); NSmyc1 and Nsmyc2, MF0562 and MR0740, respectively (irrelevant control oligonucleotides from the c-myc locus).

Figure 4A:
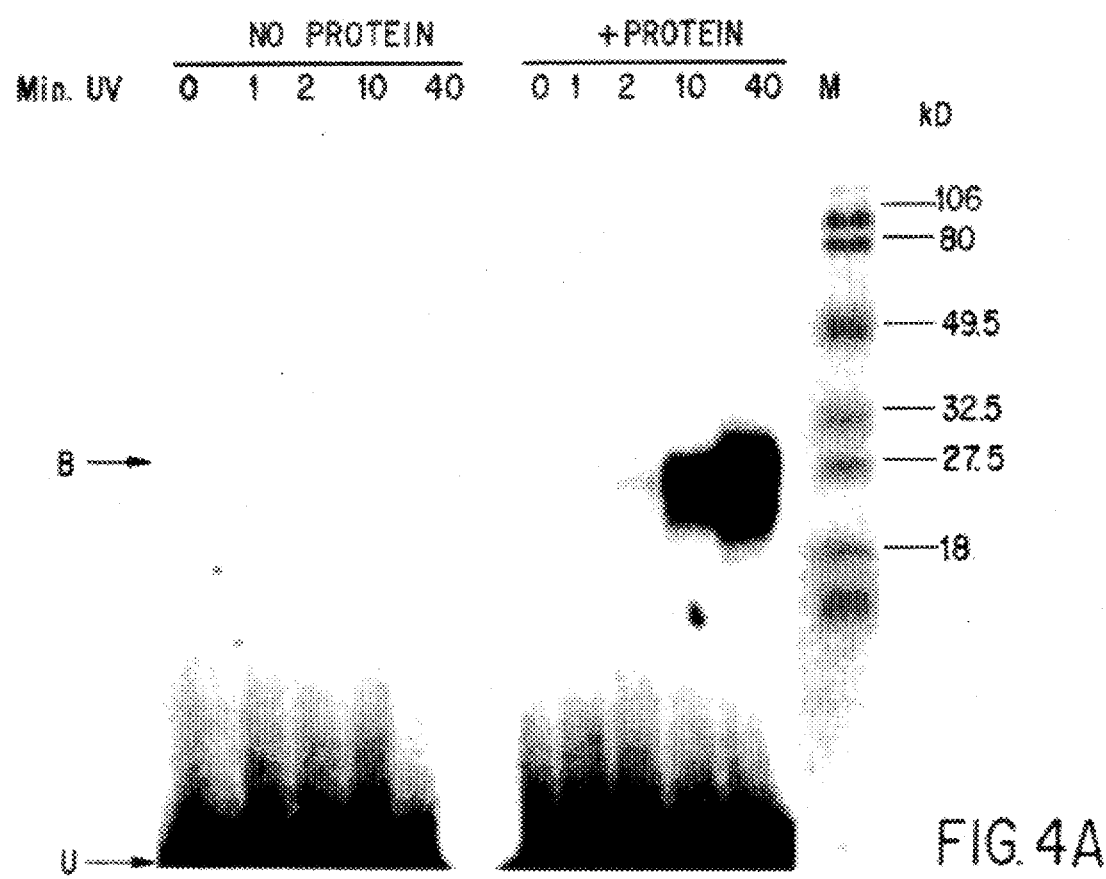

FIGS. 4A and B. Specific UV cross-linking of a polypeptide with the PUR element. In each experiment, end-labeled 24-mer oligonucleotide MF0677, corresponding to the G-A strand of the c-myc PUR element, was either subjected or not subjected to UV cross-linking in the presence or absence of a HeLa nuclear extract as described in Section 6.2.3. The mixture was then subjected to SDS polyacrylamide gel electrophoresis in a 10% gel and autoradiographed. (A) Time course of UV cross-linking. Lanes were reacted without and with HeLa nuclear extract, as indicated. Cross-linking was performed for the times indicated. B, bound label; U, unbound label. Positions of protein molecular weight markers are shown at the right. (B) Specificity of protein-DNA cross-linking. The lane at left represents the reaction with no protein. Reactions were performed in the presence of either 25 or 75 μg of unlabeled poly(dI-dC), a carrier to reduce potential nonspecific binding, per ml. 0, no added unlabeled competitor oligonucleotide. All competitors were added at 300-fold molar excess over the labeled probe. S, excess of the specific unlabeled 24-mer MF0677; NS, excess of nonspecific oligonucleotide MF0562, dhfr, excess of 24-mer DR3529 representing the hamster dhfr version of the PUR element [reacted in 25 μg of poly(dI-dC) per ml]. The position of the PUF-binding protein is indicated by an arrow.

Figures 5A, 5B:
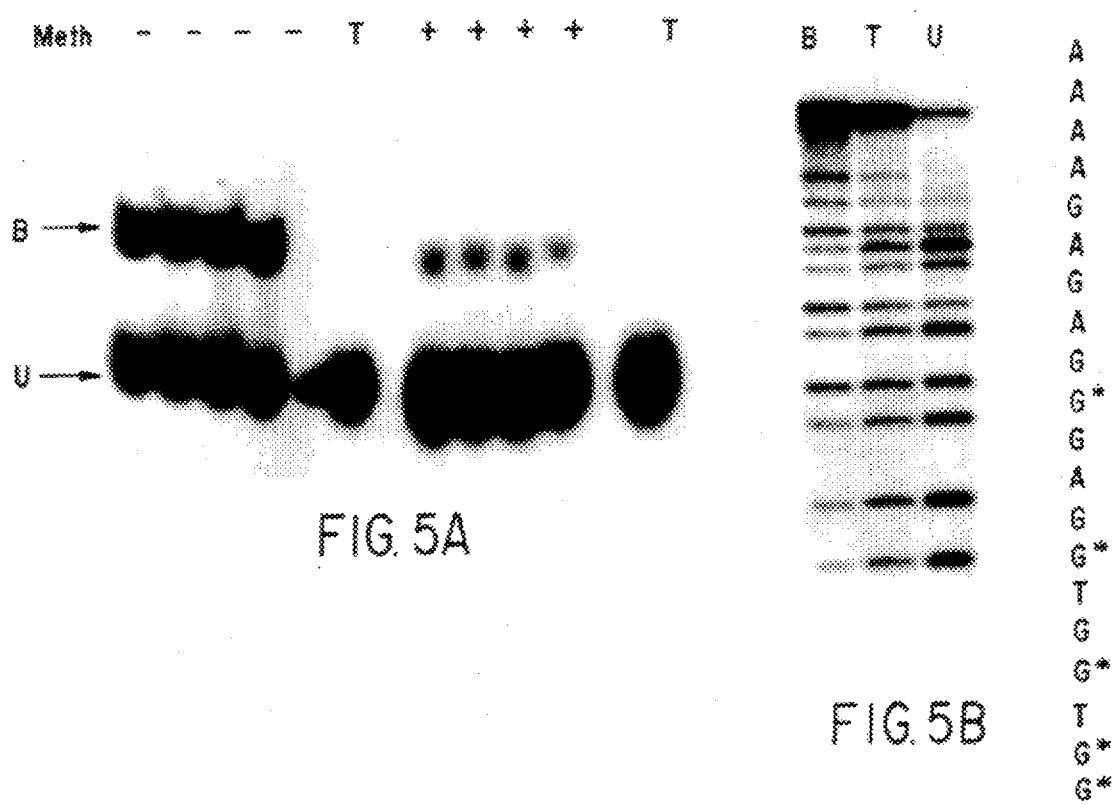

FIG. 5A and B. Methylation interference analysis of purine contact points by protein specifically binding the purine-rich strand of the PUR element. After derivatization $^{32}$P-end-labeled 24-mer oligonucleotide MF0677, containing the PUR element, with dimethyl sulfate, the single-stranded probe was allowed to react with protein in HeLa nuclear extract. (A) Gel band shift following derivatization with two levels of dimethyl sulfate as described in Section 6.2.4. Lanes −, reaction with 53 mM dimethyl sulfate, calculated to derivatize approximately one purine base per oligonucleotide molecule; +, reaction with fivefold-higher dimethyl sulfate; T, reaction without added protein. Each half of the gel represents a single methylation reaction from which bands were purified for further sequence analysis as in panel B. (B) DNA was purified from B (bound), U (unbound), and T (total) bands from the reaction shown in lanes—of panel A, cleaved at methylated purine residues by reaction with piperidine, and subjected to electrophoresis and autoradiography as described in Section 6.1.5. Starred bases indicate those preferentially represented in U versus B lanes.

Figure 6:
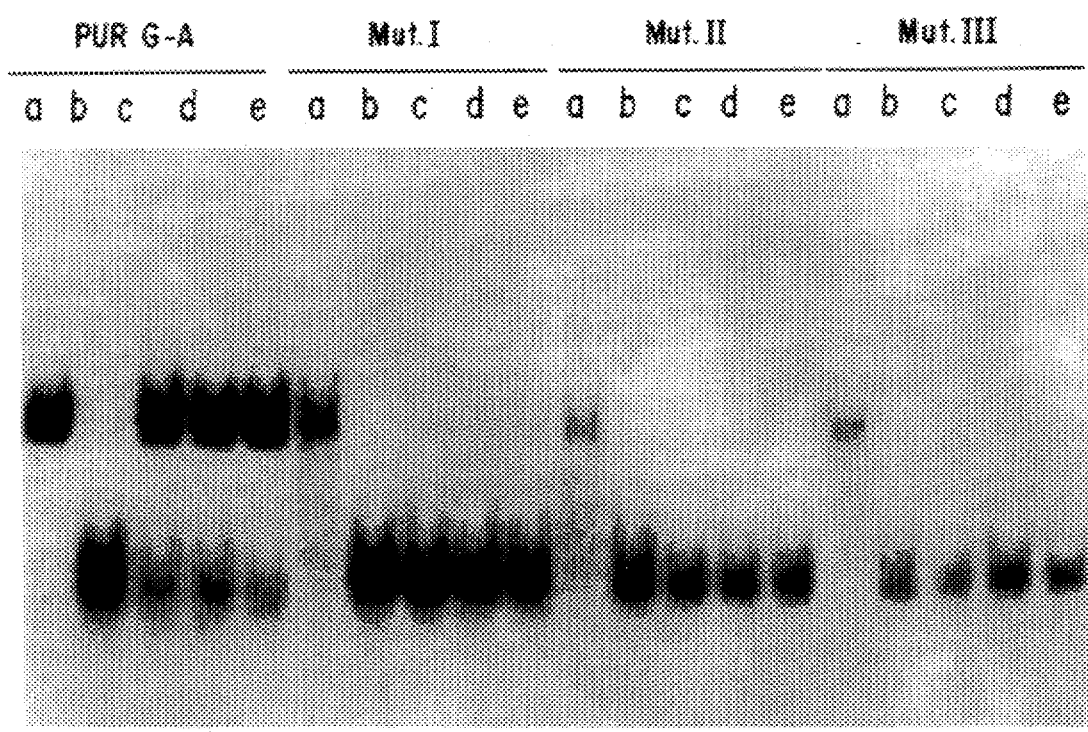

FIG. 6. Mutation analysis of nucleotides essential for specific binding to the PUR element. Gel retardation of single-stranded probes by protein from HeLa nuclear extract was performed as described in 6.1.4. The four oligonucleotides listed at the top were used as probes. Pur G-A is the oligonucleotide MF0677, and Mut. I, II, and III are mutated oligonucleotides MM0677 (GGG>AAA in FIG. 3), MA0677, and MB0677, respectively. Sequences are listed in 6.1.1. Lanes: a, standard binding reaction with no added competitor; b to e, reactions with added 30-fold excess of unlabeled competitor oligonucleotides PUR G-A, MM0677, MA0677, and MB0677, respectively.

Figure 7:
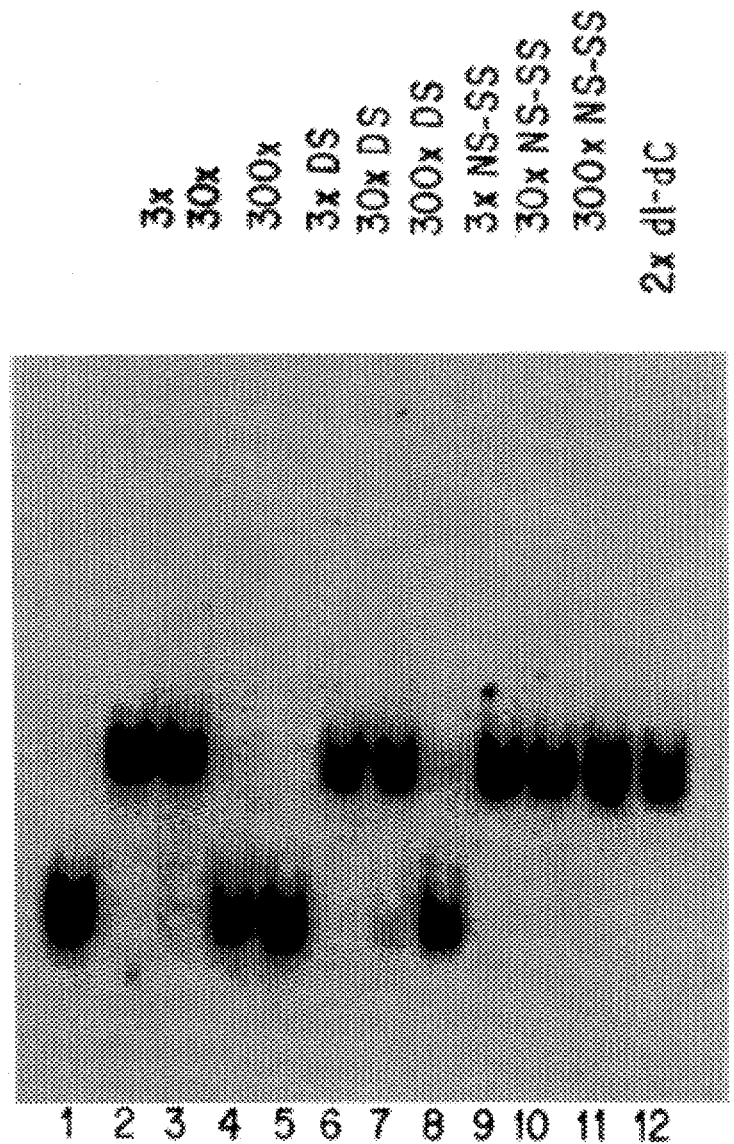

FIG. 7. Affinity of the PUR factor for single-stranded versus double-stranded PUR element. Single-strand PUR oligonucleotide MF0677 was used as a probe in the standard gel band shift assay described in Section 6.1.3. Unlabeled single-or double-stranded oligonucleotides were added as competitors. Lane 1 has no added protein; lane 2 is the standard reaction with no added competitor. Excesses (3-, 30-, and 300-fold) of the following oligonucleotides were added: SS, single-stranded MF0677, DS, double-stranded version of the 24-mer containing the PUR element made by annealing MF0677 and MR0700; NS-SS, nonspecific single-stranded oligonucleotide MR0740.

FIG. 8. Sequence of the PUR element region upstream of the human c-myc gene (SEQ. ID NO:1). Numbering at the left is relative to the HindIII cleavage site 2,325 bp upstream of the P1 transcription start site. Numbering at the right is relative to the P1 start site. Indicated are two repeats of the yeast ARS consensus element each with 10-of-11-bp homology (solid arrows), two repeats of the PUR consensus element of Table 1, the first with 100% homology and the second with 14 of-16-bp homology (dotted area), and the sequence of oligonucleotide MF0677, used in binding studies (open box). Additional repeated elements within this region (GAGGGA and ATTATAT) are also indicated.

Figure 9:
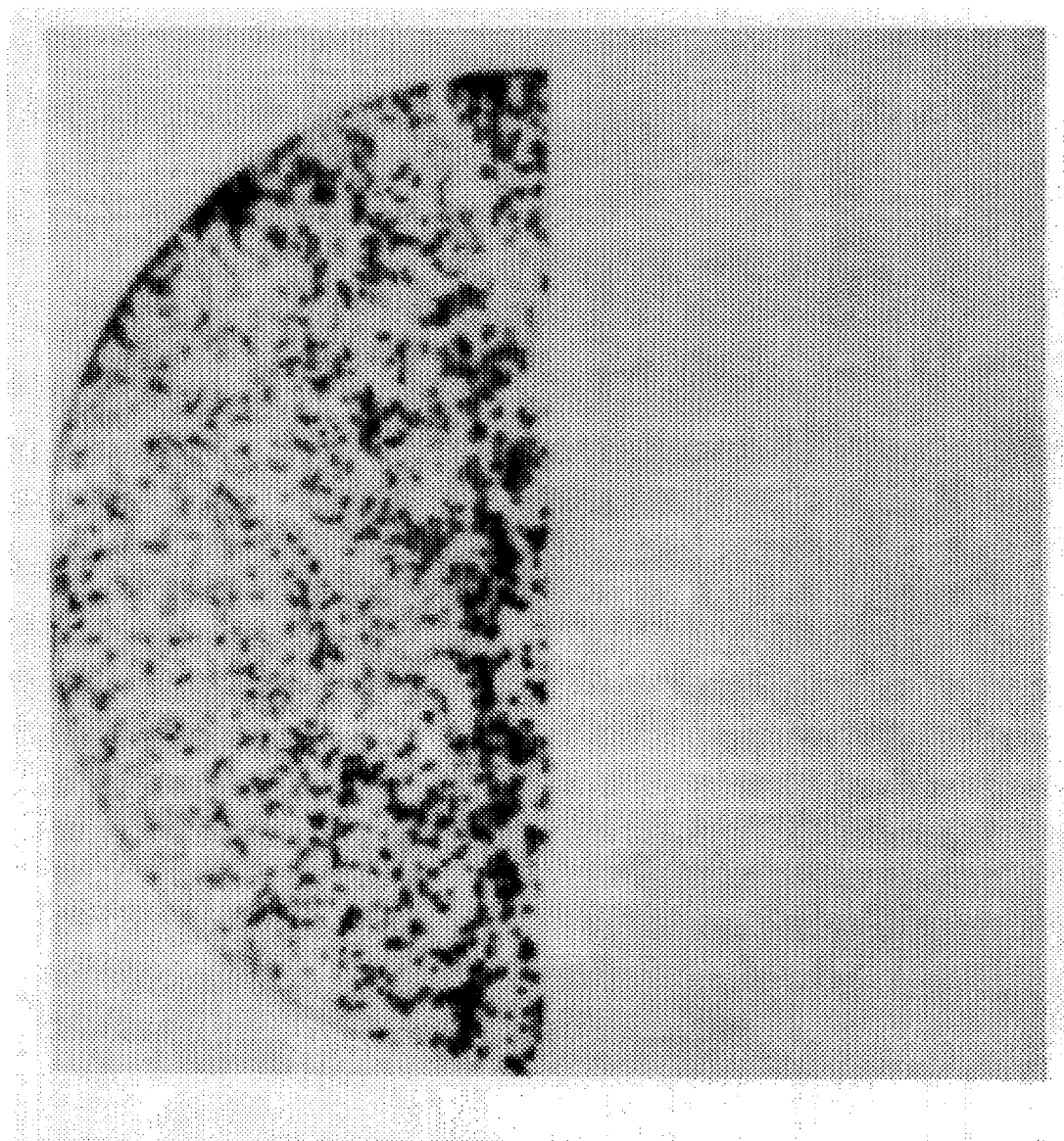

FIG. 9 Specific oligonucleotide binding by λabs. λAB2 phage were plated, induced and transferred to nitrocellulose membranes. Each membrane was then cut in half, and the halves incubated separately in the presence of MF0677 oligonucleotide, $^{32}$P-end-labeled as described in Section 7.1.2. The left half was incubated in the presence of an excess of unlabeled non-specific competitor MF0562, while the right half was incubated in the presence of excess unlabeled specific competitor (MF0677).

FIG. 10 Nucleotide sequence of Purα (SEQ. ID NO:2). The nucleotide sequence shown is derived from phage clones λAB6 and λHE1. The amino acid sequence (SEQ ID NO:3) of the open reading frame is indicated beneath the nucleotide sequence (SEQ ID NO:2). Numbering begins with the first methionine. The line beneath the sequence at base −9 indicates the first base of the λAB6 clone. Singly-underlined amino acid residues in bold type indicate class I repeats. Doubly-underlined amino acid residues in bold type indicate class II repeats.

FIG. 11 Two repeat motifs in Purα and Purβ. The class I repeat motifs (three from Purα and one from Purβ) are aligned at top, [αIa: (SEQ ID NO:4); αIb: (SEQ ID NO:5); αIc:(SEQ ID NO:6); βI: (SEQ ID NO:7)] and the class II repeat motifs (two from Purα) are aligned at bottom. [αIIa: (SEQ ID NO:8); αIIb:(SEQ ID NO:9)]. Solid boxes indicate identical amino acid residues, dotted boxes indicate conservative changes.

Figure 12A:
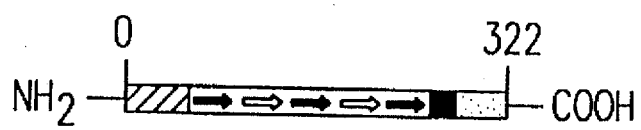
Figure 12B:
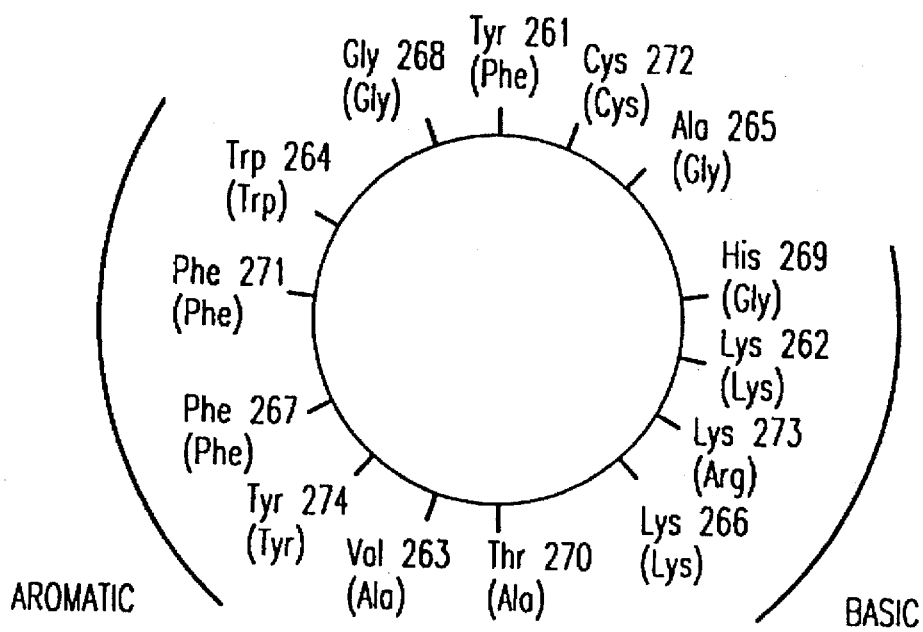

FIGS. 12A and B. Arrangement of amino sequence domains in Purα. A) Domain structure of Purα. The glycine-rich and glutamine, glutamate-rich domains both contain 50% or more of those respective amino acids. The class I repeats and the Class II repeats are described in FIG. 11. The amphipathic helix is described in FIG. 12B B) Axial view of the predicted amphipathic helix of Purα. Basic and aromatic faces are indicated. Numbers indicate the position of each amino acid residue in Purα. Bracketed residues indicate the amino acids occupying the equivalent positions in the homologous region of Purβ.

Figures 13A, 13B:
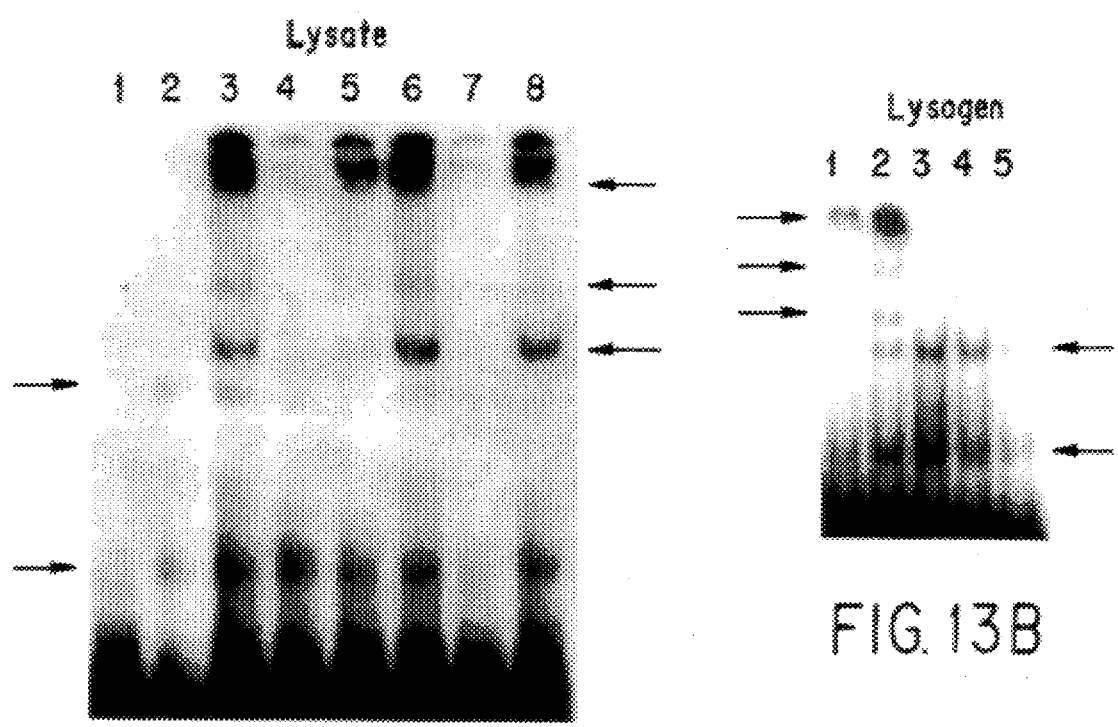

FIGS. 13A and B. Gel Shift assay of protein extracts from λAB clones. Gel shift assays using labeled MF0677 probe were performed as described in Section 6.1.3.

Left: Assay of protein extracts prepared from lysates of λAB4. Lane 1 displays probe in the absence of protein. Lane 2 displays probe in the presence of a control protein extract prepared from Y1090 cells infected with λovalb, a chicken ovalbumin gene clone in λgt11 (Clontech). Lane 3 displays probe in the presence of protein extract from Y1090 cells infected with λAB4. Lane 4 displays signal with 5-fold dilution λAB4 extract. Lanes 5 through 8 represent reactions similar to that of lane 3, but with cold competitor added; lane 5, 5-fold excess of MF0677: lane 6, 5-fold excess of polyA: lane 7, 20-fold excess of MF0677: lane 8, 20 -fold excess of polyA. Filled arrows indicate bands specific to the clone, open arrows indicate bands present normally in E. coli. Right: Assay of lysogens derived from λAB6. Lanes 1 and 2 display signal from IPTG induced lysogen either in the presence (lane 1) or the absence (lane 2) of a 5-fold excess of MF0677. Lane 3 displays signal from uninduced lysogen. Lane 4 displays signal from IPTG-induced Y1090. Lane 5 indicates signal from uninduced Y1090.

Figure 14A:
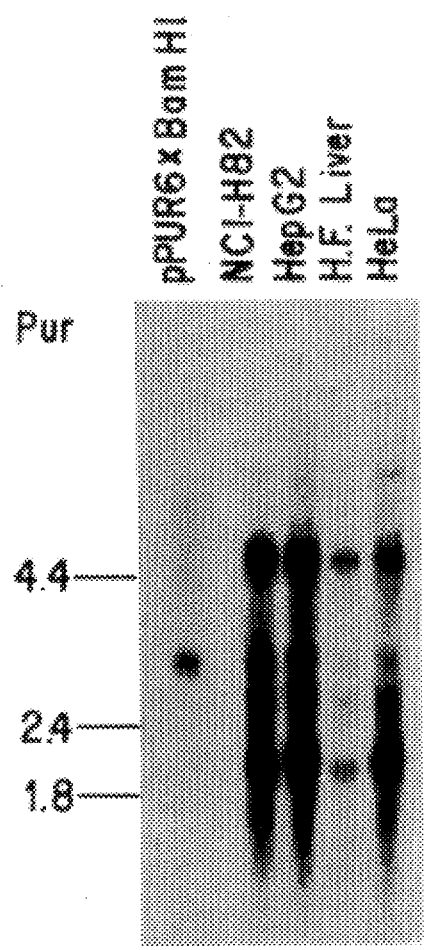

FIG. 14 Blot hybridization of human mRNAs with Purα probe. Poly A+ RNA prepared from tissue or culture cells was subjected to electrophoresis and blotted as described in Section 7.1.5. (14A) Membranes were probed with labeled-Purα cDNA. Lanes are: pPUR6xBamHI—pPUR6 DNA digested with BamHI; NCI-H82—lung tumor cell line mRNA; HepG2—liver hepatoma mRNA. (14B) The lower box displays the results of hybridization of the same membrane to a glyceraldehyde phosphate dehydrogenase probe as a loading control.

Figures 15A, 15B:
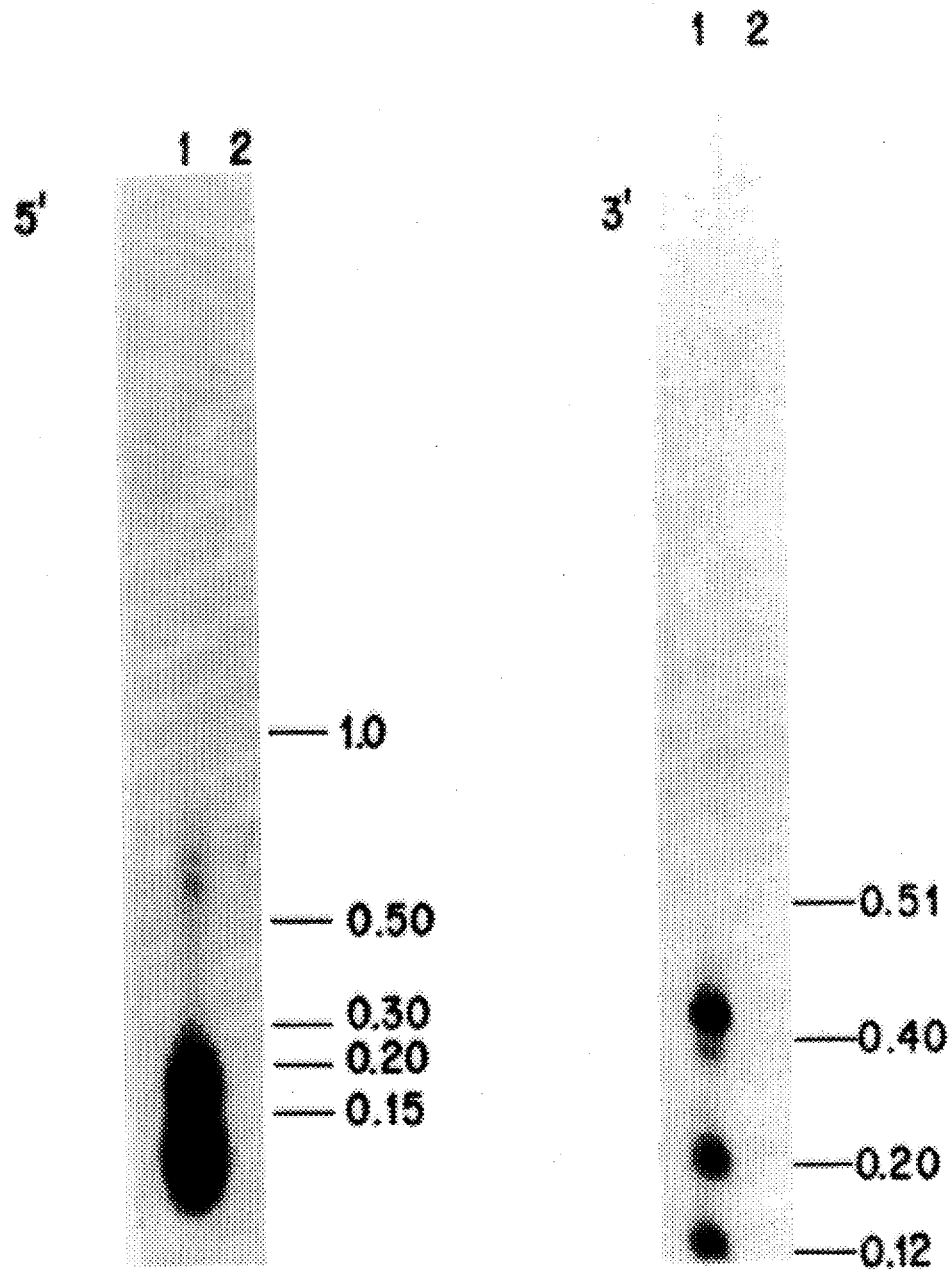

FIG. 15 5' and 3' RACE extension of Purα cDNA. Products of the RACE reactions outlined in Section 7.1.6 were subjected to electrophoresis in alkaline denaturating agarose gels, Southern blotted to Gene-Screen Plus membranes and hybridized to a Purα probe. In each case numbers on right indicate molecular weight markers in kb. Lane 1 in each case indicates the reaction containing both primers. Lane 2 in each case represents a control reaction in which one primer was omitted. Primer PDT-01 (SEQ ID NO:15) (TATCTGCAGTTTTTTTTTTTTTTTTTT) was used to anneal to the poly-A tail generated for both 5' and 3' RACE. (15A): 5' RACE. Pur-specific primers used were EX-270 (SEQ ID NO:16). (CTCGGCGATCTTCAGGAA), corresponding to nucleotides 270 to 253, for the first amplification reaction, and EX-174 (SEQ ID NO:17 (TTCTAAGCTTCGTCTCGTGCTGCAGCCC), corresponding to nucleotides 174 to 157 plus a HindIII linker, for the second amplification reaction. (15B): 3' RACE. Pur-specific primers used were EX-695 (SEQ ID NO:18) (TCTTCGATGTGGGCTCCAAC), corresponding to nucleotides 695 to 714, for the first amplification reaction, and EX-990 (SEQ ID NO:19) (ACACACACACACATGCATAC), corresponding to nucleotides 990 to 1009, for the second amplification reaction.

Figure 16:
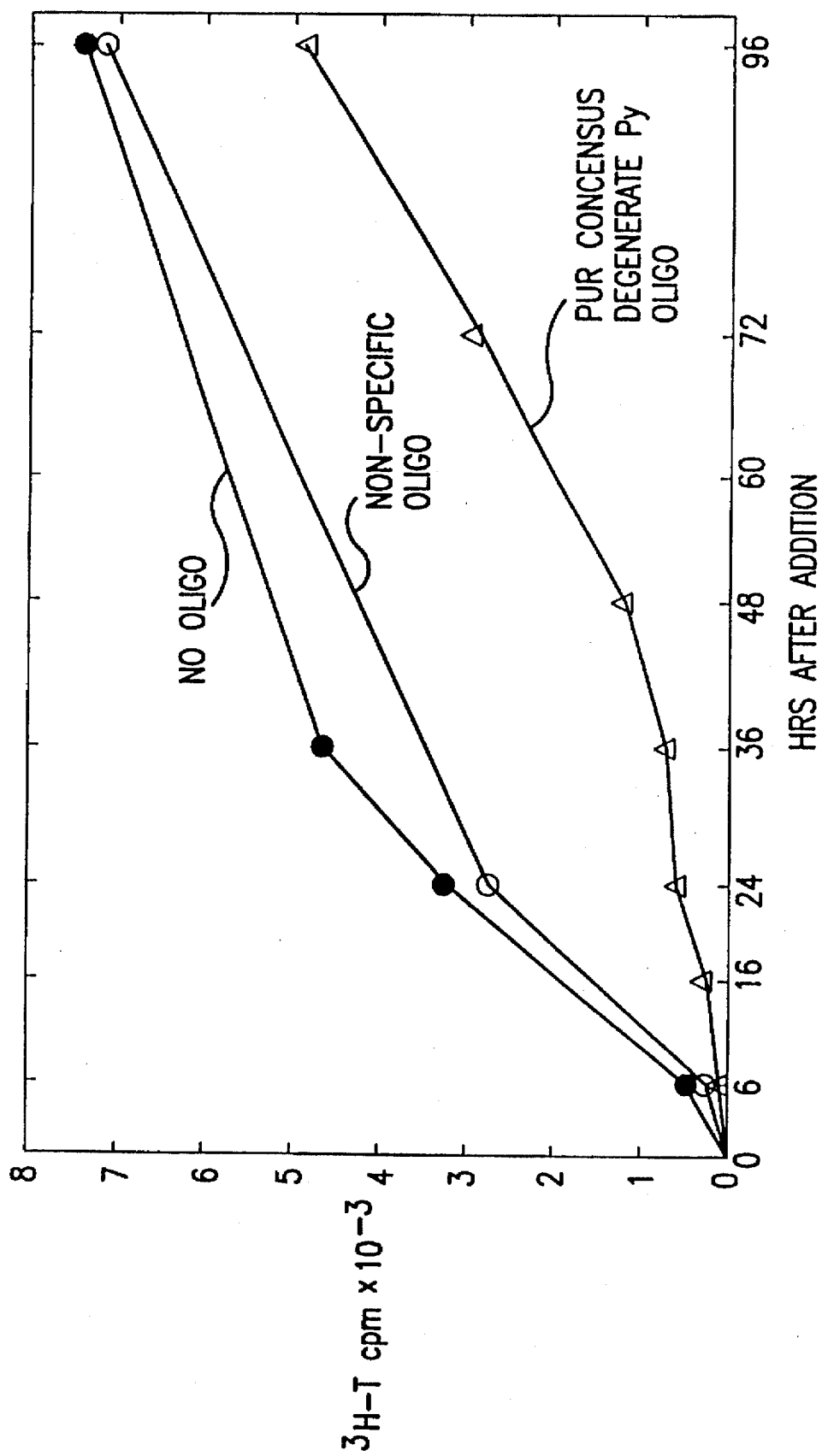

FIG. 16. Delay in the onset of DNA synthesis in serum-stimulated human fibroblasts, by PUR element oligonucleotides.

FIG. 17. Regions of homologies between PUR protein and SV40 Large T-antigen [Purβ:(SEQ ID NO:10); ERG-B: (SEQ ID NO:11); HAGEMON FACTOR: (SEQ ID NO:12); T-Antigen: (SEQ ID NO:13); Puraα: (SEQ ID NO:14)].

Figure 18:
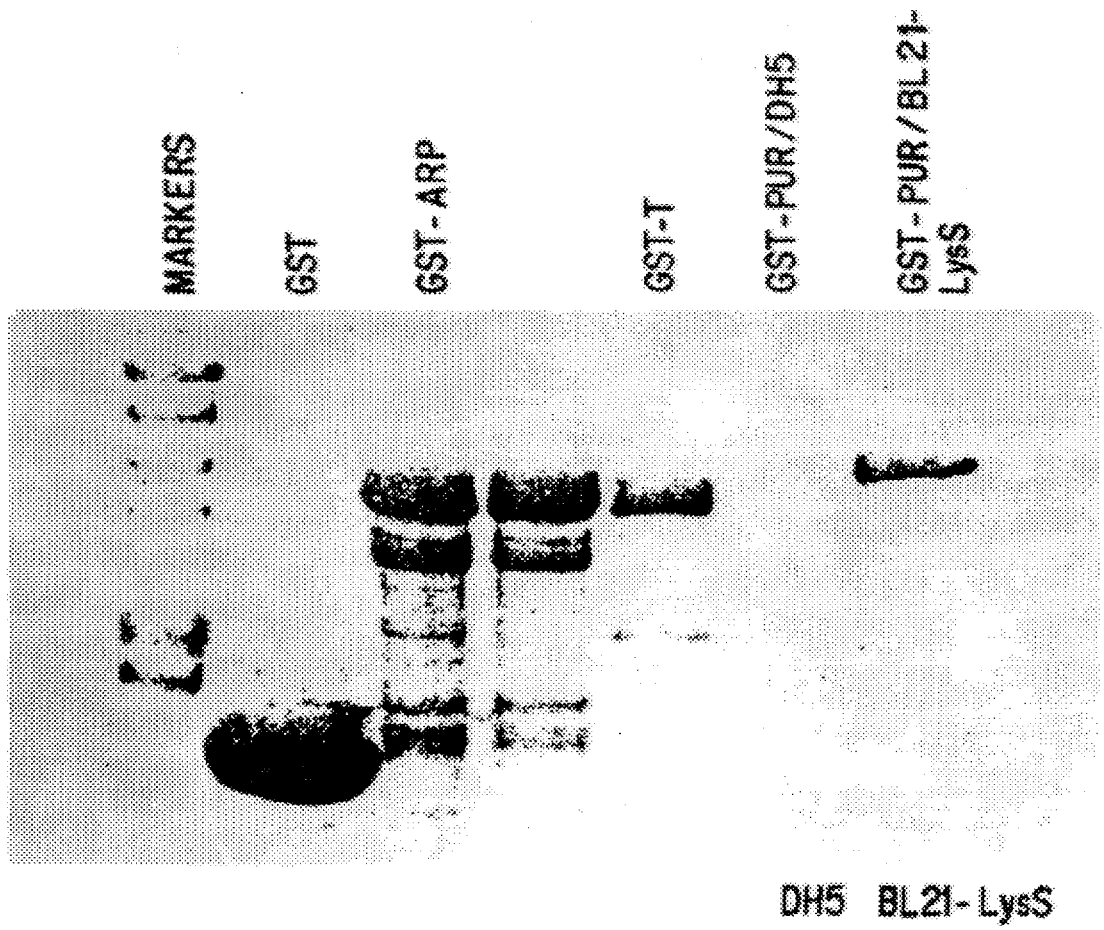

FIG. 18. Expression of GST-PUR protein in E. coli. SDS polyacrylamide gel of various GST-fusion proteins eluded from a glutathione-linked agarose column. The last two lanes represent PUR-GST fusion protein prepared form two different strains of E. coli, DH5 and BL21-LYS.

Figure 19:
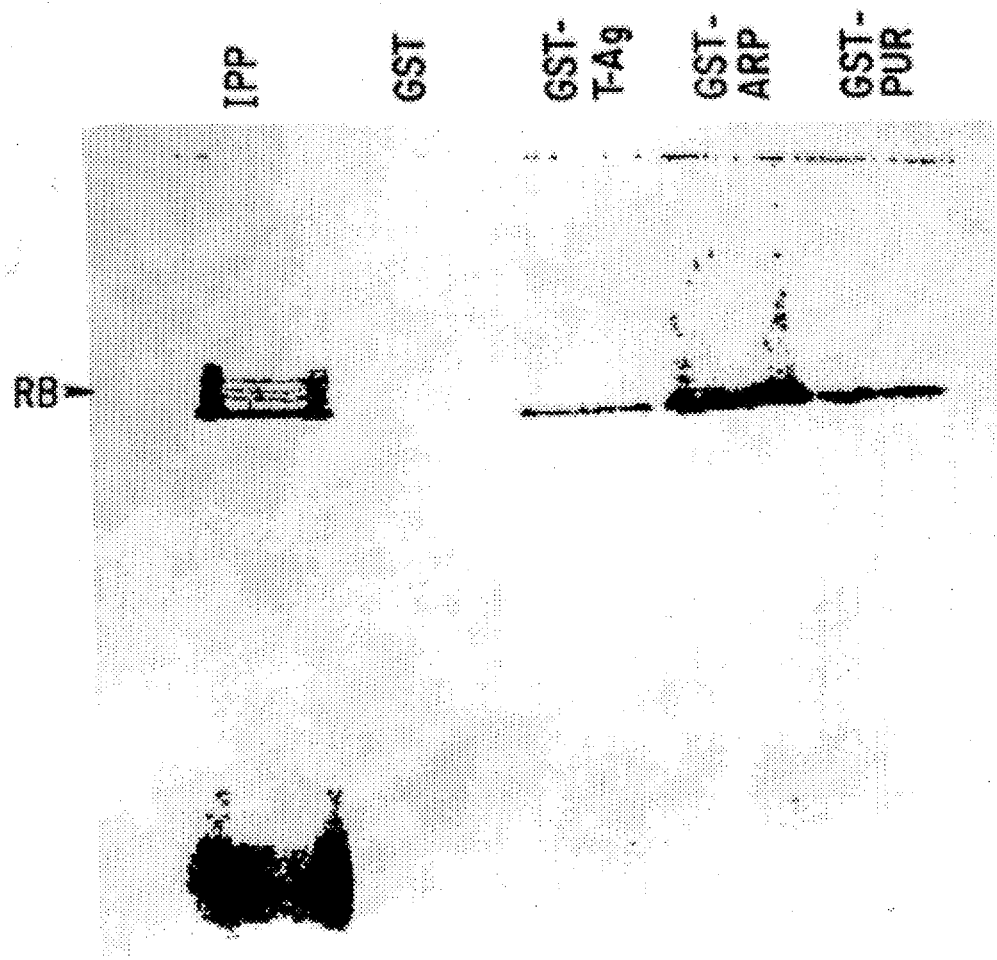

FIG. 19. PUR binds the pRB protein in WR2E3 cell extracts as determined by passage of extracts over PUR-GST columns. Column bound proteins were subjected to SDS-polyacyralmide gel electrophoresis and blotted onto nitrocellulose membrane. The pRB protein was detected using anti-pRB antibodies. PUR preferentially binds the unphosphorylated form of pRB. Lane 1 is Retinoblastoma protein; Lane 2 is GST alone; Lane 3 is GST-T antigen fusion protein; Lane 4 is GST-ARP fusion protein which is another protein that interacts with the retinoblastoma protein and Lane 5 is GST-PUR fusion protein.

Figures 20A, 20B:
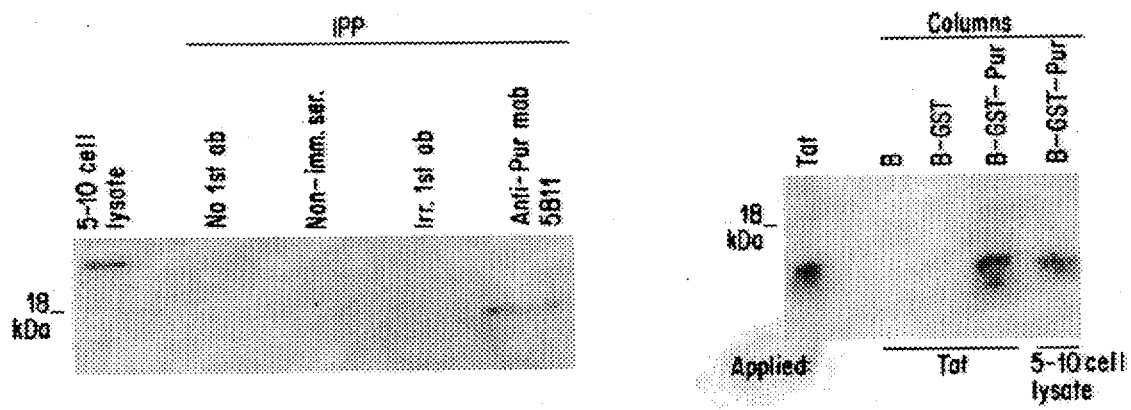

FIG. 20A. Detection of a Tat-Purα complex in human glioblastoma cells expressing the HIV-1 tat gene. Glioblastoma cell line 5–10, constitutively synthesizing Tat expressed under control of the SV40 late promoter, was cultured in 75 cm$^2$ plates to 5×10$^5$ cells per plate. The left lane represents 25 μL of untreated lysate. For the lanes labeled IPP, immunoprecipitation was carried out using magnetic beads alone (No first antibody), mouse non-immune serum (Non-imm. ser.), an irrelevant first antibody, anti-influenza virus hemagglutinin epitope monoclonal antibody 12CA5 (Irr. 1st ab) or anti-Purα antibody 5B11 (Anti-Pur mab 5B11).

FIG. 20B. Complex formation between Tat and GST-Purα in glioblastoma cell lysates. The left lane represents purified Tat protein (400 ng.) Lanes labeled Columns represent protein eluted from columns consisting of beads alone (B), Beads coupled to GST (B-GST) or beads coupled to GST-Purα (B-GST-Pur). For the lanes labeled Tat 400 ng of purified Tat protein were passed over the column. For the lane labeled 5–10 cell lysate, 20 μL of clarified lysate were passed over the column. The four lanes at left were exposed to film for equal time, and the lane at far right 20 times longer. The position 18 kDa represents migration of a prestained lysozyme marker.

Figure 21A:
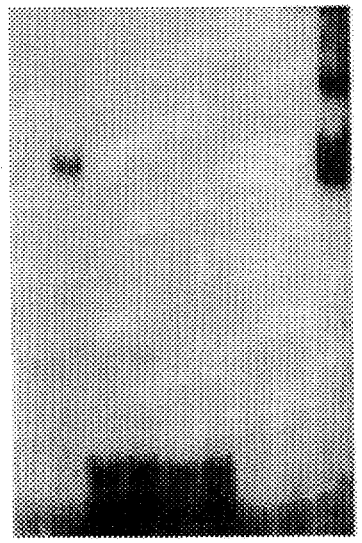

FIG. 21A. Specificity of binding of Purα to the JCV upTAR element. The different oligonucleotide probes used for the indicated reactions are: JCV+, the purine-rich single strand of the upTAR element; JCV ds, the double-stranded upTAR element, only the pyrimidine-rich strand of which is labeled; JCV−, the pyrimidine-rich strand of the upTAR element.

Figure 21B:
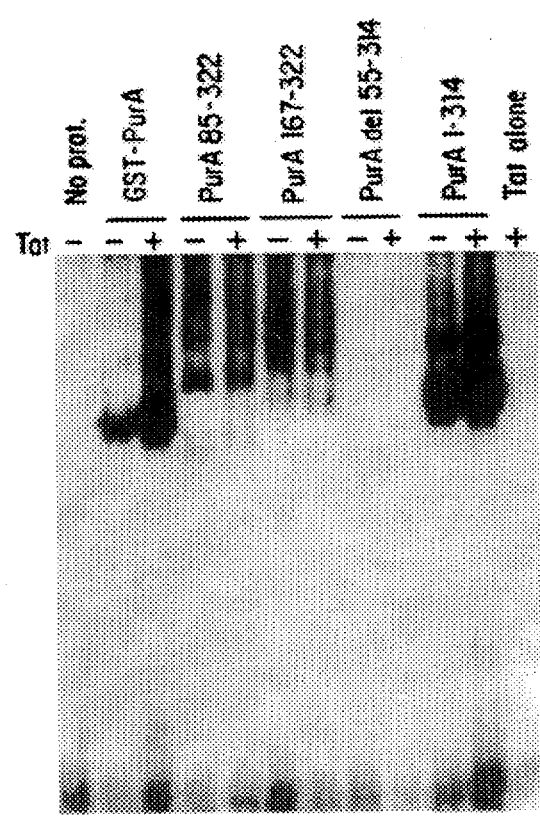

FIG. 21B. Effect of Tat upon binding of a series of Purα deletion mutants to the JCV upTAR element. Tat refers to GST-Tat. GST-PurA refers to full-length GST-Purα, in which Purα is 322 aa long. Numbers given for deletion mutants refer to the Purα aa's remaining in the construct, beginning with the N-terminus of Purα, except for PurA del 55-314, in which the indicated internal aa's have been deleted.

Figure 22A:
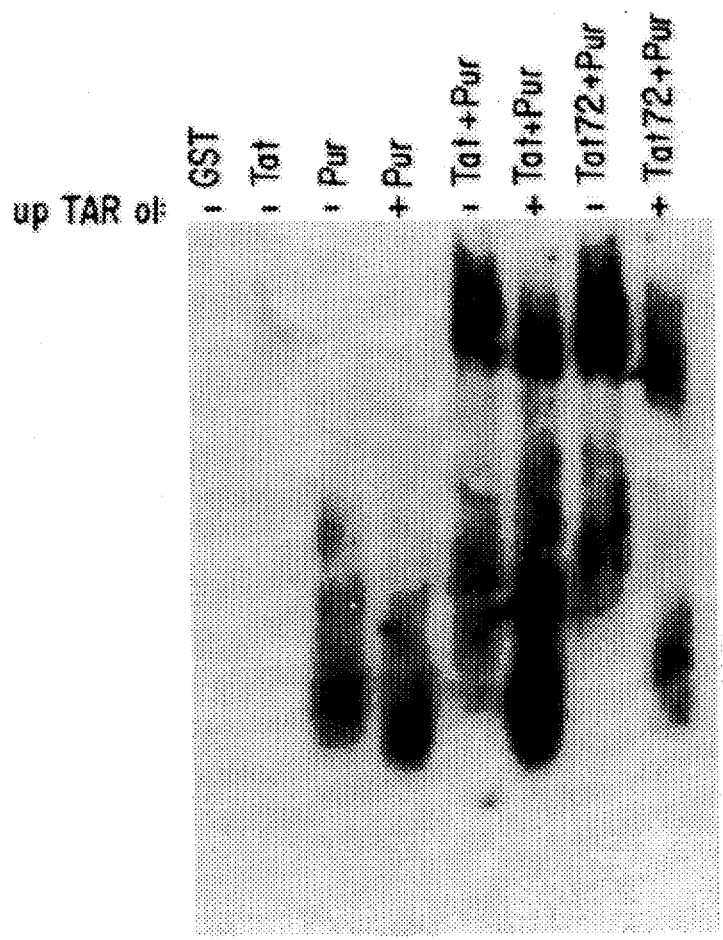
Figure 22B:
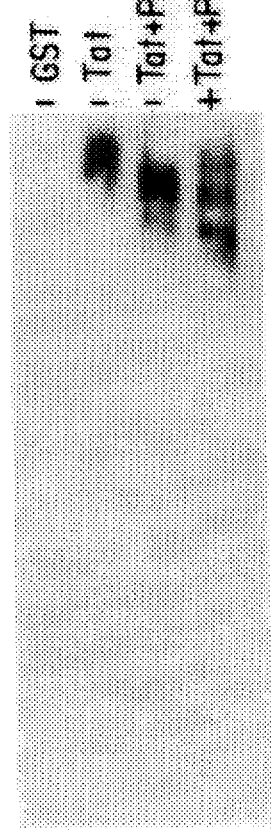

FIG. 22. Association of Tat and Purα proteins in the presence or absence of the JCV upTAR element. Binding of labeled upTAR indicates the position of GST-Purα on the filter. The right portion filter, containing lanes run in parallel to those on the left, was probed with rabbit anti-Tat antibody 705, as described for FIG. 20 to indicate the position of Tat.

Figure 23:
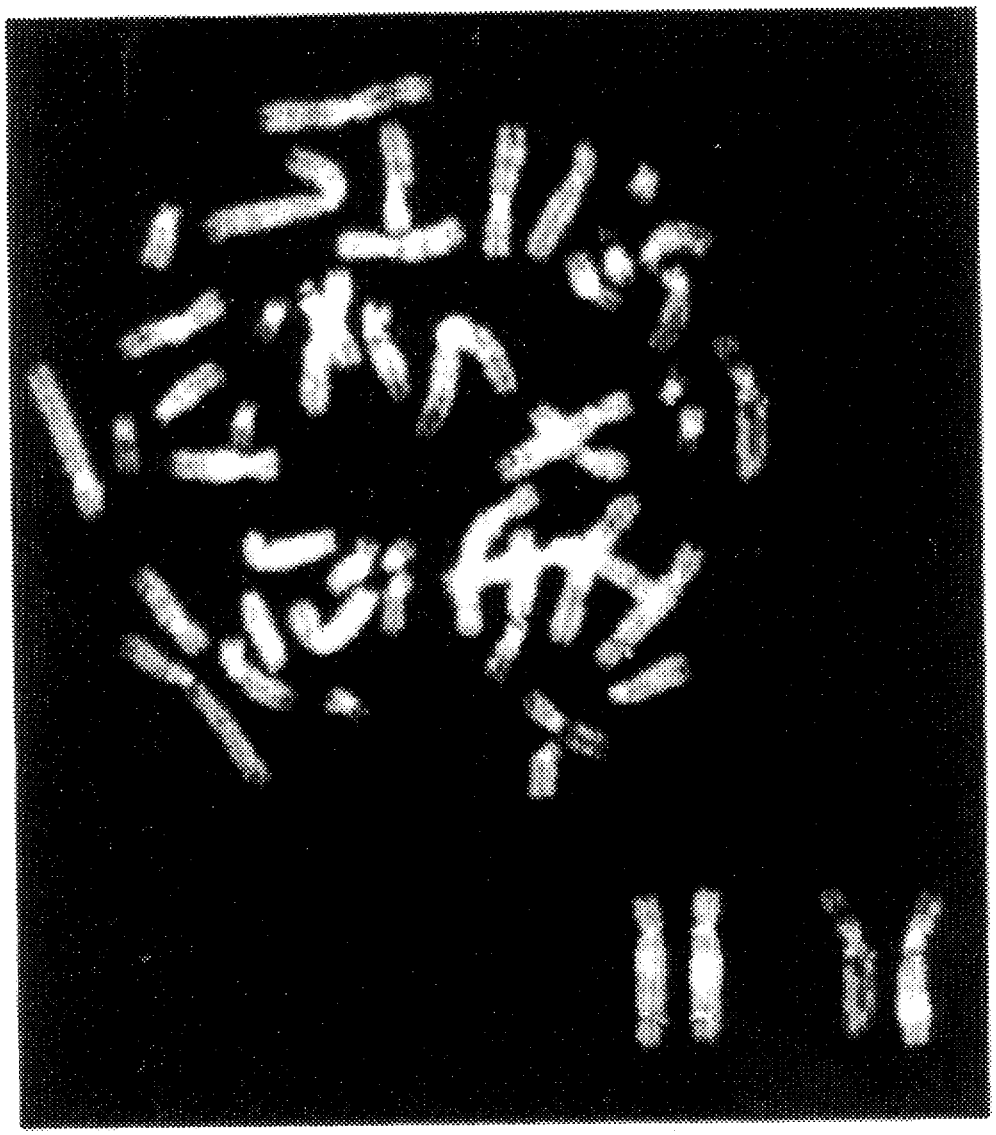

FIG. 23. Fluorescence image of a metaphase chromosome spread hybridized with a human purα genomic probe. FITC fluorescence from the hybridization probe has been pseudo-colored red for best photographic contrast. Isolated chromosomes 5 and 6 with hybridization signals are shown at the bottom on the right. The chromosomes are counterstained with DAPI.

Figure 24:
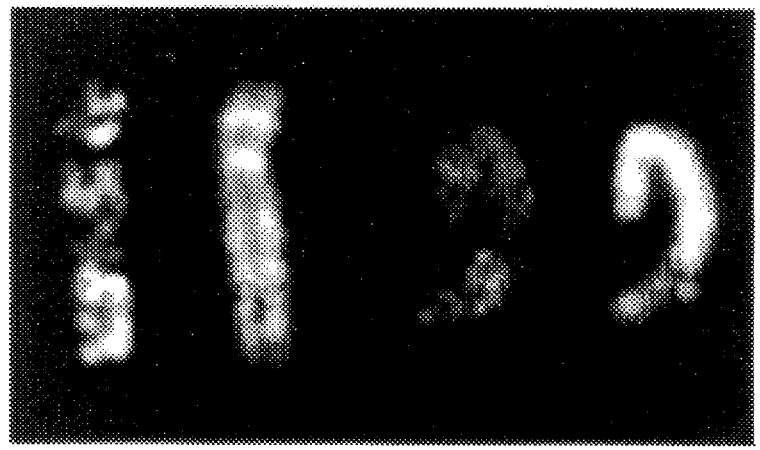

FIG. 24. Double-label fluorescence image of a chromosome 5 homologous pair. Green-yellow signal denotes R-like banding generated by cohybridization in situ with Alu repeat sequences, and red signal denotes hybridization loci of purα at 5q31. Genomic clone EMhPur 1 was used as a probe for purα. Each chromosome is counterstained with DAPI (blue). FITC and rhodamine images were recorded sequentially and subsequently aligned and merged as previously described using image-processing programs Gene Join Layer and Gene Join Maxpix.

Figure 25A:
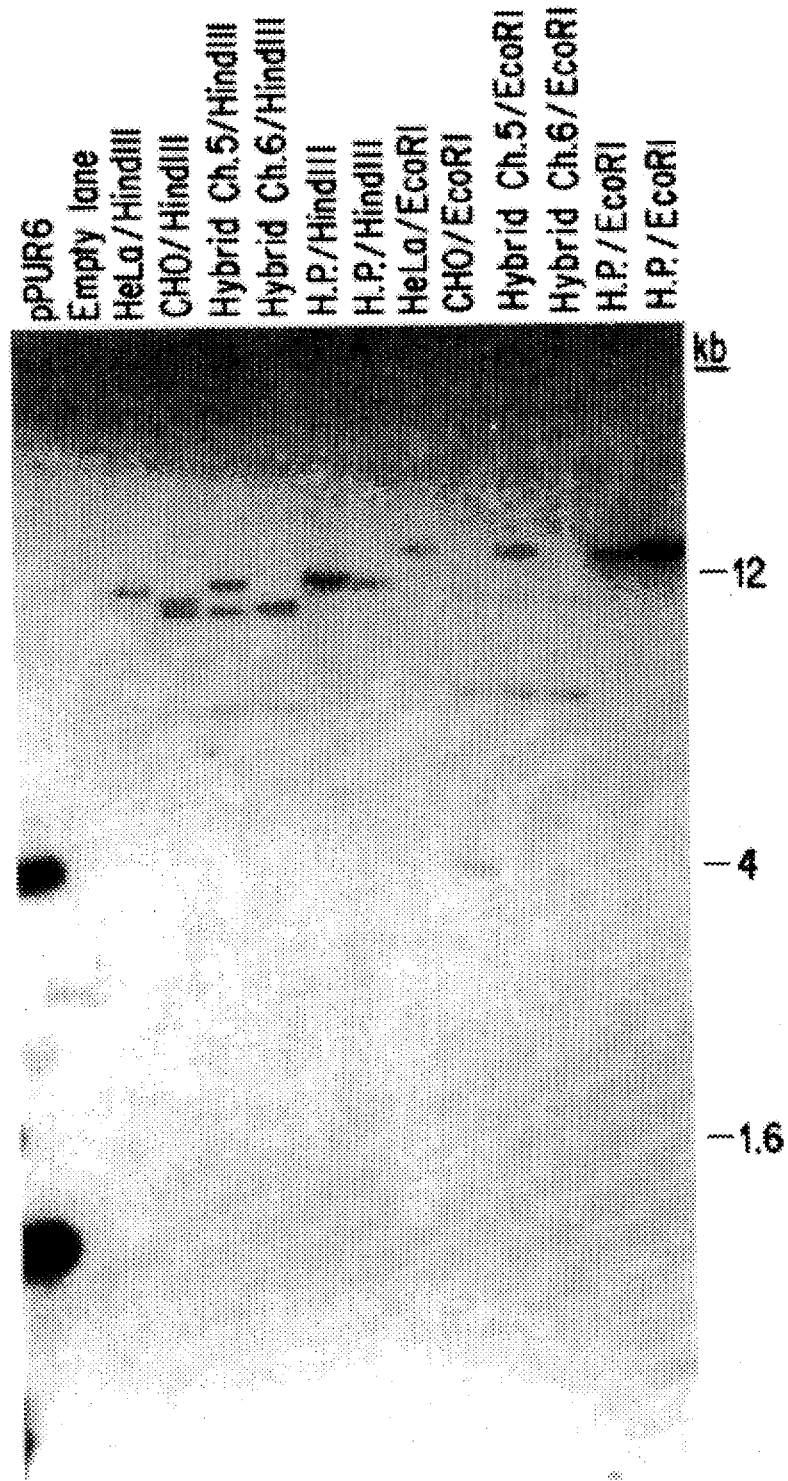

FIG. 25A. Localization of pur to human chromosome 5 by hybridization of cDNA fragment to DNA of two human/hamster hybrid cell lines containing individual chromosomes 5 or 6. DNA was prepared from hybrid cell lines NA10114, bearing human chromosome 5, and NA111580, bearing human chromosome 6, treated with restriction enzymes HindIII (lanes at left) or Eco RI (lanes at right), subjected to agarose gel electrophoresis alongside control DNAs, blotted and hybridized. The probe was a 777 bp PstI fragment of Purα cDNA, pPUR6, labeled with $^{32}$P-phosphate. Hybridization was for 16 hrs at 68°–36° C. with the following washes: 2× for 30 min. at 22° C. in 2× SSC (0.3M NaCl, 0.03M sodium citrate), 1.0% SDS, pH 7.0; 2× for 30 min at 60° C. in 1× SSC; 2× for 30 min at 22° C. in 0.1× SSC. Autoradiography employed Kodak Xomat AR film. The hamster control DNA was from Chinese hamster ovary (CHO) cells. Human control DNAs were from HeLa cells and from human placenta (H.P.). Undigested plasmid pPUR6DNA is shown at left. Markers, not shown, were the Gibco-BRL 1 kb ladder.

Figure 25B:

FIG. 25B. Restriction map of the pur locus at 5q31. The following enzymes are shown: H=HindIII; B=Bam HI; E=EcoRI; P=PstI; N=NotI. The position of the purα gene is indicated by a box. The 777 bp PstI fragment of the cDNA, representing 259 of the 322 Purα amino acids, contains no introns and is indicated by a solid box. The cDNA is oriented as shown, 5' to 3' indicating the direction of the transcription. The 11.5 kb HindIII fragment of γ phage EMhPur1, used as probe for FIGS. 1 and 2, and the 777 bp PstI fragment of plasmid pPUR6, used as probe for FIG. 30A, are shown at bottom.

5. DETAILED DESCRIPTION

A purine rich 24 nucleotide DNA sequence, referred to as the PUR element, is believed to play a role in initiation of DNA replication and regulation of gene expression. The PUR element occurs at a major site of DNA bending located 1.6 kB upstream of the transcription start site of the human c-myc gene, near the center of a reported zone of initiation of DNA replication.

The PUR protein, a 27 kD HeLa cell nuclear factor, was initially identified by its ability to bind in a sequence specific manner to single-stranded PUR element nucleotide sequences indicating a role for PUR protein in DNA replication and/or regulation of gene expression. A cDNA clone encoding a polypeptide with PUR element binding activity has been isolated and sequenced and that clone is described herein.

The invention involves the expression of PUR, or fragments thereof, to evaluate and screen for drugs that may regulate the activity of PUR. Such regulators of PUR may be used therapeutically to treat hyperproliferative diseases such as cancers. Alternatively, regulators of PUR may be used to treat viral disease where activation of viral gene expression is regulated by PUR.

The invention is based on results indicating that the PUR protein binds specifically and with high affinity to the HIV encoded transcriptional activator protein (Tat). The Tat protein transactivates transcription from the HIV-1 LTR promoter and is required for viral replication. In addition, the JC virus (JCV) contains a DNA sequence in the late promoter region that binds the Tat-Purα complex thereby indicating a role for PURα in regulation of viral transcription.

The present invention also relates to the use of PUR DNA or PUR antibodies for diagnostic purposes to detect aberrant expression of the PUR protein and/or mutations in the PUR gene. This aspect of the invention is based on in situ hybridization studies that localize the PURα gene to chromosome 5 in the 5q31 region. Loss of heterozygosity at 5q31 is frequently associated with myelodysplastic syndrome and, particularly, with myeloid leukemias. Therefore, the diagnostic methods of the invention may be utilized to detect proliferative disorders.

The present invention also relates to methods of treating proliferative disorders, such as leukemias, where gene therapy may be utilized to compensate for loss of PUR activity. Such gene therapies may, for example, utilize liposomes containing PUR protein for delivery of PUR to target tissues. Alternatively, recombinant viral vectors may be generated to express PUR protein in targeted tissues.

5.1. THE PUR ELEMENT

Bending of DNA is a structural feature conserved at origins of replication in both eukaryotic and prokaryotic organisms. A major site of DNA bending is located 1.6 kB upstream of the transcription start site of the human c-myc gene. Gel-band shift assays and DNA methylation interference assays have more precisely defined the nucleotide sequences in this region of DNA that are important for DNA/protein interactions. This region of DNA is referred to as the PUR element and has the following nucleotide sequence (SEQ ID NO:20): GGAGGTGGTGGAGG-GAGAGAAAAG.

A search of the GenBank nucleotide sequence data base for homologies to the 24 nucleotide c-myc PUR element reveals matches within previously identified zones of DNA replication (Table I). In addition, there are matches within the 5' regions of a number of cellular genes including the frequently amplified oncogenes c-myc, int-2, and lck suggesting that the PUR element may not only function during initiation of DNA replication but also in regulation of gene expression.

A role for the PUR element in initiation of DNA replication is supported by the examples detailed infra (Section 6.1.5 and 6.2.8.) in which the onset of cellular DNA replication is delayed in the presence of degenerate S-oligonucleotides designed to mimic the PUR element. Growth arrested human fibroblast, stimulated to proliferate by addition of fresh serum, were exposed to either PUR specific oligonucleotides or non-specific oligonucleotides. The incorporation of $^3$H-thymidine into newly synthesized DNA was measured and results indicate a delay in the onset of DNA replication in those cells exposed to PUR specific oligonucleotides (FIG. 16).

TABLE 1

Conservation of the PUR element at eukaryotic origins of
DNA replication and upstream promoter regions[a]

| Gene | Sequence | Location |
|---|---|---|
| c-myc gene, human (SEQ ID NO: 21) | <u>GG</u>TGGAGGGAGAGAAA | In 5' flanking sequences, within replication initiation zone |
| c-myc gene, mouse (SEQ ID NO: 22) | GGGGAAGGGAGAAAGA | In 5' flanking sequences |
| N-myc gene, human[b] and mouse (SEQ ID NO: 23) | GGGGGAGGGAGAAAGG | In 5' flanking sequences |
| dhfr gene, hamster[b] (SEQ ID NO: 24) | GGGAGAGGGAGAAGGG | In 3' flanking sequences, within replication initiation zone |
| int-2 proto-oncogene, human[b] (SEQ ID NO: 25) | GGGAGAGGGAGAGGGA | In 5' flanking sequences |
| lck proto-oncogene, human (SEQ ID NO: 26) | GGCAGAGGGAGAGGGA | In 5' flanking sequences |
| Histone H4 gene, human (SEQ ID NO: 27) | GGAGGAGGGAGAGGAA | In 5' flanking sequences, within region hypersensitive to S1 nuclease during S phase |
| β-Globin gene, human (SEQ ID NO: 28) | GGAGCAGGGAGGGCAG | In 5' flanking sequences |
| C2G1 ARS, yeast (SEQ ID NO: 29) | GGACGAGTGAGTTGGA | In origin of replication, chromosome III |
| Tubulin gene Stylonychia[b] (SEQ ID NO: 30) | AGGTGAGGGAGAAGAA | In 3' flanking sequences, at origin of replication of genome fragment |
| Direct repeat, Entamoeba (SEQ ID NO: 31) | AGGGGAGAGAGATAAT | In region displaying ARS activity |
| PUR consensus (SEQ ID NO: 32) | GGNNGAGGGAGARRRR | |

[a]The GenBank nucleotide sequence data base screened by using the 24-nucleotide sequence of MF0677. Numerous homologies were found to a 16-bp element within this sequence. Twelve of the best homologies are presented along with a 16-bp consensus element. Underlining indicates conserved nucleotides.
[b]Sequences in chromosome regions or segments for which selective amplification has been reported.

5.2. THE PUR PROTEIN

The PUR protein was initially identified as a 27 kD HeLa cell nuclear factor that bound in a sequence specific manner to single-stranded PUR element nucleotide sequences. A function for PUR protein in DNA replication and/or gene expression is indicated by the binding of PUR protein to specific regions of DNA involved in initiation of DNA replication and/or regulation of gene expression. In addition, a function for PUR in regulation of viral gene expression is indicated by the association between PUR and the HIV transactivating Tat protein. The Tat-PUR complex is also found bound to viral Tat responsive expression elements.

5.2.1. ISOLATION AND CLONING OF PUR DNA

A cDNA clone encoding a polypeptide with PUR binding activity has been isolated and sequenced. The nucleotide coding sequence and deduced amino acid sequence of the human PUR protein is depicted in FIG. 10. In accordance with the invention, the nucleotide coding sequence for human PUR protein or its functional equivalent can be used to generate recombinant molecules which direct the expression of the PUR protein. The coding sequence of PUR may be obtained by cDNA cloning of RNA isolated and purified from cell sources that express PUR protein or by genomic cloning. cDNA libraries of clones may be prepared from DNA fragments generated using techniques known in the art, including but not limited to use of restriction enzymes.

The clones that contain the gene for PUR may be identified in a number of ways know in the art. For example, a portion of the PUR amino acid sequence can be used to deduce nucleotide sequence. The DNA sequence may then be chemically synthesized, radioactively end-labeled and used as a hybridization probe. Other methods which can be used include but are not limited to chemically synthesizing the gene sequence from derived amino acid sequence of PUR. Alternatively, in-vitro translation of selected mRNA followed by a functional or immunological assay of translation products can be used. For a review of cloning strategies which may be used, see, e.g., Maniatis, 1989, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y.

In a specific embodiment described herein, the PUR gene was cloned by constructing a cDNA library into the bacteriophage expression system λgt11. The library was screened with radioactively labeled oligonucleotide MF0677 representing sequences found in the core of the PUR element. A PUR cDNA clone, designated PUR, was isolated and used to characterize PUR RNA and the PUR gene.

In accordance with the invention, nucleotide PUR sequences which encode PUR, peptide fragments of PUR, PUR fusion proteins or functional equivalents thereof may be used to generate recombinant DNA molecules that direct the expression of the PUR protein or a functionally active peptide, fusion protein or functional equivalent thereof, in appropriate host cells.

Due to the inherent degeneracy of the genetic code, other DNA sequences which encode substantially the same or a functionally equivalent amino acid sequence, e.g., shown in FIG. 10, may be used in the practice of the invention for the cloning and expression of the PUR protein. Such DNA sequences include those which are capable of hybridizing to the PUR sequence under stringent conditions, or those which would be capable of hybridizing under stringent conditions but for the degeneracy of the genetic code. The stringency conditions may be adjusted in a number of ways. For example, when performing polymerase chain reactions (PCR), the temperature at which annealing of primers to template takes place or the concentration of $MgCl^2$ in the reaction buffer may be adjusted. When using radioactively labeled DNA fragments or oligonucleotides in hybridization reactions, the stringency may be adjusted by changes in the ionic strength of the wash solutions or by careful control of the temperature at which the washes are carried out.

Altered nucleotide sequences which may be used in accordance with the invention include deletions, additions or substitutions of different nucleotides resulting in a sequence that encodes the same or a functionally equivalent gene product. The gene product may contain deletions, additions or substitutions of amino acid residues within the sequence which result in silent changes thus producing a bioactive product. Such amino acid substitutions may be made on the basis of similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine; glycine, alanine; asparagine, glutamine; serine, threonine; phenylalanine, tyrosine. As used herein, a functionally equivalent PUR protein refers to a peptide, polypeptide, protein or fusion protein that binds to the PUR element, but not necessarily with the same binding affinity of its counterpart native PUR protein. The design and engineering of constructs encoding PUR fusion proteins is described infra (Section 5.2.2.)

In an alternate embodiment of the invention, the coding sequence of the PUR protein could be synthesized, in whole or in part, using chemical methods well known in the art. See, for example, Caruthers, et al., 1980, Nuc. Acids. Res. Symp. Ser. 7: 215–233; Crea & Itrin, 1980, Nuc. Acids. Res. 9(10): 2331; Matteucci a Caruthers, 1980, Tetrahedron Letters 21: 719; and Chow & Kempe, 1981, Nuc. Acids. Res. 9(12): 2807–2817. Alternatively, the protein itself could be produced using chemical methods to synthesize the PUR protein amino acid sequence in whole or in part. For example, peptides can be synthesized by solid phase techniques, cleaved from the resin and purified by preparative high performance liquid chromatography. (E.q., see Creighton, 1983, Proteins, Structures And Molecular Principles, W. H. Freeman & Co., N.Y., pp. 50–60). The composition of the synthetic peptides may be confirmed by amino acid analysis or sequencing (e.q., the Edman degradation procedure; see Creighton, 1983, Proteins, Structures And Molecular Principles, W. H. Freeman & Co., New York, pp. 34–49).

The PURα cDNA can be used as a probe to detect the expression of PUR RNA. Northern blot analysis using mRNA prepared from human fetal liver tissue, HeLa cells, NCI-H82 cells and HepG2 cells reveal a similar pattern of multiple transcripts. Two major transcripts of 5.5 kB and 2.1 kB, and two minor transcripts of 3.3 kB and 2.8 kB were detected suggesting alternative splicing of a single PUR gene or the existence of a number of related genes.

The PURα cDNA sequence may be used to isolate PURα related genes. In a specific embodiment, a HeLa cell cDNA library was screened with a radioactively end-labeled fragment of the PUR cDNA clone. A number of clones were isolated, and one in particular was chosen for further sequence analysis. The clone, designated PUR-β, was found to be similar but not identical to the initially purified PUR cDNA clone demonstrating the existence of a family of related PUR proteins (FIGS. 11 and 12).

5.2.2. CONSTRUCTION OF EXPRESSION VECTORS CONTAINING THE PUR CODING SEQUENCE

In order to express a biologically active PUR protein, the nucleotide sequence coding for the PUR protein, or a functional equivalent including PUR fusion proteins, as described in Section 5.2.1, supra, is inserted into an appropriate expression vector, i.e., a vector which contains the necessary elements for the transcription and translation of the inserted coding sequences. Methods which are well known to those skilled in the art can be used to construct expression vectors containing the PUR protein coding sequence operatively associated with appropriate transcriptional/translational control signals. These methods include in vitro recombinant DNA techniques, synthetic techniques, and in vivo recombination/genetic recombination. See, for example, the techniques described in Maniatis, et al., 1989, Molecular Cloning, A Laboratory Manual, Cold Spring Harbor Laboratory, N.Y. and Ausubel et al., 1989, Current Protocolsin Molecular Biology, Greene Publishing Associates & Wiley Interscience, New York.

A variety of host expression vector systems (i.e.—vectors which contain the necessary elements for directing the replication, transcription, and translation of PUR coding sequence) may be utilized equally well by those skilled in the art, to express PUR coding sequences. These include but are not limited to microorganisms such as bacteria transformed with recombinant bacteriophage DNA, plasmid DNA or cosmid DNA expression vectors containing the PUR coding sequence; yeast transformed with recombinant yeast expression vectors containing the PUR coding sequence; insect cell systems infected with recombinant virus expression vectors (e.q., baculovirus) containing the PUR coding sequence; plant cell systems infected with recombinant virus expression vectors (e.g., cauliflower mosaic virus CaMV; tobacco mosaic virus, TMV) or transformed with recombinant plasmid expression vectors (e.q., Ti plasmid) containing the PUR coding sequence; or animal cell systems infected with recombinant virus expression vectors (e.g., adenovirus, vaccinia virus) including cell lines engineered to contain multiple copies of the PUR DNA either stably amplified (e.q., CHO/dhfr) or unstably amplified in double-minute chromosomes (e.g., murine cell lines).

The expression elements of these vectors vary in their strength and specificities. Depending on the host/vector system utilized, any one of a number of suitable transcription and translation elements may be used. For instance, when cloning in mammalian cell systems, promoters isolated from the genome of mammalian cells, (e.q., mouse metallothionine promoter) or from viruses that grow in these cells, (e.q., vaccinia virus 7.5K promoter or Moloney murine sarcoma virus long terminal repeat) may be used. Promoters produced by recombinant DNA or synthetic techniques may also be used to provide for transcription of the inserted sequences.

Specific initiation signals are also required for sufficient translation of inserted protein coding sequences. These signals include the ATG initiation codon and adjacent sequences. In cases where the entire PUR gene including its own initiation codon and adjacent sequences are inserted into the appropriate expression vectors, no additional translational control signals may be needed. However, in cases where only a portion of the coding sequence is inserted, exogenous translational control signals, including the ATG initiation codon must be provided. Furthermore, the initiation codon must be in phase with the reading frame of the PUR coding sequences to ensure translation of the entire insert. These exogenous translational control signals and initiation codons can be of a variety of origins, both natural and synthetic. The efficiency of expression may be enhanced by the inclusion of transcription attenuation sequences, enhancer elements, etc.

For example, in cases where an adenovirus is used as an expression vector, the PUR coding sequence may be ligated to an adenovirus transcription/translation control complex, e.q., the late promoter and tripartite ladder sequence. This chimeric gene may then be inserted in the adenovirus genome by in vitro or in vivo recombination. Insertion in a non-essential region of the viral genome (e.g., region E3 or E4) will result in a recombinant virus that is viable and capable of expressing PUR in infected hosts. Similarly, the vaccinia 7.5K promoter may be used.

An alternative expression system which could be used to express PUR is an insect system. In one such system, Autographa californica nuclear polyhidrosis virus (AcNPV) is used as a vector to express foreign genes. The virus grows in Spodoptera frugiperda cells. The PUR coding sequence may be cloned into non-essential regions (for example the polyhedrin gene) of the virus and placed under control of an AcNPV promoter (for example the polyhedrin promoter).

Successful insertion of the PUR coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed.

Retroviral vectors prepared in amphotropic packaging cell lines permit high efficiency expression in numerous cells types. This method allows one to assess cell-type specific processing, regulation or function of the inserted protein coding sequence.

In addition, a host cell strain may be chosen which modulates the expression of the inserted sequences, or modifies and processes the gene product in the specific fashion desired. Expression from certain promotes can be elevated in the presence of certain inducers. (e.g., zinc and cadmium ions for metallothionein promoters). Therefore, expression of the genetically engineered PUR may be controlled. This is important if the protein product of the cloned foreign gene is lethal to host cells. Furthermore, modifications (e.g., phosphorylation) and processing (e.g., cleavage) of protein products are important for the function of the protein. Different host cells have characteristic and specific mechanisms for the post-translational processing and modification of protein. Appropriate cell lines or host systems can be chosen to ensure the correct modification and processing of the foreign protein expressed.

Fusion protein vectors may be used to express PUR fusion protein. The purified PUR fusion protein may be used to raise antisera against the PUR protein to study the biochemical properties of the PUR protein and/or to engineer PUR fusion proteins with different binding affinities for the PUR element, and/or for the pRB protein. Possible expression vectors include but are not limited to, vectors that express β-galactosidase and trpE fusions, maltose-binding protein fusions and glutathione-S-transferase fusions (carrier regions). Methods which are well known to those skilled in the art can be used to construct expression vectors containing PUR protein coding sequences. See, e.q., Maniatis, 1989, Molecular Cloning, A Laboratory Manual, Cold Spring Harbor Press, New York; and Ausubel et al., 1989, Current Protocols in Molecular Biology, Green Publishing Associates and Wiley Interscience, New York.

The carrier region of the fusion protein may be used for purification of the PUR fusion protein. For example, antibodies against the carrier protein may be used in affinity chromatography for purification of the fusion protein. Alternatively, amylose resin may be used for purification of maltose binding protein fusions or glutathione-agarose beads may be used for purification of glutathione-S-transferase fusion proteins. The expression vectors may also contain polylinker sequences that encode specific protease cleavage sites so that any cloned protein may be released from its carrier protein by treatment with a specific protease. For example, DNA sequences encoding the thrombin or factor Xa cleavage sites may be included in the fusion protein vectors.

In a specific embodiment described herein, the PUR coding sequence was inserted into the pGEX-1λT expression vector containing the tac IPTG inducible promoter region and the coding region for the amino terminus of glutathione-S-transferase. After induction with IPTG, the GST-PUR fusion protein was purified from lysed cells using glutathione-linked garose beads.

The role of PUR in DNA replication and transcriptional regulation indicates that nuclear localization is essential for PUR function. In addition, the coding region of PUR protein, or fragments thereof, may be linked to DNA sequences encoding nuclear localization sequences (NLS). In most cases the NLS consists either of a short division of basic amino acids, for example as shown for the NLS of SV40 T antigen (SEQ ID NO:33) (PKKKRKV). Alternatively, the NLS may have a bipartite structure comprised of two stretches of basic residues separated by a spacer of about 10 amino acids. (Dingwell et al., 1991, Trends Biochem. Sci. 16:478). In the practice of the invention, any NLS sequences that functions to direct the localization of PUR to the nucleus may be incorporated into PUR expression vectors. Inclusion of these signals in PUR expression vectors will ensure that recombinantly expressed PUR protein, fragments of PUR proteins, or PUR fusion proteins are properly localized to the nucleus. Such nuclear localization signals are well known to those skilled in the art and may be genetically engineered into PUR expression vectors using routine methods.

5.2.3. IDENTIFICATION OF TRANSFECTANTS OR TRANSFORMANTS EXPRESSING THE PUR GENE PRODUCT

The host cells which contain the recombinant PUR coding sequence and which express the biologically active, mature product may be identified by at least four general approaches: (a) DNA-DNA, DNA-RNA or RNA-antisense RNA hybridization; (b) the presence or absence of "marker" gene functions; (c) assessing the level of transcription as measured by the expression of PUR mRNA transcripts in the host cell; and (d) detection of the mature gene product as measured by immunoassay and, ultimately, by its biological activity.

In the first approach, the presence of the human PUR coding sequence inserted in the expression vector can be detected by DNA-DNA hybridization using probes comprising nucleotide sequences that are homologous to the human PUR coding sequence.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the PUR coding sequence is inserted within a market gene sequence of the vector, recombinants containing the PUR coding sequence can be identified by the absence of the marker gene function. Alternatively, a marker gene can be place in tandem with the PUR sequence under the control of the same or different promoter used to control the expression of the PUR coding sequence. Expression of the marker in response to induction or selection indicates expression of the PUR coding sequence.

In the third approach, transcriptional activity of the PUR coding region can be assessed by hybridization assays. For example, polyadenylated RNA can be isolated and analyzed by Northern blot using a probe homologous to the PUR coding sequence or particular portions thereof. Alternatively, total nucleic acids of the host cell may be extracted and assayed for hybridization in such probes.

In the fourth approach, the expression of the mature protein product can be assessed immunologically, for example by Western blots, immunoassays such as radioimmuno-precipitation, enzyme-linked immunoassays and the like. The ultimate test of the success of the expression system, however, involves the detection of the biologically active PUR gene product. One of the properties associated with PUR protein is its sequence specific affinity for the PUR element. A possible method for detection of PUR protein activity might involve the use of gel-band shift assays.

5.2.4. THE PUR PROTEIN

The PUR protein was initially characterized as a factor present in HeLa cell nuclear extracts, that bound in a sequence specific manner to single- stranded PUR element sequence. Screening of a λgt11 expression library, with radioactively end-labeled PUR element sequences, represented by the oligonucleotide MF0677, resulted in the isolation of a cDNA clone encoding a protein with single-stranded binding activity matching that of the PUR factor.

The deduced amino acid sequence of PUR reveals a modular repeat structure unique among known DNA-binding proteins. There are three repeats of a 23 amino-acid motif (class I repeats) interspersed with two repeats of a 26 amino-acid motif (class II repeats). The class I repeats are shown by single underlining in the sequence of FIG. 10, and the class II repeats are shown by double underlining. While the sequence between these repeats is not conserved, the distance between the class I repeats is highly regular. The repeats themselves are not identical but preserve a number of strictly conserved amino acids of fixed distances along the repeats, indicated by solid boxing in FIG. 11, and a high percentage of conservatively-substituted amino acids, indicated by dotted-line boxing in FIG. 11.

In addition to repeat modules, PURα contains several notable structural features denoted in FIG. 12A. Near the amino-terminal end of PURα there is a prominent sequence of 28 glycine residues broken only by a single serine residue. Similar glycine stretches are present in proteins serving a wide variety of functions, including helix-destabilizing proteins (Haynes et al., 1987 Proc. Natl. Acad. Sci. US 79:4083–4087). Carboxyl terminal to all of the repeat modules there is a region (residues 261 through 274) of alpha helix (Chou and Fasman, 1974 Biochemistry 13:222–245; Levin et al., 1986 FEBS Lett. 205:303–308) upon which the amino acid side chains confer a strongly amphipathic character. The amphipathic helix is ordered with opposing basic and aromatic side chains, as presented in the helical wheel of FIG. 12B. Similar amphipathic helices are present in several DNA-binding proteins thought to play a role in transcriptional activation (Ptashne, 1988, Nature 335:683–689). The carboxyl terminus of the PUR molecule consists of glutamine-glutamate-rich domain. The entire sequence from residue 276 through 321 is 50% glutamine and glutamate residues. There is one sequence of 7 consecutive glutamine residues, and near the carboxyl terminus there is a sequence of 5 glutamate residues broken by a single glycine. Glutamine-rich domains have been implicated as transcriptional activation regions in several DNA-binding proteins (Courey et al., 1989, Cell 59:827–836). At the border between the amphipathic helix and the glutamine-glutamate-rich domain there is the motif Ser-Glu-Glu-Met (residues 275 through 278). The serine in this motif is a potential phosphorylation site for casein kinase II (Kennelly and Krebs, 1991, J. Biol. chem. 266:15555–15558), although it is not known whether the motif serves this function in Purα.

5.2.5. THE PUR PROTEIN BINDS THE RETINOBLASTOMA GENE PRODUCT (pRB)

The PURα molecule shares a region of protein homology with the DNA tumor virus protein SV40 large T-antigen (FIG. 17). The region of SV40 T-antigen, sharing homology with PURα, is of particular interest as it is the region of T-antigen involved in the protein/protein interaction between SV40 large T-antigen and the retinoblastoma (pRB) gene product.

Experiments were done to examine whether PURα could function as SV40 large T-antigen and bind to pRB protein. A PUR-GST protein was expressed in E. coli followed by immobilization of the fusion protein on a glutathione-linked agarose column. WR2E3 cell extracts were passed over the PUR-GST column and bound proteins were eluted with excess glutathione. The eluted proteins were subjected to SDS polyacrylamide gel electrophoresis and blotted onto nitrocellulose membrane. The presence of pRB protein was detected using anti-Rb antibodies. As illustrated in FIG. 17, the PUR-GST fusion protein is able to bind cellular pRB with the same affinity as SV40 large T-antigen. In addition, the PUR-GST fusion protein seems to preferentially bind the unphosphorylated form of pRB.

5.2.6. A ROLE FOR PUR IN REGULATION OF VIRAL GENE EXPRESSION

As demonstrated in the working examples presented in Section 8.2., a Tat-PURα complex can be detected in glioblastomas cells expressing the HIV-1 tat gene (FIG. 20A). Moreover, purified TAT and PURα can be shown to associate specifically and with high affinity. Analysis of PUR deletion mutants indicates that the first 72 amino acids of Tat and the first 85 amino acids of PUR are required for the Tat-PUR protein/protein interaction (FIG. 21B).

DNA binding studies strongly suggest that PURα has the ability to bind to HIV TAR sequences (FIG. 23B). In addition, transient expression assays indicate that the HIV-1 LTR promoter is induced by PURα and that HIV TAR sequences are primarily responsible for PUR induced gene expression (FIG. 25).

A purine rich element (upTAR) in the late promoter region of JCV DNA mediates transcriptional activation by the HIV-1 Tat protein, which by itself does not bind this element. The purine rich element contains recognition sites for PURα. As further demonstrated in Section 8.2., PURα binds to the purine-rich strand of the upTAR element of the JCV virus. The binding of PURα to the upTAR element is enhanced by the binding of Tat indicating a functional role for the Tat-PURα complex in the activation of viral gene expression.

5.3. INHIBITORS OF PUR PROTEIN

The specific affinity of PUR protein for DNA sequences located at origins of replication suggest that PUR protein may play a role in regulation of cell proliferation. The observed protein/protein interaction between the PUR protein and the pRB protein further supports the view that the PUR protein is involved in regulation of cell proliferation. The PUR protein also binds 5' to a number of cellular oncogenes that include c-myc, int-2 and lck, indicating that PUR may also regulate gene expression. The observed protein/protein interaction between PUR and the HIV encoded Tat protein suggests a role for PUR in regulation of viral transcription. This is further supported by the demonstration that the Tat-Purα complex binds to Tat responsive viral transcriptional elements. Inhibitors of PUR protein may function to selectively inhibit the replication and/or gene expression of specific genetic loci associated with PUR elements or viral transcriptional elements.

5.3.1. PUR ANTIBODIES

Within the scope of the invention is the production of polyclonal and monoclonal antibodies that bind PUR or PUR related proteins. Antibodies to PUR may be useful as diagnostic and therapeutic agents. More specifically, antibodies that bind PUR protein and which neutralize PUR activity may be of particular therapeutic value. For example, antibodies that bind PUR protein and in doing so, prevent PUR binding to pRB or to PUR element DNA sequences may be useful in therapies designed to inhibit cell proliferation. Alternatively, antibodies that bind PUR protein and in doing so prevent PUR from binding to HIV Tat, or Tat responsive viral transcriptional elements, may be useful in treating viral diseases.

For the production of antibodies, various host animals may be immunized by injection with the PUR protein including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and corynebacterium parvum.

Monoclonal antibodies to the PUR protein may be prepared by using any technique which provides for the production of antibody molecules by continuous cell lines in culture. These include but are not limited to the hybridoma technique originally described by Kohler and Milstein, (Nature, 1975, 256:495–497), the human B-cell hybridoma technique (Kosbor et al., 1983, Immunology Today, 4:72; Cote et al., 1983, Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci., 10 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce PUR-specific single chain antibodies.

Antibody fragments which contain specific binding sites for the PUR protein may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity to PUR protein.

5.3.2. ANTI-SENSE RNA AND RIBOZYMES

Also within the scope of the invention are oligoribonucleotide sequences, that include anti-sense RNA molecules and ribozymes that function to inhibit the translation of PUR mRNA. Anti-sense RNA molecules act to directly block the translation of mRNA by binding to targeted mRNA and preventing protein translation.

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of PUR RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Both anti-sense RNA molecules and ribozymes of the invention may be prepared by any method known in the art for the synthesis of RNA molecules. These include techniques for chemically synthesizing oligoribonucleotides well known in the art such as for example solid phase phosphoamite chemical synthesis. Alternatively, RNA molecules may be generated by in-vitro and in-vivo transcription of DNA sequences encoding the RNA molecule. Such DNA sequences may be incorporated into a wide variety of vectors which incorporate suitable RNA polymerase promoters such as the T7 or SP6 polymerase promoters.

Various modifications to the RNA molecules may be introduced as a means of increasing intracellular stability and half-life. Possible modifications include but are not limited to the addition of flanking sequences of ribo- or deoxy-nucleotides to the 5' and/or 3' ends of the molecule or the use of phosphorothioate or 2' O-methyl rather than phosphodiesterase linkages within the oligoribonucleotide backbone.

5.3.3. TRIPLEX DNA FORMATION

Oligodeoxyribonucleotides can form sequence-specific triple helices by hydrogen bonding to specific complementary sequences in duplexed DNA. Interest in triple helices has focused on the potential biological and therapeutic applications of these structures. Formation of specific triple helices may selectively inhibit the replication and/or gene expression of targeted genes by prohibiting the specific binding of functional trans-acting factors.

Included in the scope of the invention are specific deoxyribonucleotide sequences, synthesized in a DNA synthesizer, that form triple helices with the PUR consensus element (Table I). The PUR element is comprised predominantly of long repeats of G/A nucleotide sequences which are characteristic of target sequences favoring DNA triplex formation. Triple helix formation, at the site of PUR elements, may function to inhibit DNA replication and/or transcription of DNA sequences found adjacent to the element by preventing the binding of trans-acting factors such as PUR protein. Support for this is provided by experimental data demonstrating a delay in onset of DNA replication in cells exposed to PUR element oligonucleotides (FIG. 16).

5.3.4. PUR-RELATED DERIVATIVES, ANALOGUES, AND PEPTIDES

The production and use of derivatives, analogues and peptides related to PUR are also envisioned and are within the scope of the invention. Such derivatives, analogues and peptides may be used to compete with full length wild-type PUR protein for binding to the PUR consensus element and in doing so inhibit PUR protein activity. The inhibition of PUR protein function may be utilized in several applications, including but not limited to, the treatment of hyperproliferative diseases such as cancer.

Derivatives, analogues and peptides related to PUR protein may also be used to compete with full length wild type PUR protein for binding to the HIV encoded Tat protein, or Tat responsive viral transcription elements. Such inhibitors may be utilized to treat virally infected patients.

The present invention also includes methods for identifying the specific site(s) of PUR that interact with (i) PUR elements; (ii) pRB; (iii) HIV Tat; or (iv) Tat responsive viral transcriptional elements. Using the methods described herein, and biochemical and molecular biological methods well-known in the art, it is possible to identify the corresponding portions of PUR involved in these interactions. For example, site-directed mutagenesis of DNA encoding the PUR protein may be used to destroy or inhibit the interaction between the molecules and PUR.

In an embodiment of the invention, a series of deletion mutants in the PUR coding region may be constructed and analyzed to determine the minimum amino acid sequence requirements for binding to the PUR consensus element. Deletion mutants of the PUR coding sequence may be constructed using methods known in the art which include but are not limited to use of nucleases and/or restriction enzymes; site-directed mutagenesis techniques, PCR, etc. The mutated polypeptides may be assayed for their ability to bind to the PUR element by gel-band shift assays. The mutated polypeptides may be assayed for their ability to bind the virally encoded HIV Tat protein and/or the viral TAT responsive transcriptional elements.

As demonstrated in working examples presented in Section 8.2., supra, a series of PUR deletion mutants were analyzed for their effect on the binding of Tat-PURα to JVC DNA. The results indicate that when the amino-terminal 85 amino acids of PURα are removed, DNA binding is lost. A more detailed mutational analysis of PUR may be utilized to determine the minimum PURα amino acids required for Tat-PURα DNA binding.

Biophysical methods such as X-ray crystallography and nuclear magnetic resonance may also be used to map and study these sites of interaction. Once these sites have been identified, the present invention provides means for promoting or inhibiting this interaction, depending upon the desired biological outcome. Based on the foregoing, given the physical information on the sites of interaction, compounds that modulate PUR activity may be elaborated by standard methods well known in the field of rational drug design.

5.3.5. SCREENING ASSAY

Recombinantly expressed PUR protein may be used to screen for molecules that modulate PUR activity. Such molecules may include small organic or inorganic compounds, antibodies, peptides, or other molecules that modulate PUR's ability to bind to (i) PUR elements; (ii) TAT responsive viral transcriptional elements; (iii) pRB; or (iv) HIV encoded Tat protein. Synthetic compounds, natural products, and other sources of potentially biologically active materials can be screened in a number of ways.

The ability of a test molecule to modulate the activity of PUR may be measured using standard biochemical techniques, such as gel shift assays, pRB binding assays or HIV Tat binding assays. Various embodiments are described below for screening, identification and evaluation of compounds that interact with PUR protein, which compounds may affect various cellular processes under the control of the PUR protein.

The invention includes a method whereby a molecule capable of binding to PUR in a chemical or biological preparation may be identified comprising:

(a) immobilizing PUR or fragments thereof, to a solid phase matrix;
(b) contacting the chemical or biological preparation with the solid phase matrix produced in step (a), for an interval sufficient to allow the compound to bind;
(c) washing away any unbound material from the solid phase matrix;
(d) detecting the presence of the compound bound to the solid phase, thereby identifying the compound.

The above method may further include the step of:

(e) eluting the bound compound from the solid phase matrix, thereby isolating the compound.

The term "fragment thereof" refers to peptide fragments of PUR corresponding to as few as 5 contiguous amino acids. Alternatively, the peptide fragments may correspond to functon domains of the PUR protein such as those domains of the PUR protein that bind to pRB, HIV encoded Tat or Tat responsive transcriptional elements. The term "compound capable of binding to PUR" refers to a naturally occurring or synthetically produced molecule which interacts PUR. Such a compound may directly or indirectly modulate PUR activity and may include molecules that are natively associated with PUR inside a cell.

The present invention provides an assay for identifying a compound, which can block the interaction of PUR with: (i) PUR elements; (ii) pRB; (iii) HIV Tat; or (iv) Tat responsive viral transcriptional elements. For example, a cell transfected to coexpress PUR and HIV Tat in which the two proteins interact to form a complex, can be incubated with an agent suspected of being able to inhibit this interaction, and the effect on the interaction can be measured. Any of a number of means for measuring the interaction and its disruption such as coimmunoprecipitation or gel shift analysis are available. The present invention also provides an assay method to identify and test a compound which stabilizes and promotes the interaction, using the same approach described above for a potential inhibitor.

Random peptide libraries consisting of all possible combinations of amino acids may be used to identify peptides that are able to bind to the binding sites of PUR, or other functional domains of PUR. Identification of molecules that are able to bind to PUR may be accomplished by screening a peptide library with recombinant PUR proteins or recombinant soluble forms of PUR protein. Alternatively, the binding domains of PUR may be separately expressed and used to screen peptide libraries.

One way to identify and isolate the peptide that interacts and forms a complex with PUR may involve labelling or "tagging" PUR protein. The PUR proteins may be conjugated to enzymes such as alkaline phosphatase or horseradish peroxidase or to other reagents such as fluorescent labels which may include fluorescein isothyiocynate (FITC), phycoerythrin (PE) or rhodamine. Conjugation of any given label to PUR may be performed using techniques that are routine in the art. Alternatively, PUR expression vectors may be engineered to express a chimeric PUR protein containing an epitope for which a commercially available antibody exists. The epitope-specific antibody may be tagged using methods well known in the art including labeling with enzymes, fluorescent dyes or colored or magnetic beads.

The DNA sequence encoding the desired polypeptide may then be cloned into an appropriate expression vector for overexpression in either bacteria or eukaryotic cells. Peptides may be purified from cell extracts in a number of ways including but not limited to ion-exchange chromatography or affinity chromatography. Alternatively, polypeptides may be synthesized by solid phase techniques followed by cleavage from resin and purification by high performance liquid chromatography.

5.4. USES OF PUR PROTEIN AND ITS INHIBITORS

A search of the Genebank nucleotide sequence data base for homologies to the 24 nucleotide PUR element reveals a number of matches. Among the matches identified were those mapping to regions of the genome previously reported to be zones for initiation of DNA replication suggesting a role for PUR in initiation of DNA replication. Homologies were also observed in the 5' region of a number of cellular oncogenes including c-myc, int-2, and lck suggesting a potential role for PUR in regulation of gene expression. In fact, the structure of PUR protein shares a number of features in common with transactivating domains of many transcription factors and the region of PUR binding 5' to the myc gene, is a region previously reported to contain positively-acting transcriptional control elements (May et al. 1985, Genes Dev. 1:659–671). A number of factors are involved in both replication and transcription in prokaryotic, lower eukaryotic and viral systems.

Inhibitors of PUR activity may be useful for inhibiting cellular DNA replication and proliferation of specifically targeted cells. The therapeutic value of anti-PUR reagents for treatment of hyper-proliferative diseases resulting from gene amplification is supported by the association of PUR elements with regions 5' to a number of oncogenes frequently found amplified in tissue derived from tumors. For example, using Southern and/or slot blot techniques, it has been shown that int-2 is amplified in cases of T-lymphoblastic leukemias (Tycko et al., J. Exp. Med. 174:867–73). In breast cancer specimens, c-myc, int-2 and lck, have also been shown to be amplified and in one particular study in which 49 cases of breast cell carcinomas were studied a correlation between tumor progression (i.e. metastatic vs. non-metastatic) and the level of c-myc and int-2 amplification was observed (Donovan-Peluso et al., 1991, Am. J. Pathol. 138:835–45). Studies have also detected overexpression of c-myc and int-2 in tumors of the bladder, esophagus and kidney (Tsutsumi et al. 1988, Jpn J. Cancer Res, 79:428–32).

In an embodiment of the invention anti-PUR antibodies capable of neutralizing the activity of PUR protein may be used to inhibit PUR activity. Small peptide fragments representative of regions of the PUR protein that competitively bind to the PUR element or the pRB protein, and in doing so block the wild type protein from binding and carrying out its function may also be used to inhibit PUR activity. In yet another embodiment antisense or ribozyme molecules, designed on the basis of PUR DNA sequence, may be utilized to block translation and expression of PUR gene product. Finally, oligonucleotides complementary to the PUR element may be designed to form a triplex helical structure at the PUR element thereby preventing the binding of PUR protein.

5.5. DIAGNOSTIC METHODS FOR DETECTING PUR RELATED DISORDERS

The purα DNA may have a number of uses for the diagnosis of diseases resulting from mutations in the put gene, and/or aberrant expression of PUR protein. For example, the pur DNA sequence may be used in hybridization assays of biopsies or autopsies to detect mutations in the pur gene and/or abnormalities in expression of the pur gene; e.g., in situ hybridization assays, Southern or Northern analysis.

Alternatively, antibodies that bind to epitopes of the PUR protein may be utilized diagnostically to assay for abnormalities in the levels of expression of the PUR protein; e.q., in situ hybridization assays, immunoprecipitations and Western analysis.

The purα gene is represented as a single copy gene in the human genome. The chromosomal localization of the human purα gene was determined using fluorescence in-situ hybridization studies using a genomic purα probe. Results presented in Section 9.2. indicate that purα is present on chromosome 5. A more precise localization of the purα gene places the gene at 5q31. Loss of heterozygosity at 5q31 is frequently associated with myelodysplastic syndrome and, particularly, with myloid leukemias. It has been speculated that a leukemia tumor suppressor gene is located at 5q31. Extensive deletions in the 5q region are also frequently observed in lung cancer. Therefore, in a specific embodiment of the invention diagnostic methods may be used to detect chromosomal abnormalties in the region of the genome that encodes PURα.

5.6. GENE THERAPY

Also within the scope of the present invention is the use of gene therapy to replace mutated or deleted PURα with a wild type complement of the gene. As described above, a number of proliferative disorders, such a myloid leukemias and lung cancers, have deletions in the regions of the genome encoding PURα.

Methods for transferring the wild type PURα gene into the targeted tissue may include reconstitution of recombinant PURα molecules into liposomes for delivery into target cells. Alternatively, recombinant viral vectors may be engineered to express wild type PURα. Expression vectors derived from viruses such as retroviruses, vaccinia virus, adeno-associated virus, herpes virus or bovine papilloma virus, may be used to deliver wild type PUR into the targeted cell population. Methods which are well known to those skilled in the art can be used to construct recombinant viral vectors containing PURα coding sequence. See, for example, the techniques described in Maniatis et al., 1989, Molecular Cloning A Laboratory Manual, Cold Spring Harbor Laboratory, N.Y. and Ausubel et al. 1989, Current Protocols in Molecular Biology, Khune Publishing Associates and Wiley Interscience, N.Y.

6. EXAMPLE

IDENTIFICATION AND CHARACTERIZATION OF THE PUR PROTEIN AND ITS SEQUENCE ELEMENT

The subsection below describes the characterization of a sequence element, referred to as the PUR element, found 1.6 Kb upstream of the cellular c-myc gene. The PUR element is located in a region of DNA bending activity which is a structural feature frequently associated with origins of DNA replication. Also described below is the identification of a polypeptide, having a molecular weight of approximately 37,000 and referred to as the PUR protein, that binds specifically to single-stranded DNA containing the PUR element sequence.

6.1. MATERIALS AND METHODS

6.1.1. PLASMIDS AND OLIGONUCLEOTIDES USED

Plasmid pMYC47 (FIG. 1) was constructed by cloning the 467-bp Sau3A1 fragment of the c-myc upstream region into the BamHi site of pUC19 and screening for clones containing two copies of the fragment in the same orientation. The sequences of oligonucleotides used are as follows:

MF0677, (SEQ ID NO:20) GGAGGTGGTGGAGG-GAGAGAAAAG

MM0677, (SEQ ID NO:34) GGAGGTGGTGGAAAAA-GAGAAAAG

DR3529, (SEQ ID NO:35) TGATGAGGGAGAGG-GAGAAGGGAT

DF3506, (SEQ ID NO:36) ATCCCTTCTCCCTCTC-CCTCATCA

MF0562, (SEQ ID NO:37) TACTGAATTCACTTAA-CACT

MR0700, (SEQ ID NO:38) CTTTTCTCTCCCTCCAC-CACCTCC

MR0740, (SEQ ID NO:39) TCTCAAGCTTGGTCCCT-CAC

MA0677, (SEQ ID NO:40) GGAGATAGTGGAGG-GAAAGAAAAG

MB0677, (SEQ ID NO:41) GGAGATAGTAGAGG-GAGAGAAAAG

Circular permutation experiments were performed as described by Wu and Crothers (1984, Nature 308:509–513). The 973-bp EcoRI-PstI fragment of pMYC47, containing a tandem dimer of the 467-bp Sau3AI fragment shown in FIG. 1, was purified from low-melting-point agarose gels by melting at 65° C. for 10 min followed by phenol extraction and ethanol precipitation. Restriction fragments generated by digestion of the 973-bp fragment were subjected to electrophoresis in 12.5% polyacrylamide gels, using Tris-borate-EDTA (TBE) buffer at 4° C., stained with ethidium bromide, and visualized by UV irradiation.

6.1.2. GEL SHIFT ASSAYS

Nuclear extracts were prepared from HeLa cells according to the procedure of Dignam et al. (1983, Nucleic Acids Res. 11:1475–1489). Gel shift assays were performed as described by Ausubel et al. (1989, Current Protocols in Molecular Biology 2:12.2.1–12.2.10). Binding reaction mixtures contained 0.5 μg of poly(dI-dC), 4.5 μg of bovine serum albumin, 1 to 3 μg of nuclear extract protein, and 0.5 ng of oligonucleotide probe (end-labeled with T4 polynucleotide kinase and [γ-$^{32}$P] ATP to approximately 60 Ci/mmol) in a total of 20 μl of binding buffer (9 mM N-2-hydroxethylpiperazine-N'-2-ethanesulfonic acid [HEPES, pH 7.9], 9% glycerol, 45 mM KCl, 0.25 mM dithiothreitol, 0.25 mM phenylmethysulfonyl fluoride) unless specified otherwise. Binding was carried out for 15 min at 30° C. Electrophoresis was conducted in TBE buffer at 150 V for 2 h at 4° C. Gels were dried onto Schleicher & Schuell GB002 paper and autoradiographed on Kodak XAR5 film.

6.1.3. DETERMINATION OF THE MOLECULAR WEIGHT OF THE DNA-BINDING PROTEIN

The molecular weight of the PUR DNA-binding factor was determined by using a UV cross-linking technique (Chodosh et al., 1986, Mol. Cell. Biol. 6:4723–4733). Aliquots of a standard binding reaction mixture, using as a probe end-labeled single-stranded oligonucleotide MF0677 as outlined for the gel shift assay, were spotted onto plastic wrap covering a UV transilluminator filter (Fotodyne model 3-4500) and exposed to two 15-W, 252-nm UV lamps for various lengths of time. The aliquots were then mixed with an equal volume of 2× sample buffer (4% sodium dodecyl sulfate [SDS], 20% glycerol, 0.001% bromophenol blue, 0.28M 2-mercaptoethanol, 125 mM Tris-HCl [pH 6.6] and subjected to electrophoresis in a discontinuous 12% polyacrylamide gel containing SDS. After electrophoresis, the gel was dried and autoradiographed as described above.

6.1.4. METHYLATION INTERFERENCE ANALYSIS

Methylation interference analysis was conducted as described previously (Postel et al., 1989, Mol. Cell. Biol. 9:5123–5133). MF0677 was end labeled with polynucleotide kinase and [γ-$^{32}$P]ATP and partially methylated with dimethyl sulfate as described by Maxam and Gilbert (1980, Methods Enzymol. 65:499–560). Methylated probe was precipitated twice, suspended in Tris-EDTA, and used in standard gel shift assays. After autoradiography, bands for free and bound probe were excised, case in 1% agarose gels, and transferred by electrophoresis to NA-45 paper (Schleicher & Schuell). DNA fragments were recovered from the paper pieces by incubation at 68° C. for 30 min in 200 μl of elution buffer (10 mM Tris-Cl [pH 8.0], 1 mM EDTA, 1M NaCl ) and ethanol precipitated. The dried pellet was suspended in 100 μl of 1M piperidine and incubated at 95° C. for 30 min. After lyophilization, the pellets were suspended in formamide stop buffer (USB Scientific), and aliquots containing equal counts per minute (as measured by Cerenkov counting) were analyzed by electrophoresis on a 20% sequencing gel, dried, and autoradiographed as described above.

6.1.5. DNA SYNTHESIS ASSAYS

The human fibroblast cell line GM2522 was allowed to grow to confluence over a period of 7–8 days at 37° C. After 7 days in culture, the confluent monolayers have depleted the medium of serum growth factors and the cells have growth arrested. The cells were then stimulated to progress synchronously through the cell cycle by removing the depleted medium and replacing it with fresh medium containing 15% FCS. Sixteen hours prior to serum stimulation the cells were exposed to 3MM concentrations of S-oligonucleotides that were designed to mimic the pyrimidine-rich strand of the PUR element. The pools of degenerate 14-mer oligonucleotides were based on the following sequence: 5'-CCCTTCGCCGCCTC-3' (SEQ ID NO:4) The controls for the experiment included plates containing non-specific oligonucleotides and plates in which no oligonucleotides had been added. The rate of DNA synthesis was determined by measuring the amount of $^{3}$H-thymidine incorporated into newly synthesized cellular DNA. Each time point represents the average of 3 plates.

6.2. RESULTS

Figure 2B:
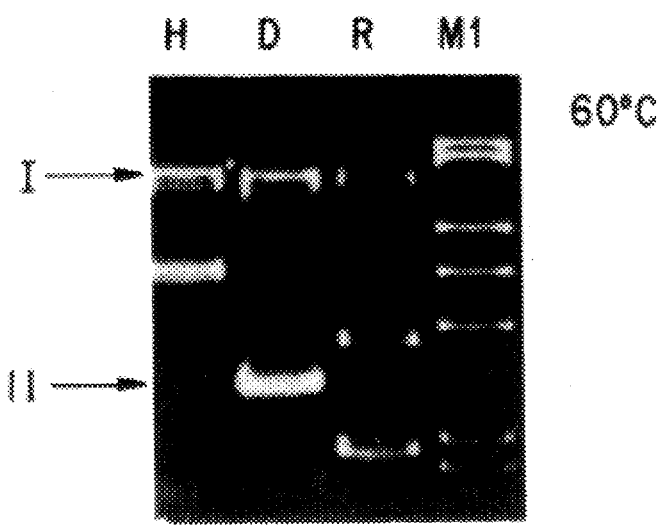

6.2.1. A REGION OF STABLY BENT DNA 1.65 kb UPSTREAM OF THE c-myc P1 PROMOTER To begin characterization of sequence elements within the potential c-myc replication initiation zone, we sought to map the site(s) of stable DNA bending in this region. Experiments of Kumar and Leffak (1989, Nucleic Acids Res. 17:2819–2833) had previously suggested at least one site in this region, but localization with regard to restriction cleavage sites by cyclic permutation had not been performed. Plasmid pMYC47 was created by introducing two copies of the 467-bp Sau3A fragment of the c-myc locus, spanning the region from bp −1970 to −1504 upstream of the c-myc P1 transcription start site, into the BamHi site of pUC19. This region includes much of the potential initiation zone as well as possible transcriptional control sequences (FIG. 1). The two insert copies are in the same orientation. Cyclic permutation experiments were performed by isolating the 973-bp PstI-EcoRI fragment (which contains both copies of the c-myc fragment) from agarose gels and then digesting aliquots with several different restriction endonucleases, each with a unique cleavage site in the 467-bp segment, prior to electrophoresis on polyacrylamide gels (FIG. 2). Each digest generates a 467-bp fragment plus two smaller end fragments. Reduced gel mobility is considered indicative of bending, greatest reduction in mobility occurring when the bend is near the center of a given fragment. It can be seen that RsaI generates a fragment with greatest reduction in mobility. Further evidence for the presence of a bend can be derived from the smaller fragments generated in these digestions. The two smaller fragments generated by DdeI digestion are 252 and 254 bp in length, respectively. Electrophoresis at 4° C. readily resolves these two bands (FIG. 2A, lane D). However, the two bands cannot be resolved by electrophoresis at 60° C. (FIG. 2B, lane D), a temperature at which the anomalous mobility of bent DNA fragments is abolished (Diekmann, S. 1987, Nucleic Acids Res. 15:247–265). In this case, the degree to which the bend retards migration of the slower fragment relative to the unbent fragment is approximately 15%. The mobility of the 341-bp fragment generated by HaeIII digestion is also reduced at 4° C. relative to molecular weight standards. The degrees of retardation of the various fragments are consistent with a bend centered between bp −1667 and −1587 upstream of the P1 start site.

6.2.2. PROTEIN SPECIFICALLY BOUND TO A PURINE-RICH SEQUENCE ELEMENT ADJACENT TO THE DNA BEND

To determine whether a protein(s) can bind to the region of the DNA bend, we first used as a probe a PCR-derived segment comprising 179 bp centered on the bend, as depicted in FIG. 1. Gel band shift assays using this probe revealed a clear protein-induced shift, creating one apparent band. Several oligonucleotides spanning this segment were tested for ability to compete with the segment in the gel shift assay, and competition was observed with use of a 24 bp double-stranded oligonucleotide representing a sequence near the center of the segment. These data are not shown because subsequent experiments have demonstrated the single-strand preference of protein binding to this region. In all experiments using a given putative double-stranded oligonucleotide, it is an inevitable possibility that a single-stranded version of the oligonucleotide, conceivably generated by the reaction, is responsible for the binding or competition observed. Therefore, we present here only results demonstrating unequivocally the single-strand sequence specificity of binding to the original 24-mer. In gel shift assays, an oligonucleotide representing the purine-rich strand of the specifically competing sequence (MF0677) binds a factor occurring in nuclear extracts of HeLa cells (FIG. 3). The binding is sequence specific, since an excess of the unlabeled oligonucleotide effectively prevents formation of the complex in competition experiments, whereas excesses of oligonucleotides with unrelated sequences taken from the c-myc locus do not (FIG. 3). In additional experiments, we have determined that the unlabeled oligonucleotide similarly inhibits binding to the labeled one when an excess of single-stranded M13 DNA is substituted for poly(dI-dC). A nonspecific single-stranded oligonucleotide (MR0740) does not inhibit binding to the labeled probe in the presence of M13 DNA (data not shown). An oligonucleotide in which the three consecutive guanosine residues in MF0677 have been substituted with adenosine residues (MM0677; GGG>AAA in FIG. 3) competes poorly for binding of the factor. However, an oligonucleotide with a sequence occurring within the origin of DNA replication near the CHO dhfr gene (DR3529; dhfr G-A in FIG. 3) is an effective competitor. The complement of DR3529, DF3506 (dhfr C-T in FIG. 3), does not compete. In additional experiments (not shown), we have observed that the factor binds to the dhfr purine-rich oligonucleotide DR3529, used as a labeled probe, and that this binding is effectively competed for by a 20-fold excess of unlabeled c-myc oligonucleotide MF0677. We term the purine-rich binding element the PUR element.

Figure 4B:
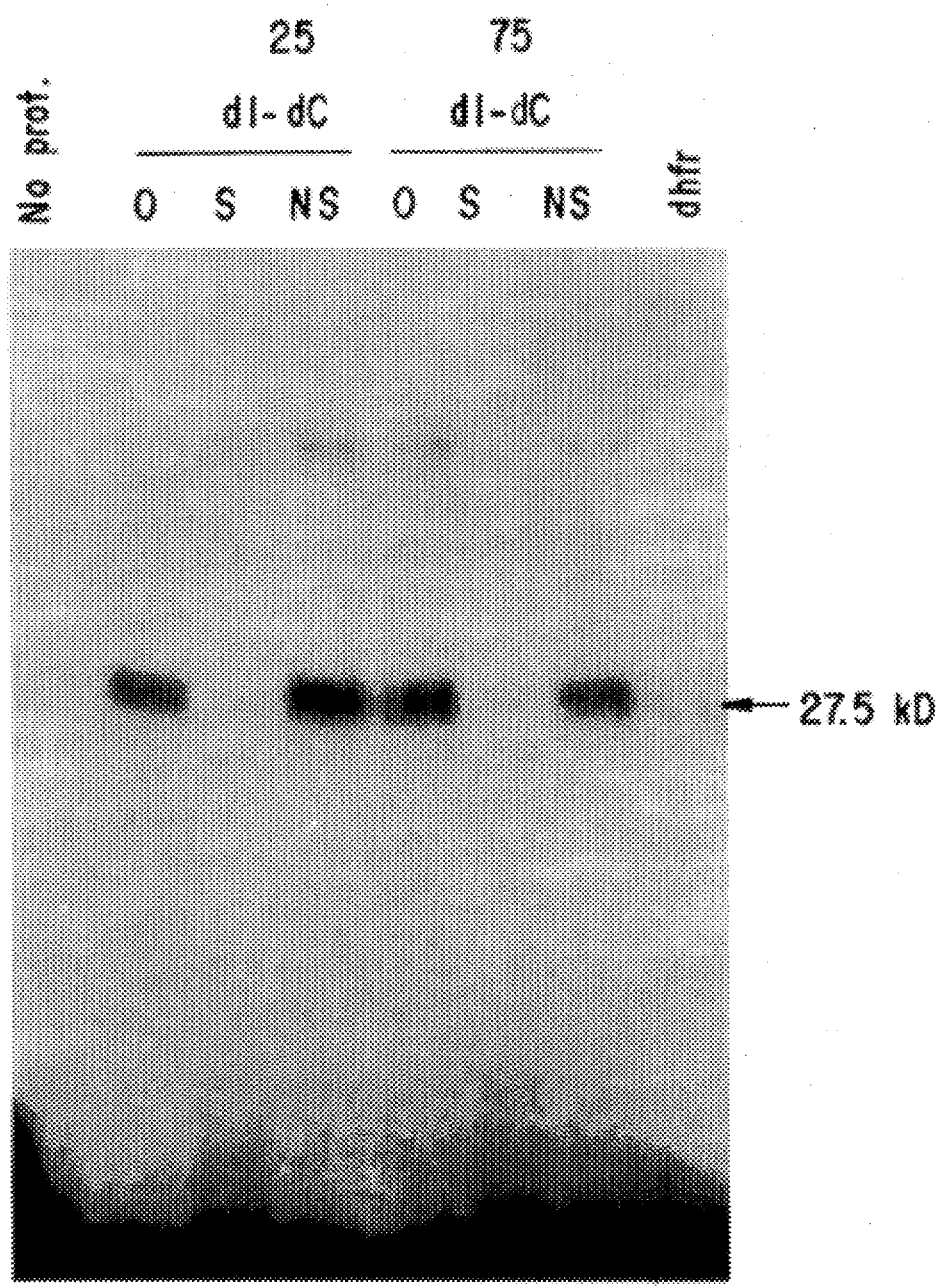

6.2.3. UV IRRADIATION CROSS-LINKS A POLYPEPTIDE WITH THE SINGLE-STRANDED 24-mer CONTAINING THE PUR ELEMENT Results of gel band shift experiments have suggested thus far that only one protein or protein complex is involved in binding the c-myc bend region. We sought to identify any binding protein by UV-induced covalent linkage of the protein to the purine-rich 24-mer, MF0677. UV cross-linking of the factor in HeLa nuclear extracts to $^{34}$P-end-labeled MF0677 generates a labeled band representing Sound complex on protein SDS-polyacrylamide gels. FIG. 4 shows that the amount of this protein bound increases with increased time of exposure to UV. At 2 min, the band detected is narrowly centered on approximately 28 kD. The oligonucleotide contributes relatively little to migration on protein SDS-gels (Chodosh et al., 1986, Mol. Cell. Biol. 6:4723–4733). Nonetheless, the molecular weight obtained by this technique must be considered approximate. Formation of the labeled complex is inhibited by a 100-fold excess of unlabeled MF0677 (FIG. 4B, lane S) but not by a similar excess of nonspecific competitor (FIG. 4B, lane NS). A similar complex forms with the DR3529 oligonucleotide, containing the PUR element sequence version from the dhfr origin region (FIG. 4B, lane dhfr). We term the 28-kDa polypeptide which binds the PUR element Pur.

6.2.4. METHYLATION INTERFERENCE ANALYSIS OF CONTACT POINTS FOR PROTEIN BINDING TO THE PUR ELEMENT

Partial methylation was performed by using dimethyl sulfate with the aim of methylating approximately one purine residue per oligonucleotide molecule (FIG. 5, lanes −). Use of fivefold-greater dimethyl sulfate in the methylation reaction reduces subsequent binding of the factor to MF0677 by more than 80% (FIG. 5A, lanes +). Bands representing bound, unbound, and total DNA from the partial methylation experiment of FIG. 5A were excised and subjected to specific depurination using a piperidine reaction (Maxam, A. M. and W. Gilbert, 1980, Methods in Enzymol. 65:499–560). The vast majority of bound oligonucleotide is unmethylated (FIG. 5B, lane B) as uncleaved material remaining near the gel origin. The residual protein binding (FIG. 5A, lanes +) and cleavage bands (FIG. 5B, lane B) may reflect the greater flexibility of the sugar-phosphate backbone in single-stranded DNA molecules, presumably reducing the steric interference due to the methyl group. The vast majority of unbound probe (FIG. 5B, lane U) is methylated, and thus cleaved by the piperidine reaction, and migrates into the gel. Comparison of lanes B and U clearly shows a pattern of guanosine bases that are under represented in lane B and over represented in lane U. Methylation of these G residues interferes with protein binding. These G residues, highlighted by stars in the sequence in FIG. 5B, are implicated as contact points with Pur. One of these G residues is present in the G triplet motif. This is consistent with results of FIG. 3, showing that altering GGG to AAA reduces protein binding. No adenosine bases are implicated by this experiment as contact points. However, A is somewhat less susceptible than G to cleavage in this protocol. Thymidine bases are not methylated. Additional experiments will be required to document clearly any contact points with T in this single-stranded oligonucleotide.

6.2.5. A PATTERN OF GUANOSINE BASES IS REQUIRED FOR SINGLE-STRAND BINDING SPECIFICITY

Methylation interference results reveal guanosine-protein contact points within the PUR element. It is conceivable that Pur can bind a subcombination of G residues and that more than one such combination exists in the PUR element. For example, either GNGG or GGNGG could be a binding motif, and each is represented three times in the PUR 24-mer. We tested this possibility by using synthetic oligonucleotides with G bases selectively mutated in three combinations (FIG. 6). In each of the combinations, competition for binding to the PUR element is nearly abolished. All three mutations bind protein weakly (lanes a). It is important to note that the gel shown was run at 4° C. When mutant-protein complexes are subjected to electrophoresis at room temperature, they decompose readily, whereas the PUR G-A-protein complex does not. Mut. I in FIG. 6 is the GGG>AAA mutation also shown in FIG. 3. Mut. III has three of the G contact points shown in FIG. 5 disrupted, and it is the least able to compete with added unlabeled DNA. Mut. II is nearly at the level of Mut. III in this regard, and it has only two contact points disrupted, but at the 5' end of the molecule. These data indicate that at least three of the contact points of FIG. 5 are important for initial binding and that disrupting one, two, or three of them seriously disrupts the protein-DNA complex. The data rule out either GNGG or GGNGG as a binding motif, since mutants which do not bind effectively still retain these motifs. The three mutants are equally purine rich. Therefore, the data show that any purine-rich segment is not in itself sufficient to bind Pur. Results are consistent with the notion that one Pur molecule can contact all the observed contact points in the PUR element. These data do not, however, rule out a cooperative mechanism in which binding of one Pur molecule to a G subcombination greatly increases binding of the next Pur molecule.

6.2.6. PUR FACTOR PREFERENTIALLY BINDS A SINGLE-STRANDED VERSUS DOUBLE-STRANDED PUR ELEMENT

We used the double-stranded version of the PUR 24-mer, unlabeled, in competition for protein binding with the labeled single-stranded, purine-rich version. For this procedure, double-stranded oligonucleotides were gel purified from annealed single strands. The double-stranded oligonucleotide for PUR does inhibit binding to the single-stranded version (FIG. 7, lanes 3 to 5), but only at molar concentrations nearly 10-fold higher than does the single-stranded version. A nonspecific single-stranded oligonucleotide does not inhibit binding at any concentration tested (lanes 6 to 8). Similarly, nonspecific double-stranded oligonucleotides [poly(dI-dC)] do not inhibit binding, even at greater than 1,000-fold excess over the labeled probe (lane 12). These results indicate that Pur has an affinity for the double-stranded PUR element. The possibility cannot be excluded that some generation of single-stranded PUR element occurs in the binding reaction and that this is responsible for part of the inhibition. It is unlikely to be responsible for all of the inhibition, however, since that would involve unwinding nearly 10% of the added double-stranded oligonucleotide. In any case, it is clear that affinity for the double-stranded element is at least 10-fold lower than its affinity for the single-stranded, purine-rich PUR sequence.

6.2.7. A CONSENSUS PUR ELEMENT CONSERVED IN EUKARYOTES

We searched the GenBank nucleotide sequence data base for homologies by using the 24-nucleotide sequence comprising the c-myc PUR element region. Numerous matches were recorded from sequences throughout the eukaryotes, particularly from gene 5' flanking regions and replication origins. These primarily centered on a 16-bp core of strong homology, which is presented as a consensus sequence in Table I along with several of the best matches. No homologies to the consensus sequence were found in prokaryotic, plasmid, or phage genomes. Most of these were in gene 5' flanking regions. Four of the best homologies were in regions previously identified as origins of DNA replication or as elements conferring ARS activity (Table I). Surprisingly, one of the best consensus matches was to a sequence repeated near the center of the hamster dhfr replication initiation zone. (This finding compelled us to repeat earlier experiments adding this sequence as shown in FIGS. 3 and 4). The dhfr PUR element is located approximately 17 kb 3' to the dhfr gene, a position not known to harbor any transcriptional regulatory sequences. The PUR element is also located 5' to the mouse c-myc gene and to both human and mouse N-myc genes. At least four of the best matches, noted in Table I, are near genes known to be selectively amplified in cells of their respective organisms.

It can be seen by comparing Table I with FIG. 5 that not all important guanosine contact points for the HeLa Pur protein, detected by methylation interference, are represented in the consensus sequence. Conversely, several purine residues at the 3' end of the PUR consensus sequence are not detected as contact points for the HeLa protein by methylation interference. One plausible explanation for this is that certain purine bases are important for recognition of double-stranded DNA although they are not actually contact points in the stable DNA-protein complex. For example, certain purine bases may be required to maintain double-stranded DNA in a bent configuration, important for recognition, although the single-stranded DNA-protein complex involves other base contact points.

6.2.8. PUR ELEMENT OLIGONUCLEOTIDES DELAY THE ONSET OF DNA REPLICATION IN SERUM STIMULATED HUMAN FIBROBLASTS

Oligonucleotides designed to mimic the pyrimidine rich strand of the PUR element, delay the onset of DNA synthesis in serum-stimulated human fibroblast when compared to plates containing either no oligonucleotides or non-specific oligonucleotides (FIG. 16). These results provide further evidence that the PUR element and the PUR protein play a role in the regulation of cell proliferation and DNA replication.

7. EXAMPLE: CLONING AND SEQUENCING PUR GENE

The subsections below describe the cloning and sequencing of a complementary DNA representing the human PUR gene and the sequence specific single-stranded DNA binding properties of the encoded protein. The deduced amino acid sequence of PUR protein reveals several motifs shared in common between DNA-binding proteins and helix-destabilizing proteins. Northern blot analysis indicates that a family of PUR related genes may exist. Attempts to isolate cDNA clones representing PUR related genes has resulted in the isolation of a PUR related cDNA clone referred to as PURβ.

7.1. MATERIALS AND METHODS
7.1.1. OLIGONUCLEOTIDES USED

Oligonucleotide MF0677 (SEQ ID NO:20) GGAGGTGGTGGAGGGAGAGAAAAG) is a 24-mer representing the c-myc sequence element initially established as binding to Pur. The oligonucleotides used as competitors with MF0677 in binding experiments are listed in Table II.

TABLE II

| Competitor[a] | Sequence | 5-fold[b] | 20-fold[b] |
|---|---|---|---|
| MF0677 (SEQ ID NO: 20) | GGAGGTGGTGGAGGGAGAGAAAAG | 45% | 16% |
| MC0677 (SEQ ID NO: 43) | GGAGGTGGTGGAGGGTTTTTTTTT | 61% | 10% |
| ME0677 (SEQ ID NO: 44) | GGAGGTGGTGGAGGTTTTTTTTTT | 67% | 44% |
| MG0677 (SEQ ID NO: 45) | GGAGGTGGTGGAGTTTTTTTTTTT | 100% | 76% |

TABLE II-continued

| Competitor[a] | Sequence | 5-fold[b] | 20-fold[b] |
|---|---|---|---|
| MH0677 (SEQ ID NO: 46) | TTTTTTTTGGAGGGTTTTTTTT | 82% | 48% |
| MI0677 (SEQ ID NO: 47) | TTTTTTGGTGGAGGGTTTTTTTT | 76% | 35% |
| MJ0677 (SEQ ID NO: 48) | TTTGGTGGTGGAGGGTTTTTTTT | 55% | 15% |
| DR3529 (SEQ ID NO: 35) | TGATGAGGGAGAGGGAGAAGGGAT | 85% | 74% |
| POLYG (SEQ ID NO: 49) | GGGGGGGGGGGGGGGGGGGGGGGG | 93% | 85% |
| POLYA (SEQ ID NO: 50) | AAAAAAAAAAAAAAAAAAAAAAAA | 97% | 99% |

Binding of various synthetic oligonucleotides to protein extract of λAB6 lysogen. Binding reactions were performed as gel-shift assays as described in Section 6.1.2. The labeled probe in each reaction was oligonucleotide MF0677. Competing oligonucleotides were added in either 5-fold or 20-fold excess.

a. Single-stranded oligonucleotides used were the following: MF0677, the 24-mer representing the PUR element site originally detected upstream of the human c-myc gene; MC0677, ME0677, MG0677, MH0677, MI0677, and MJ0677, mutants of oligonucleotide MF0677 in which indicated residues have been replaced by T; DR3529, a 24-mer representing the hamster dhfr version of the PUR element; POLYG and POLYA, homopolymers representing the two most common bases in the PUR element.

b. Following autoradiography of the gel-shift assay results, bands were scanned with a densitometer. Values given represent the per cent of binding activity remaining.

The following two oligonucleotides were used as non-specific competitors in the screening of expression libraries:

MR0740 (SEQ ID NO:39) TCTCAAGCTTGGTCCCT-CAC

MF0562 (SEQ ID NO:37) TACTGAATTCACTTAA-CACT

Oligonucleotides used as primers in 3' and 5' RACE experiments are listed in the legend to FIG. 15.

7.1.2. SCREENING OF EXPRESSION LIBRARIES FOR PROTEINS WITH AFFINITY FOR THE LABELED, SINGLE-STRANDED PUR ELEMENT

A human fetal liver library (Clontech Cat. No. HL1005, prepared in vector λgt11) was screened for clones which bind the purine-rich sequence from upstream of the c-myc gene (oligonucleotide MF0677), essentially as has been described previously for double-stranded oligonucleotides (Singh et al., 1988 Cell 52:415–423; Singh, 1989, In Current Protocols in Molecular Biology, Volume 2, Ausubel et al. (Greene Publishing Associates and Wiley Interscience) p. 12.7.1–12.7.10. The library was plated on E. coli strain Y1090 on a total of six 150 mm plates at a density of 5×10$^4$ PFU per plate. Plates were incubated at 42° C. for 3 hours. The plates were then overlayed with nitrocellulose filters which had previously been saturated with 10 mM IPTG and then dried. The plates were incubated for a further 6 hours at 37° C. and then stored at 4° C. while the filters were being screened. After lifting from plates, filters were immersed in binding buffer (50 mM KCl, 10 mM N-2-hydroxyethyl-piperazine-N'-2-ethanesulfonic acid [HEPES], pH7.8, 0.2 mM EDTA, and 0.5 mM DTT) containing 5% non fat milk powder (Carnation) and gently shaken at room temperature for 60 minutes. Filters were then washed for five minutes at room temperature three times in binding buffer. Filters were then shaken gently for 60 minutes at room temperature in 15 ml of binding buffer containing 10$^6$ cpm of probe (MF0677 labeled by polynucleotide kinase) and 5 µg/ml of each of MF0562 and MR0740. Filters were washed four times in binding buffer (50 ml per filter) at room temperature for 7 minutes and then blotted dry before autoradiography. Potential positives were pooled and rescreened.

7.1.3. DETERMINATION AND ANALYSIS OF THE NUCLEOTIDE SEQUENCE OF PURα

Inserts in λgt11 were cloned into M13 bacteriophage and sequenced by the dideoxy-termination technique (Sanger et al., 1977 Proc. Natl. Acad. Sci. USA 74:5463–5467). Sequence analysis was conducted using the IBI Pustell programs.

7.1.4. DNA BINDING STUDIES OF THE PUR-lacZ FUSION PROTEIN

Y1090 clones lysogenized with λAB5 and λAB6 were isolated by infection at a multiplicity of infection of 10, followed by plating on agar containing Luria broth and incubating overnight at 32° C., as has been previously described (Singh, 1989, In Current Protocols in Molecular Biology, V12 Ausubel et al. (Greene Publishing Associates and Wiley Interscience) p. 12.7.1–12.7.10). Lysogens were then identified by their sensitivity to growth at 42° C. To prepare protein extracts, lysogens were grown at room temperature with shaking in Luria broth until they reached mid-log phase. IPTG was then added to 5 mM and the cultures were incubated at 37° C. for 2 hours with shaking. Aliquots of 1.0 ml of each culture were pelleted at 13,000× g for 2 minutes, and each pellet was resuspended in 50 µl of extraction buffer (10 mM HEPES, pH 7.9, 1 mM EDTA, 1 mM DTT, 1 mM PMSF). Each sample was sonicated six times for 5 sec at an amplitude of 10 microns. To each such protein extract 40 µl of 50% glycerol plus 10 µl of 5M NaCl were added, and extracts were then incubated for 15 minutes at 4° C. The extracts were cleared by 30 minute centrifugation at 13,000× g at 4° C. Protein extracts were prepared for phage lysates as follows. Phage were plated on 150 mm plates at a density of 10$^5$ per plate and incubated at 37° C. for 9 hours. The top agar was collected, mixed with 10 ml of extraction buffer and incubated at 4° C. for 1 hour. The agar was then removed by centrifugation at 12000 × g for 10 minutes and the supernatant dialyzed against extraction buffer for 6 hours at 4° C. Aliquots (2 µl) of each protein extract were used in gel shift assays, as have previously been described for nuclear extracts (Bergemann and Johnson, 1992 Mol. Cell. Biol. 12:1257–1265).

7.1.5. TISSUE CULTURE, POLY(A)$^+$ RNA PREPARATION, AND HYBRIDIZATION ANALYSIS

Cell lines used for the preparation of mRNA were grown in suspension in one liter Corning spinner flasks. HeLa cells were grown in Dulbecco's Modified Eagle Medium (GIBCO), human hepatoma cells (HepG2) were grown in Joklik Modified Eagle Medium (Sigma), and small cell lung carcinoma cells (NCI-NH2) were grown in RPMI 1640 medium (GIBCO). All media were supplemented with 10% fetal calf serum, 50 U/mL penicillin G and 50 µg/mL streptomycin. Cells were pelleted at 1,600× g for 5 minutes. Human fetal liver tissue, second trimester, was kindly supplied by Sunkara Rao, Renata Dische and Stave Kohtz. For preparation of RNA, tissue was frozen in liquid nitrogen and ground in a Biopulverizer. Total RNA was extracted from both tissues and harvested cells as previously outlined (Chirgwin et al., 1979, Biochemistry 18:5294–5299). RNA samples were passed twice through oligo dT-cellulose columns to purify poly(A)+ RNA (Aviv and Leder, 1972 Proc. Natl. Acad. Sci. 69:1408–1412). The RNA concentration of each sample was determined by absorbance at 260 nm. Poly(A)+ RNA (10 µg per lane) was subjected to electrophoresis on 1.2% agarose gels containing 2.2% formaldehyde at 2.5 V/cm for 3.75 hours (Sambrook et al., 1989, In Molecular Cloning VI. 1, p. 7.43–7.45 Cold Spring Harbor Laboratory Press) . RNA was transferred to Gene Screen Plus membranes (Du Pont), exposed to UV for 2 minutes and based at 80° C. in a vacuum oven for 2 hours. Filters were prehybridized for 3 hours at 70.5° C. in northern hybridization solution (50 mM N-tris(hydroxyl)methyl-2-aminoethanesulfonic acid [TES], pH 7.0, 25 mM $Na_2HPO_4$, 25 mM $NaH_2PO_4$, 0.3M NaCl, 30 mM trisodium citrate, 1% SDS, 10% dextran sulphate, 100 µg/mL sonicated salmon sperm DNA and 100 µg/mL yeast RNA), and hybridization to the probe was performed in the same solution at 70.5° C. for 17 hours. The probe used was the 777 bp PstI fragment of the Purα cDNA (nucleotides 165 through 941), labeled with $^{32}P$-phosphate by a random priming procedure (Feinberg and Vogelstein, 1983, Anal. Biochem. 137:266–267). After hybridization, filters were washed twice for 5 minutes each in 2× SSC+SDS (SSC is 150 mM NaCl, 15 mM sodium citrate, pH 7.0) at 70.5° C. and once for 30 minutes in 0.1× SSC+1% SDS at 70.5° C. Filters were then rinsed in 2× SSC and autoradiographed on Kodak XAR film.

7.1.6. 5' AND 3' EXTENSION OF PURα mRNA

HepG2 cell poly(A)+ RNA prepared as described was employed for rapid amplification of cDNA ends (RACE). Rapid amplification of the 3' cDNA end of Pur was carried out essentially as described previously (Frohman et al., 1988 Proc. Natl. Acad. Sci. USA 85:8998–9002). Positions of the primers used are detailed in the legend to FIG. 7. One microgram of HepG2 cell poly(A)+ RNA in 13 µl of distilled water was denatured at 70° C. for 5 minutes and immediately chilled on ice. The first strand cDNA was synthesized with 20 µM primer PDT-01 and 200 U of reverse transcriptase from the SuperScript Preamplification System (BRL) according to the manufacturer's instructions, except that 20 U of RNasin (Promega) was included in the reaction. One microliter of cDNA from the reverse transcription reaction mix was then PCR amplified in 100 µl reaction volume with addition of 2.5 U of Tag polymerase using two primers (PDT-01 and EX-695, each 100 µM). The PCR profile was as follows: denaturation of 94° C. for 1 minute, annealing reaction of 54° C. for 2 minutes, and extension at 72° C. for 5 minutes. One microliter of the first amplification reaction was used for the second amplification of 3' cDNA end of Pur. The primer EX-990 (100 µM) was substituted for primer EX-695. The PCR reaction was performed for 20 cycles in the same reaction buffer, performed as described at 65° C. for 6 hours. The membranes were then washed twice in 2× SSC+1% SDS at 65° C. each for 5 minutes, twice in 0.1× SSC+1% SDS at 65° C. each for 30 minutes, once for 5 minutes in 0.1× SSC and autoradiographed as described above.

7.1.7. SCREENING LIBRARIES BY DNA—DNA HYBRIDIZATION

A λZAP II library of HeLa cell cDNAs was kindly supplied by J. L. Manley. The library was screened for clones of Pur using previously described techniques (Benton and Davis, 1977 Science 196:180–182; Quertermous, 1989 In Current Protocols in Molecular Biology, Vol. 2 Ausubul et al. (Green Publishing Associates and Wiley Interscience); Strauss, 1989 In Current Protocols in Molecular Biology, Vol. 2 Ausubul et al. (Green Publishing Associates and Wiley Interscience). The 777 bp PstI fragment, outlined for use in Northern analysis, was labeled by priming of the Klenow polymerase reaction with random hexanucleotides (Feinberg and Vogelstein, 1983 Anal. Biochem 137:266–267), and hybridized to the filters in hybridization solution (20 mM Tris HCl, Ph 7.6, 10% dextran sulphate, 24 mM sodium phosphate buffer, pH 7.6, 0.1% SDS, 750 mM NaCl, 75 mM trisodium citrate) at 60° C. in wash buffer (40 mM sodium phosphate buffer, pH 7.2, 1 mM EDTA, 5% SDS). Finally, the filters were rinsed twice in 2× SSC and dried prior to autoradiography.

7.1.8. GST-PUR FUSION PROTEINS

An Eco Rl DNA fragment, containing the PUR coding region, was inserted into the Eco Rl site of the expression vector pGEX-1λT. The resulting recombinant expression vector contains the PUR coding region fused to the amino-terminal region of the glutathione-S-transferase protein.

Competent E. coli cells were transformed with recombinant DNA and transformants were selected for on LB/ampicillin plates. For preparation of GST-PUR fusion protein, transformed colonies were inoculated into LB/ampicillin media. The expression of the fusion protein was induced by addition of IPTG to 0.1 mM into the culture media.

Cells were lysed and the extracts were passed over a column containing glutathione-linked agarose beads. The column was washed and the bound protein was eluted by passing a solution containing excess glutathione over the column. The eluted proteins were separated on a SDS polyacrylamide gel and visualized by Coomassie Blue staining of gel.

7.1.9. PUR PROTEIN BINDING THE RETINOBLASTOMA PROTEIN

A PUR-GST fusion protein was expressed in E. coli followed by immobilization of the fusion protein on a glutathione-linked agarose column. WR2E3 cell extracts were passed over the PUR-GST fusion protein column and the bound proteins were eluted with a buffer containing excess glutathione. The eluted proteins were subjected to SDS polyacrylamide gel electrophoresis and blotted onto nitrocellulose membrane. The presence of pRB protein was detected using anti-pRB antibodies.

7.2. RESULTS 7.2.1. ISOLATION OF PUR CLONES FROM A λgt11 EXPRESSION LIBRARY BASED ON AFFINITY FOR THE PUR ELEMENT

There is one sequence of 7 consecutive glutamine residues, and near the carboxy terminus there is a sequence of 5 glutamate residues broken by a single glycine. Glutamine-rich domains have been implicated as transcriptional activation regions in several DNA-binding proteins (Courey et al., 1989 Cell 59:827–836). At the border between the amphipathic helix and the glutamine-glutamate-rich domain there is the motif Ser-Glu-Glu-Met (residues 275 through 278). The serine in this motif is a potential phosphorylation site for casein Kinase II (Kennelly and Krebs, 1991 J. Biol. Chem. 266:15555–15558), although it is not known whether the motif serves this function in Purα.

7.2.2. SPECIFICITY OF SINGLE-STRANDED DNA BINDING BY PUR

Protein extracts derived from either phage lysates or lysogens of λAB5 and λAB6 display the presence of three bands in gel shift assays, using labeled MF0677 as probe, which are not present in controls (solid arrows in FIGS. 13, A and B). The controls employed are either uninfected Y1090 bacteria or lysogen uninduced by IPTG. The clone-specific bands only appear after induction by IPTG, indicating that they result from the fusion of the open reading frame indicated for λAB6 in FIG. 2 to the β-galactosidase gene. The bands are clearly competed by a 20-fold excess of MF0677, but not by a 20-fold excess of polyA oligonucleotide, indicating the sequence-specific nature of the DNA-binding by the fusion proteins. The band nearest the top of the gel is most likely the intact fusion protein since that molecule would be approximately 140 kD in size and would migrate slowly. The two more rapidly-migrating bands generated by each clone are most likely proteolytic products of this larger molecule. There are at least two lower bands in each gel lane that are contributed by E. coli (open arrows in FIGS. 13, A and B), and these proteins are not induced by IPTG ( FIG. 13B, lanes 4 and 5). The E. coli proteins also possess some specific affinity for the Pur element.

Figure 14B:

The specificity of single-stranded DNA binding by Pur was examined in detail by constructing a series of mutated versions of the binding sequence, MF0677, which was used in competition experiments with labeled MF0677 (Table II). Reduction in level of competition by oligonucleotides in which successive guanosine residues are replaced by thymidine residues indicates that the sequence GGAGG is the minimal requirement for binding, although guanosine residues amino-terminal to this sequence are required for optimal binding. The adenosine residues at the 3' end of MF0677 are not required for binding despite the fact that these residues are part of the consensus distribution PUR element. These results concur well with the binding site inferred from methylation interference studies of Pur activity in HeLa cell nuclear extracts (Bergmann and Johnson, 1992 Mol. Cell. Biol. 12:1257–1265). In those experiments protein contacts were observed with several guanosine residues in MF0677, all of which are also important in the present mutational study. For example, the central G residue of a G triplet makes a prominent contact in methylation interference studies, and it is essential for binding by the cloned and expressed Pur protein (Table II, oligonucleotide MG0677). These amplified 3' and 5' mRNA ends using PCR RACE techniques described in Section 7.1.6. Briefly, these employ one PCR primer specific for the Purα sequence and another hybridizing to a poly dT tail formed at either the 3' or 5' end of a reverse transcript of the mRNA. The results of 3' RACE are shown in FIG. 14B. Three primary bands can be seen, indicating either that there are three transcripts hybridizing to the Purα primer, that there are three major splicing products of a Purα transcript, or that there are three major 3' termination sites for a Purα transcript. Further studies of genomic Pur genes will distinguish between these possibilities. The results of 5' RACE are shown in FIG. 6C. Two primary bands can be seen at 200–300 nucleotides and a diffuse range of much less intense bands at 500–700 nucleotides. The smaller band represents artifactual stopping of either reverse transcriptase or Taq polymerase in the G-rich polyglycine sequence near the 5' end of the Pur mRNA. The larger major band corresponds with the 5' end of the sequence shown in FIG. 2 and could represent the 5' end of the Pur transcript. The diffuse smear at 500–700 nucleotides could conceivably represent longer Purα transcripts. It is more likely, however, based on their low level of production, that they are derived from transcripts related to Purα but with only partial homology to the Purα primer. These 3' and 5' RACE results place the size of the Purα mRNA in the range of 1.6 to 2.1 kb. Both the size of the major Purα mRNA and the diversity of homologous species seen are consistent with results obtained by Northern hybridization.

7.2.3. SCREEN OF HeLa CELL LIBRARY REVEALS AT LEAST ONE ADDITIONAL PROTEIN WITH A PUR REPEAT MODULE

Probing $2 \times 10^8$ pfu of a HeLa cell cDNA library with radioactivity labeled 777 bp Pst I fragment (described in Section 7.1.7) of the Purα cDNA resulted in the detection of several hybridizing clones. One of these yielded a new clone of Purα which extends the sequence an additional 51 bp at the 5' end (FIG. 10). Another of these hybridizing clones contains a cDNA, of similar, but not identical sequence to Purα. This cDNA, designated Purβ possesses a copy of the class I repeat module we have described in FIG. 11 followed by an amphipathic helix with considerable sequence similarity to that of Purα (FIGS. 11 and 12). However, the 3' end of Purβ lacks the glutamine-glutamate-rich domain present at that position in Purα.

7.2.4. PUR PROTEIN BINDS TO THE RETINOBLASTOMA PROTEIN

A PUR-GST fusion protein was express in E. coli (FIG. 18). The fusion protein was bound to a glutathione-linked agarose column followed by passage of WR2E3 cell extracts over the PUR-GST column. The bound proteins were eluted and separated on an SDS polyacrylamide gel. The separated proteins were transferred to a nitrocellulose membrane and probed with anti-pRB antibody. Results indicate that the PUR-GST fusion protein binds to the pRB protein with the same affinity as SV40 Large T-antigen and that the PUR protein with the same affinity preferentially to the unphosphorylated form of the pRB protein (FIG. 19).

The present invention is not to be limited in scope by the exemplified embodiments which are intended as illustrations of single aspects of the invention, and any clones, DNA or amino acid sequences which are functionally equivalent are within the scope of the invention. Indeed, various modifications of the invention in addition to those skilled in the art from the foregoing description and accompanying drawings. Such modifications are intended to fall within the scope of the appended claims.

It is also to be understood that all base pair sizes given for nucleotides are approximate and are used for purposes of description.

8. EXAMPLE

ASSOCIATION OF PUR PROTEIN WITH HIV Tat PROTEIN AND Tat RESPONSIVE VIRAL EXPRESSION ELEMENTS

The subsection below describes the binding of PUR protein to the HIV encoded Tat protein. In addition, the PUR protein was shown to bind specifically to Tat responsive viral expression elements.

8.1. MATERIALS AND METHODS

8.1.1. DETECTION OF A TAT-PURα COMPLEX IN HUMAN GLIOBLASTOMA CELLS EXPRESSING THE HIV-1 TAT GENE

Glioblastoma cell line 5–10, constitutively synthesizing Tat expressed under control of the SV40 lat promoter, was cultured in 75 cm$^2$ plates to $5 \times 10^5$ cells per plate. Cells were washed with 150 mM NaCl and lysed in the following buffer at $10^6$ cells/ml: 50 mM Tris-HCl, pH 7.4, 250 mM NaCl, 5.0 mMJ EDTA, 0.1% NP-40, 50 mM NaF, 1.0 mM PMSF, 1 mg/ml leupeptin, 1 mg/ml aprotinin. After 2 min in lysis buffer, extracts were clarified by centrifugation at 14,000× g for 4 min in an Eppendorf centrifuge. After addition of 1.5 ml of lysis buffer with no NaCl, monoclonal antibodies, 2.0 µg, were added to 0.5 ml aliquots of extract. After incubation of 0° C. for 30 min, magnetic beads coupled to sheep anti-mouse antibody (Dynal; 500 μg of beads coupled to approximately 5 μg of antibody) were added to each aliquot. After 2 hrs at 4° C. with gentle shaking, beads were collected by magnetism and washed 5 times with 1 ml of lysis buffer. Proteins attached to sheep-anti-mouse magnetic beads were eluted in 40 μL of SDS sample buffer and subjected to SDS polyacrylamide gel electrophoresis on a 10% gel. After blotting to an Immobilon membrane (Millipore), the membrane was probed with rabbit anti-Tat antibody 705 (NIAID) followed by peroxidase-conjugated goat anti-rabbit antibody using the Dupont Renaissance system. For the lanes labeled IPP, immunoprecipitation was carried out using magnetic beads alone (No first antibody), mouse non-immune serum (Non-imm. ser.), an irrelevant first antibody, anti-influenza virus hemagglutinin epitope monoclonal antibody 12CA5 (Irr. 1st ab) or anti-Purα antibody 5B11 (Anti-Pur mab 5B11). Either glutathione-S-transferase (GST) alone or the fusion protein GST-Purα was expressed in *E. coli* strain BL21LysS and purified on a column containing glutathione-agarose beads (Pharmacia). The expression vector for each was pGEX-1λT (Pharmacia) either containing or containing the EcoRI Purα cDNA insert from plasmid pPUR6. The amounts of proteins bound to glutathione agarose beads were quantified by Coomassie blue staining after SDS gel electrophoresis. Proteins to be tested for binding were passed over columns of beads containing 2 mg of protein. Complexes were washed extensively with lysis buffer, and aliquots of 50 mL of beads were boiled in loading buffer and subjected to electrophoresis on a 10% SDS-PAGE gel. The left lane represents purified Tat protein (400 ng). Lanes labeled Columns represent protein eluted Columns represent protein eluted from columns consisting of beads alone (B), Beads coupled to GST (B-GST) or beads coupled to GST-Purα (B-GST-Pur). For the lanes labeled Tat 400 ng of purified Tat protein was passed over the column. For the lane labeled 5–10 cell lysate, 20 μL of clarified lysate were passed over the column. The gel was transferred to an Immobilon membrane and the membrane probed with anti-Tat antibody nd the Renaissance system as described for panel A. The four lanes at left were exposed to film for equal time, and the lane at the far right 20 times longer. The position 18 kDa represents migration of a prestained lysozyme marker.

8.1.2. BINDING OF PURα TO THE JCV upTAR PUR ELEMENT IN THE PRESENCE OR ABSENCE OF TAT

All gel shifts were performed as described in Section 6.1.2. using $^{32}$P end-labeled 24-mer oligonucleotide probe representing a dimer of the upTAR element. The purine-rich strand of this oligonucleotide is: 5'-GGAGGCGGAGGCGGAGGCGGAGGC-3' (SEQ ID NO:51). For both panels A and B, all Tat, Purα and Purα deletion mutant proteins were employed GST fusion proteins prepared by purification on glutathione agarose columns as described for FIG. 20 and eluted with glutathione[27]. In both panels for lanes labeled +, 7.5 pmoles of each indicated protein were used. Specificity of binding of Purα to the JCV upTAR element. The different oligonucleotide probes used for the indicated reactions are: JCV+, the purine-rich single strand of the upTAR element; JCV ds, the double-stranded upTAR element, only the pyrimidine-rich strand of which is labeled; JCV−, the pyrimidine-rich strand of the upTAR element. Effect of Tat upon biding of a series of Pur deletion mutants to the JCV upTAR element. Tat refers to GST-Tat. GST-PurA refers to full-length GST-Purα, in which Purα is 322aa long. Numbers given for deletion mutants refer to the Purα aa's remaining in the construct, beginning with the N-terminus of Purα, except for PurA del 55-314, in which the identical internal aa's have been deleted.

8.1.3. ASSOCIATION OF TAT AND PURα PROTEINS IN THE PRESENCE OR ABSENCE OF THE JCV upTAR ELEMENT

This method of measuring protein-protein interaction is based on the ability of Purα to bind its recognition element while attached to a nitrocellulose filter. Samples of purified GST-Purα (Pur) and GST-Tat (Tat) or GST-Tat72 (Tat72), 7.5 pmoles each, were incubated, either singly or in combination in 9 mM 4(2-hydroxyethyl)-1-piperazineethanesulfonic acid [HEPES, pH 7.9], 9% glycerol, 45 mM KCl, 0.25 mM dithiothreitol, 0.25 mM phenylmethylsulfonyl fluoride (PMSF), 0.25 mM 1,1-epoxy-3-[p-nitrophenoxy]propane (EPNP), and BSA (1.0 MG/ML), for 2 hr at 30° C. To assay effects of DNA binding by Purα upon the GST-Purα interaction with GST-Tat or GST-Tat72, unlabeled JCV+, the ssDNA purine-rich upTAR 24-mer oligonucleotide was either omitted or included at 10 ng/ml in the incubation. Samples were loaded onto a non-denaturing gel of 3% polyacrylamide (acrylamide:bis-acrylamide=25:1) in running buffer (40 mM Tris-acetate, pH 8.0, 20 mM sodium acetate, 2 mM EDTA) essentially as described by Morrow and Haigh, Jr. and subjected to electrophoresis at 40 v for 36 hrs. Proteins thus separated were electroblotted to a nitrocellulose filter. The filter for the gel presented was cut into portions shown here on the left and right. The left portion filter was blocked with 5% Carnation powdered milk in TNE buffer (50 mM Tris-HCl, pH 7.5, 590 mM NaCl, 1 mM EDTA) for 12 hrs. It was then incubated with $^{32}$P-end-labeled upTAR oligonucleotide (60 Ci/mmole; 200 ng/ml) in TNE containing 1% powdered milk and poly-dI-dC (2.0 g/ml) for 3 hrs at 22° C. The filter was washed 8 times with TNE buffer, air dried and autoradiographed on Dupont Reflection film. Binding of labeled upTAR indicates the position of GST-Purα on the filter. The right portion filter, containing lanes run in parallel to those on the left, was probed with rabbit anti-Tat antibody 705, as described for FIG. 20, to indicate the position of Tat.

8.2. RESULTS 8.2.1. COMPLEX FORMATION BETWEEN TAT-PURα

The human glioblastoma cell line, 5–10, has been derived from line U87-MG transfected with a vector for expression of the tat gene linked to an SV40 promoter and synthesizes Tat constitutively. These cells also contain Purα, as does every mammalian tissue thus far tested. FIG. 20A, a Western blot performed with anti-Tat antibody, shows that Tat and Purα can be immunoextracted as a complex from lysates of 5–10 cells using a monoclonal antibody to Purα. Lysates of 5–10 cells possess a protein of approximately 11,000 kDa which reacts with the anti-Tat antibody (left lane). This protein, migrating at the expected position of Tat, is immunoextracted by the addition of anti-Purα antibody 5B11 (right lane). A larger band in the lysate, possibly representing Tat in a larger complex, is not immunoextracted. FIG. 20B shows that Tat in a cell lysate specifically reacts with Purα fused to glutathione-S-transferase (GST) and coupled to glutathione-agarose beads. The left lane of FIG. 20B shows reaction of the anti-Tat antibody with purified Tat. In the center three lanes purified Tat has been passed over columns containing either beads alone (B), beads coupled to GST alone (B-GST) or beads coupled to GST-Pur (B-GST-Pur). Only the beads containing Purα bind the purified Tat. In the far right lane a 5–10 cell lysate has been passed over the Pur-GST affinity column, showing that Tat is retained.

The gel shift experiments in FIG. 21 show that presence of Tat at a 1:1 molar ratio to Purα, enhances the binding of Purα to its recognition element nearly 10-fold, as seen by comparing JCV+, the purine-rich strand of the PUR element, in the presence of GST-Purα alone (FIG. 21A, Second lane; FIG. 21B, second lane) with JCV+ in the presence of Purα and Tat (FIG. 21A, second lane; FIG. 21B, third lane). FIG. 21A shows that Purα has little or no affinity for either the double-stranded PUR element (JVC ds) or for the pyrimidine-rich strand of the element (JCV–). FIG. 21B shows effects of Tat on DNA binding by a series of Purα deletion mutants. The enhancing effect of Tat on Purα DNA binding is abolished when the amino-terminal 85 amino acids of Purα are removed. In experiments not shown we have determined that the enhancing effect of Tat is dependent upon Tat concentration and is maximal at a Tat:Purα molar ratio of 1:1. In time courses Tat does not affect the rate of DNA binding by Purα but increases the amount of DNA bound at each individual time point. This indicates that Tat's effect is to influence the DNA binding of individual Pur molecules rather than to increase the number of Purα molecules participating in binding.

Purα binds DNA in monomeric form (FIG. 21B, fastest-migrating gel-shift band) and as a series of multimeric aggregates. The amino terminus of Purα affects the association of Purα molecules, allowing more of the protein to exist in monomeric form. As more of the terminus id deleted, only higher-order multimers of Pur are seen (FIG. 21B). Tat enhances the DNA binding of all multimeric forms of Purα>10-fold but does not shift the position of any of these bands, suggesting that Tat is not present in a ternary Tat-Purα-DNA complex.

FIG. 22 shows that presence of the single-stranded PUR recognition element dissociates the Tat-Purα complex. This figure, which is not a standard gel-shift, utilizes a new procedure to examine protein-protein interaction in the presence or absence of DNA. Tat and Purα are subjected to non-denaturing gel electrophoresis either alone or together. Following electrophoresis, the proteins are blotted to a nitrocellulose filter and the filter probed with either the labeled JCV PUR recognition element, upTAR, (FIG. 22, left) or with an anti-Tat antibody (FIG. 22, right). The lanes for FIG. 22, left, were run on the same gel as, in parallel to, those for FIG. 22, right, and the filter cut prior to probing. The advantage of this system is that labeled DNA may or may not be included in the electrophoresis. FIG. 22, left, shows that Pur alone migrates as a series of multimers and that these are only slightly shifted by presence of the JCV PUR element. In the presence of Tat, Purα is shifted to near the top of the gel and, as in FIG. 21, the overall level of DNA binding is enhanced several fold. It should be noted that blotting may affect the Tat-Purα association so that the two proteins may no longer be together with Purα binds the probe in its position near the top of the gel. Addition of the unlabeled PUR element during electrophoresis disrupts the Tat-Purα complex, as seen in the lane+Tat+Pur. Intriguingly, DNA binding by Purα is enhanced by Tat even after Tat and Purα are no longer associated. This explains the strong enhancement of Purα DNA binding by Tat in FIG. 21 even though the Purα-DNA complexes are not supershifted by the Tat protein. FIG. 22, right shows that Tat is present in the complexes near the top of the get but not in the faster-migrating Pur multimers. The last lane in FIG. 22, right, shows that the PUR element dissociates higher-order Tat-Pur multimers to form faster-migrating complexes. These data are further evidence that a transient association with Tat alters the way in which individual Pure molecules bind to DNA.

Purα is unique in its interaction with Tat. Purα, an activator of cellular gene transcription, specifically binds to its JCV recognition element, upTAR, which has been demonstrated to confer Tat responsiveness to late gene transcriptional activation. Since Tat does not bind the upTAR element itself, this earlier work implied that Tat might stimulate late gee transcription by interacting, either directly or indirectly, with Purα. Here we show that Tat not only interacts directly with Purα, but that the interaction has functional consequences for DNA binding. Various cellular proteins have been reported to bind the HIV-1 Tat protein, including TBP-1, SPI, NF-κB and TAP. Purα shares no extensive homology with any of these proteins. The role of any Tat-associated protein in transcriptional activation by Tat remains to be determined. Any mechanism by which Tat and Purα influence transcription may not be determined. Any mechanism by which Tat and Purα influence transcription may not be limited to the JCV late promoter. The sequence GGGAG is a minimal binding site for Purα, and it is present in the loop structure of TAR RNA near nucleotides reported to be important for Tat binding. In preliminary experiments we have demonstrated that Purα binds to this TAR loop element.

The enhancing effect upon DNA binding by Purα is produced by the first 72 amino acids of Tat and depends upon presence of the first 85 amino acids of Purα (FIG. 21B). This specificity rules out certain potentially trivial sources of Tat-Purα interaction. For example, Purα contains a region with 6 of 7 D or # residues, and it was conceivable that this could ironically bind to the region of Tat containing 8 of 9K or R residues. This is not the case, however, since a Purα mutant lacking the acidic region, Purα 1–314, still shows DNA-binding enhancement by Tat. Purα has a complex structure with two series' of interspersed repeats, a glutamine-rich potential transactivation domain, a region of amphipathic helix and a glycine-rich domain. It would be worthwhile to determine precisely the amino acids involved in Tat binding since these may be targeted with potential inhibitors of the interaction.

9. EXAMPLE

LOCALIZATION OF PURα GENE

The subsection below describes gene mapping data localizing the PURα gene to 5q31, a region of the genome often found deleted in various proliferative disorders.

9.1. MATERIALS AND METHODS

9.1.1. PREPARATION OF PROBES

A human placental genomic DNA library in phage vector EMBL3 (Stratagene) was screened using the purα cDNA insert from pPUR6 (Bergemann et al. 1992). A clone bearing a 16 kb insert was obtained (EMhPur1), and it was determined that this contained an 11.5 kb HindIII fragment identified on genomic restriction fragment blots as contained the purα gene. Subcloning PstI fragments into pBluescript (Stratagene) and DNA sequencing confirmed that the 16 kb insert contained purα gene sequences. The 16 kb purα genomic clone, was used for fluorescence in situ hybridization (FISH). For blot hybridization analysis a 777 bp PstI fragment of pPUR6 was used as a probe. This fragment includes the entire C-terminal coding region of Purα, but it omits a poly-Gly region near the Purα N-terminus which hybridizes to many loci (Bergemann et al. 1992).

9.1.2. FLUORESCENCE IN SITU HYBRIDIZATION (FISH)

To localize the pur gene by FISH, the kb purα genomic clone was labeled with biotin-11-dUTP (Sigma, St. Louis) and hybridized to metaphase chromosomes as previously described (Najfeld et al. 1992a; Najfeld et al. 1992b) using metaphase spreads obtained from a healthy individual.

9.1.3. HYBRIDIZATION TO DNA OF HUMAN-HAMSTER HYBRID CELLS BEARING INDIVIDUAL HUMAN CHROMOSOMES

Human-hamster hybrid cell lines NA10114 and NA11580, bearing individual human chromosomes 5 and 6, respectively, were obtained from the NIGMS Human Genetic Mutant Cell Repository. Genomic DNA was subjected to restriction endonuclease cleavage and electrophoresis on a 1.0% (w/v) agarose gel, blotted to Gene-Screen Plus membranes and hybridized as described in the legend to FIG. 3.

9.2. RESULTS 9.2.1. CHROMOSOME LOCALIZATION OF PURα BY FISH

Hybridization to only chromosome band 5q31 was recorded in 14 of 52 metaphases, and hybridization to only 6q14 in 18. Hybridization to both 5q31 and 6q14 was recorded in an additional 20 metaphases (FIG. 1). Additional hybridization signals were recorded at 1q13, in a single metaphase, and at 7p13 in two metaphases, to both homologs in each case. Hybridization signals were recorded on one homolog of 15q13 in two metaphases. The hybridization loci were identified by combining the fluorescence images of the probe signals with fluorescence banding patterns of an Alu-specific oligonucleotide probe (R-like banding; Matera and Ward, 1992) and DAPI staining (G-banding), as shown for chromosome 5 in FIG. 2. Hybridization was subsequently performed in the presence of unlabeled, competing Purβ cDNA (406 bp Eco RI fragment as described in Materials and Methods) at a 300-fold excess of competitor over probe. The Purβ cDNA is >80% homologous to purα over approximately 300 bp of the purβ probe (Bergemann et al. 1992). Under these conditions the hybridizations signal was detected at 6q14 in 10 metaphases and at 5q31 and 6q14 in 4 metaphases. None of the metaphases showed a signal on only 5q31. This results allows either of two conclusions, depending upon the efficacy of competition at the given level of stringency: 1) either purα or purβ is located at 5q31, and the sequence at 6q41 is a similar, but less homologous, relative; or, 2) purβ is located at 5q31 and purα is located at 6q14. In the latter case, the stringency must be such that the unlabeled purβ is not competing with the purα probe. In order to distinguish between these possibilities, we analyzed DNA from human-hamster cell hybrids.

9.2.2. HYBRIDIZATION ANALYSIS OF GENOMIC DNA FROM HUMAN-HAMSTER HYBRID CELL LINES BEARING INDIVIDUAL HUMAN CHROMOSOMES 5 OR 6

The genomic DNAs of cell lines NA10114 and NA11580 were individually digested with either HindIII or EcoRI and hybridized with the 777-bp PstI fragment from human Purα cDNA (FIG. 3A). Three bands are visualized in the CHO control lane representing hamster pur genes, one at approximately 7 kb and two at 9–11 kb. Only two of these, at approximately 7 and 9 kb, are seen in the human-hamster cell hybrid DNAs. This represents a polymorphism in the hamster pur genes but does not affect interpretation of hybridization to the human chromosomes. An 11.5 kb HindIII band is hybridized in the human DNA control lanes for HeLa and human placental DNA and in the lane for the line bearing individual chromosome 5 but not in the CHO DNA control lane or in the lane for the line bearing individual chromosome 6. The 13 kb EcoRI fragment is hybridized in the human control DNA samples and in the lane for chromosome 5 but not in the CHO lane or the lane for chromosome 6. As described below, the 11.5 kb HindIII fragment and the 13 kb EcoRI fragment have been definitively identified as derived from purα by DNA sequencing of human genomic clones. These results confirm that the human purα gene is located on chromosome 5. By integrating this conclusion with the results of fluorescence in situ hybridization, we conclude that the human purα gene is located at 5q31.

In the HeLa and human placental DNA lanes of FIG. 3A, two bands can be discerned upon cleavage with HindIII and hybridization to the pur genomic probe: a strong band at 5 kb and a weaker band at approximately 5 kb. We have now isolated human genomic clones containing each of these HindIII fragments. Partial sequencing reveals that the 11.5 kb fragment is from the pur locus while the 5 kb fragment is from the purB locus. The 5 kb HindIII fragment is not hybridized in either the lanes for chromosome 5 or chromosome 6 whereas the 11.5 kb HindIII fragment is strongly hybridized in the lane for chromosome 5. This suggests that the purβ locus is not located on either chromosome 5 or 6. We have confirmed this observation by hybridizing genomic blots with the 406 bp purβ cDNA probe. Neither the chromosome 5-containing DNA sample nor the chromosome 6-containing DNA sample hybridized to the purβ probe to yield a human-specific fragment. The 11.5 kb HindIII purα fragment contains one NotI restriction site, and this corresponds to the NotI site in purα cDNA (Bergemann et al. 1992). This allows positioning of the purα cDNA sequences within the 11.5 kb HindIII fragment. A map of the human purα gene with respect to several known restriction sites is presented in FIG. 3B.

---

What is claimed is:

1. A method for identifying a compound in a chemical or biological preparation that binds to PUR or binding fragments of PUR thereof comprising:

(i) contacting the chemical or biological preparation with a solid phase matrix wherein PUR or fragments are immobilized to said matrix to permit said compound to bind to said solid phase matrix;

(ii) removing any unbound material from said solid phase matrix; and (iii) detecting the presence of the compound bound to the solid phase.

2. The method of claim 1, which further includes the step of eluting the compound from the solid phase matrix, thereby isolating the compound.

3. A method whereby a peptide that binds to PUR may be identified comprising:

(i) contacting PU protein with a random peptide library such that PUR will recognize and bind to one or more peptide species within the library;

(ii) isolating the PUR/peptide combination;

(iii) determining the sequence of the peptide isolated in step (ii).

4. A method of identifying a compound that modulates the binding of PUR to pRB comprising:

(i) contacting a mixture of PUR protein and said compound to pRB;

(ii) measuring the binding of PUR to pRB; and (iii) comparing the measured level of pRB binding to the level of binding in the absence of exposure of PUR to said compound.

5. A method for identifying a compound that modulates the binding of PUR to pRB comprising:
   (i) contacting a cell line expressing PUR and pRB with said compound; and
   (ii) measuring the binding of PUR to pRB; and
   (iii) comparing the measured level of pRB binding to the level of binding in the absence of exposure to said compound.

6. A method of identifying a compound that modulates the binding of PUR protein to HIV encoded Tat protein comprising:
   (i) contacting a mixture of PUR protein and said compound to HIV encoded Tat protein;
   (ii) measuring the binding of PUR to Tat; and
   (iii) comparing the measured level of HIV encoded Tat protein binding to the level of binding in the absence of exposure of PUR protein to said compound.

7. A method for identifying a compound that modulates the binding of PUR to HIV encoded Tat protein comprising:
   (i) contacting a cell line expressing PUR and HIV encoded Tat protein with test compound; and
   (ii) measuring the binding of PUR to HIV encoded Tat protein; and
   (iii) comparing the measured level of Tat binding to the level of PUR binding in the absence of exposure of PUR to compound.

8. A method for identifying a compound that modulates the DNA binding activity of PUR comprising:
   (i) contacting a mixture of PUR protein and said compound to DNA to which PUR normally binds;
   (ii) measuring the binding of PUR to DNA; and
   (iii) comparing the measured level of DNA binding to the level of binding in the absence of exposure of PUR protein to compound.

9. The method of claim 8 wherein the DNA is a PUR element.

10. The method of claim 8 wherein the DNA is a Tat responsive transcriptional element.

11. The method of claim 8 wherein the DNA is an HIV-TAR sequence.

12. The method of claim 10 wherein the DNA is a JCV late promoter.

* * * * *

SEQUENCE LISTING ( 1 ) GENERAL INFORMATION:

( i i i ) NUMBER OF SEQUENCES: 51

( 2 ) INFORMATION FOR SEQ ID NO:1:

( i ) SEQUENCE CHARACTERISTICS:
        ( A ) LENGTH: 270 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:1:

```
TACTATATTC   ACTTAACACT   TGAACGCTGA   GCTGCAAACT   CAACGGGTAA   TAACCCATCT         60
```

| TGAACAGCGT | ACATGCTATA | CACACACCCC | TTTCCCCCGA | ATTGTTTTCT | CTTTTGGAGG | 120 |
| TGGTGGAGGG | AGAGAAAAGT | TTACTTAAAA | TGCCTTTGGG | TGAGGGACCA | AGGATGAGAA | 180 |
| GAATGTTTTT | TGTTTTTCAT | GCCGTGGAAT | AACACAAAAT | AAAAAATCCC | GAGGGAATAT | 240 |
| ACATTATATA | TTAAATATAG | ATCATTTCAG | | | | 270 |

(2) INFORMATION FOR SEQ ID NO:2:

(i) SEQUENCE CHARACTERISTICS:
        (A) LENGTH: 1144 base pairs
        (B) TYPE: nucleic acid
        (C) STRANDEDNESS: single
        (D) TOPOLOGY: unknown (ii) MOLECULE TYPE: DNA (genomic)

(ix) FEATURE:
        (A) NAME/KEY: CDS
        (B) LOCATION: 60..1028

(xi) SEQUENCE DESCRIPTION: SEQ ID NO:2:

```
CGACTGAGGC GGCGGGCGGA GCGGCAGGCG GCGGCGGCGC GGCAGCGGAG CGCAGCATC                    59

ATG GCG GAC CGA GAC AGC GGC AGC GAG CAG GGT GGT GCG GCG CTG GGT                    107
Met Ala Asp Arg Asp Ser Gly Ser Glu Gln Gly Gly Ala Ala Leu Gly
  1           5                  10                  15

TCG GGC GGC TCC CTG GGG CAC CCC GGC TCG GGC TCA GGC TCC GGC GGG                    155
Ser Gly Gly Ser Leu Gly His Pro Gly Ser Gly Ser Gly Ser Gly Gly
             20                  25                  30

GGC GGT GGT GGC GGG GGC GGC GGC GGC AGT GGC GGC GGC GGC GGC                        203
Gly Gly Gly Gly Gly Gly Gly Gly Gly Ser Gly Gly Gly Gly Gly
                 35                  40                  45

GGG GCC CCA GGG GGG CTG CAG CAC GAG ACG CAG GAG CTG GCC TCC AAG                    251
Gly Ala Pro Gly Gly Leu Gln His Glu Thr Gln Glu Leu Ala Ser Lys
 50                  55                  60

CGG GTG GAC ATC CAG AAC AAG CGC TTC TAC CTG GAC GTG AAG CAG AAC                    299
Arg Val Asp Ile Gln Asn Lys Arg Phe Tyr Leu Asp Val Lys Gln Asn
 65                  70                  75                  80

GCC AAG GGC CGC TTC CTG AAG ATC GCC GAG GTG GGC GCG GGC GGC AAC                    347
Ala Lys Gly Arg Phe Leu Lys Ile Ala Glu Val Gly Ala Gly Gly Asn
                 85                  90                  95

AAG AGC CGC CTT ACT CTC TCC ATG TCA GTG GCC GTG GAG TTC CGC GAC                    395
Lys Ser Arg Leu Thr Leu Ser Met Ser Val Ala Val Glu Phe Arg Asp
                100                 105                 110

TAC CTG GGC GAC TTC ATC GAG CAC TAC GCG CAG CTG GGC CCC AGC CAG                    443
Tyr Leu Gly Asp Phe Ile Glu His Tyr Ala Gln Leu Gly Pro Ser Gln
            115                 120                 125

CCG CCG GAC CTG GCC CAG GCG CAG GAC GAG CCG CGC GGC GCG CTC AAA                    491
Pro Pro Asp Leu Ala Gln Ala Gln Asp Glu Pro Arg Arg Ala Leu Lys
        130                 135                 140

AGC GAG TTC CTG GTG CGC GAG AAC CGC AAG TAC TAC ATG GAT CTC AAG                    539
Ser Glu Phe Leu Val Arg Glu Asn Arg Lys Tyr Tyr Met Asp Leu Lys
145                 150                 155                 160

GAG AAC CAG CGC GGC CGC TTC CTG CGC ATC CGC CAG ACG GTC AAC CGG                    587
Glu Asn Gln Arg Gly Arg Phe Leu Arg Ile Arg Gln Thr Val Asn Arg
                165                 170                 175

GGG CCT GGC CTG GGC TCC ACG CAG GGC CAG ACC ATT GCG CTG CCC GCG                    635
Gly Pro Gly Leu Gly Ser Thr Gln Gly Gln Thr Ile Ala Leu Pro Ala
                180                 185                 190

CAG GGG CTC ATC GAG TTC CGT GAC GCT CTG GCC AAG CTC ATC GAC GAC                    683
Gln Gly Leu Ile Glu Phe Arg Asp Ala Leu Ala Lys Leu Ile Asp Asp
            195                 200                 205

TAC GGA GTG GAG GAG GAG CCG GCC GAG CTG CCC GAG GGC ACC TCC TTG                    731
```

```
Tyr Gly Val Glu Glu Glu Pro Ala Glu Leu Pro Glu Gly Thr Ser Leu
210                 215                 220

ACT GTG GAC AAC AAG CGC TTC TTC TTC GAT GTG GGC TCC AAC AAG TAC    779
Thr Val Asp Asn Lys Arg Phe Phe Phe Asp Val Gly Ser Asn Lys Tyr
225                 230                 235                 240

GGC GTG TTT ATG CGA GTG AGC GAG GTG AAG CCC ACC TAT CGC AAC TCC    827
Gly Val Phe Met Arg Val Ser Glu Val Lys Pro Thr Tyr Arg Asn Ser
                245                 250                 255

ATC ACC GTC CCC TAC AAG GTG TGG GCC AAG TTC GGA CAC ACC TTC TGC    875
Ile Thr Val Pro Tyr Lys Val Trp Ala Lys Phe Gly His Thr Phe Cys
            260                 265                 270

AAG TAC TCG GAG GAG ATG AAG AAG ATT CAA GAG AAG CAG AGG GAG AAG    923
Lys Tyr Ser Glu Glu Met Lys Lys Ile Gln Glu Lys Gln Arg Glu Lys
        275                 280                 285

CGG GCT GCC TGT GAG CAG CTT CAC CAG CAG CAA CAG CAG CAG CAG GAG    971
Arg Ala Ala Cys Glu Gln Leu His Gln Gln Gln Gln Gln Gln Gln Glu
    290                 295                 300

GAG ACC GCC GCT GCC ACT CTG CTA CTG CAG GGT GAG GAA GAA GGG GAA    1019
Glu Thr Ala Ala Ala Thr Leu Leu Leu Gln Gly Glu Glu Glu Gly Glu
305                 310                 315                 320

GAA GAT TGA TCAAACAGAA TGAAACCCCC ACACACACAC ACATGCATAC            1068
Glu Asp *
ACACACACAC ACAGCCACAC ACACAGAAAA TATACTGTAA AGAAAGAGAG AAAATAAAAA    1128

GTTAAAAAGT TAAAAA                                                   1144
```

( 2 ) INFORMATION FOR SEQ ID NO:3:

( i ) SEQUENCE CHARACTERISTICS:
        ( A ) LENGTH: 322 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:3:

```
Met Ala Asp Arg Asp Ser Gly Ser Glu Gln Gly Gly Ala Ala Leu Gly
1               5                   10                  15

Ser Gly Gly Ser Leu Gly His Pro Gly Ser Gly Ser Gly Ser Gly Gly
            20                  25                  30

Gly Gly Gly Gly Gly Gly Gly Gly Gly Ser Gly Gly Gly Gly Gly
        35                  40                  45

Gly Ala Pro Gly Gly Leu Gln His Glu Thr Gln Glu Leu Ala Ser Lys
    50                  55                  60

Arg Val Asp Ile Gln Asn Lys Arg Phe Tyr Leu Asp Val Lys Gln Asn
65                  70                  75                  80

Ala Lys Gly Arg Phe Leu Lys Ile Ala Glu Val Gly Ala Gly Gly Asn
                85                  90                  95

Lys Ser Arg Leu Thr Leu Ser Met Ser Val Ala Val Glu Phe Arg Asp
            100                 105                 110

Tyr Leu Gly Asp Phe Ile Glu His Tyr Ala Gln Leu Gly Pro Ser Gln
        115                 120                 125

Pro Pro Asp Leu Ala Gln Ala Gln Asp Glu Pro Arg Arg Ala Leu Lys
    130                 135                 140

Ser Glu Phe Leu Val Arg Glu Asn Arg Lys Tyr Tyr Met Asp Leu Lys
145                 150                 155                 160

Glu Asn Gln Arg Gly Arg Phe Leu Arg Ile Arg Gln Thr Val Asn Arg
                165                 170                 175

Gly Pro Gly Leu Gly Ser Thr Gln Gly Gln Thr Ile Ala Leu Pro Ala
            180                 185                 190
```

```
Gln Gly Leu Ile Glu Phe Arg Asp Ala Leu Ala Lys Leu Ile Asp Asp
        195                 200                 205

Tyr Gly Val Glu Glu Glu Pro Ala Glu Leu Pro Glu Gly Thr Ser Leu
    210                 215                 220

Thr Val Asp Asn Lys Arg Phe Phe Phe Asp Val Gly Ser Asn Lys Tyr
225                 230                 235                 240

Gly Val Phe Met Arg Val Ser Glu Val Lys Pro Thr Tyr Arg Asn Ser
                245                 250                 255

Ile Thr Val Pro Tyr Lys Val Trp Ala Lys Phe Gly His Thr Phe Cys
                260                 265                 270

Lys Tyr Ser Glu Glu Met Lys Lys Ile Gln Glu Lys Gln Arg Glu Lys
            275                 280                 285

Arg Ala Ala Cys Glu Gln Leu His Gln Gln Gln Gln Gln Gln Gln Glu
    290                 295                 300

Glu Thr Ala Ala Ala Thr Leu Leu Leu Gln Gly Glu Glu Glu Gly Glu
305                 310                 315                 320

Glu Asp
```

(2) INFORMATION FOR SEQ ID NO:4:

(i) SEQUENCE CHARACTERISTICS:
        (A) LENGTH: 23 amino acids
        (B) TYPE: amino acid
        (D) TOPOLOGY: unknown (ii) MOLECULE TYPE: peptide (xi) SEQUENCE DESCRIPTION: SEQ ID NO:4:

```
Val Asp Ile Gln Asn Lys Arg Phe Tyr Leu Asp Val Lys Gln Asn Ala
1               5                   10                  15

Lys Gly Arg Phe Leu Lys Ile
                20
```

(2) INFORMATION FOR SEQ ID NO:5:

(i) SEQUENCE CHARACTERISTICS:
        (A) LENGTH: 23 amino acids
        (B) TYPE: amino acid
        (D) TOPOLOGY: unknown (ii) MOLECULE TYPE: peptide (xi) SEQUENCE DESCRIPTION: SEQ ID NO:5:

```
Leu Val Arg Gln Asn Arg Lys Tyr Tyr Met Asp Leu Lys Glu Asn Gln
1               5                   10                  15

Arg Gly Arg Phe Leu Arg Ile
                20
```

(2) INFORMATION FOR SEQ ID NO:6:

(i) SEQUENCE CHARACTERISTICS:
        (A) LENGTH: 23 amino acids
        (B) TYPE: amino acid
        (D) TOPOLOGY: unknown (ii) MOLECULE TYPE: peptide (xi) SEQUENCE DESCRIPTION: SEQ ID NO:6:

```
Leu Thr Val Asp Asn Lys Arg Phe Phe Phe Asp Val Gly Ser Asn Lys
1               5                   10                  15

Tyr Gly Val Phe Met Arg Val
                20
```

( 2 ) INFORMATION FOR SEQ ID NO:7:

( i ) SEQUENCE CHARACTERISTICS:
        ( A ) LENGTH: 23 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:7:

```
Ile Thr Val Asp Ser Lys Arg Phe Phe Phe Asp Val Gly Cys Asn Lys
 1               5                  10                  15

Tyr Gly Val Phe Leu Arg Leu
            20
```

( 2 ) INFORMATION FOR SEQ ID NO:8:

( i ) SEQUENCE CHARACTERISTICS:
        ( A ) LENGTH: 25 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:8:

```
Ala Val Glu Phe Arg Asp Tyr Leu Gly Asp Phe Ile Glu His Tyr Ala
 1               5                  10                  15

Gln Leu Gly Pro Ser Gln Pro Pro Asp
            20                  25
```

( 2 ) INFORMATION FOR SEQ ID NO:9:

( i ) SEQUENCE CHARACTERISTICS:
        ( A ) LENGTH: 26 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:9:

```
Leu Ile Glu Phe Arg Asp Ala Leu Ala Lys Leu Ile Asp Asp Tyr Gly
 1               5                  10                  15

Val Glu Glu Glu Pro Ala Glu Leu Pro Glu
            20                  25
```

( 2 ) INFORMATION FOR SEQ ID NO:10:

( i ) SEQUENCE CHARACTERISTICS:
        ( A ) LENGTH: 28 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:10:

```
Pro Ser Tyr Arg Asn Ala Ile Thr Val Pro Phe Lys Ala Trp Gly Lys
 1               5                  10                  15

Phe Gly Gly Ala Phe Cys Arg Tyr Ala Asp Glu Met
            20                  25
```

( 2 ) INFORMATION FOR SEQ ID NO:11:

( i ) SEQUENCE CHARACTERISTICS:
        ( A ) LENGTH: 22 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:11:

Pro Ser Tyr Asp Ser Val Arg Arg Gly Ala Trp Gly Asn Asn Met Asn
1               5                   10                  15

Ser Gly Leu Asn Lys Ser
            20

( 2 ) INFORMATION FOR SEQ ID NO:12:

( i ) SEQUENCE CHARACTERISTICS:
( A ) LENGTH: 22 amino acids
( B ) TYPE: amino acid
( D ) TOPOLOGY: unknown ( i i ) MOLECULE TYPE: peptide ( x i ) SEQUENCE DESCRIPTION: SEQ ID NO:12:

Ala Thr Tyr Arg Asn Val Thr Ala Glu Gln Ala Arg Asn Trp Gly Leu
1               5                   10                  15

Gly Gly His Ala Phe Cys
            20

( 2 ) INFORMATION FOR SEQ ID NO:13:

( i ) SEQUENCE CHARACTERISTICS:
( A ) LENGTH: 26 amino acids
( B ) TYPE: amino acid
( D ) TOPOLOGY: unknown ( i i ) MOLECULE TYPE: peptide ( x i ) SEQUENCE DESCRIPTION: SEQ ID NO:13:

Pro Thr Tyr Gly Thr Asp Glu Trp Glu Gln Trp Trp Asn Ala Phe Asn
1               5                   10                  15

Glu Glu Asn Leu Phe Cys Ser Glu Glu Met
            20                  25

( 2 ) INFORMATION FOR SEQ ID NO:14:

( i ) SEQUENCE CHARACTERISTICS:
( A ) LENGTH: 28 amino acids
( B ) TYPE: amino acid
( D ) TOPOLOGY: unknown ( i i ) MOLECULE TYPE: peptide ( x i ) SEQUENCE DESCRIPTION: SEQ ID NO:14:

Pro Thr Tyr Arg Asn Ser Ile Thr Val Arg Tyr Lys Val Trp Ala Lys
1               5                   10                  15

Phe Gly His Thr Phe Cys Lys Tyr Ser Glu Glu Met
            20                  25

( 2 ) INFORMATION FOR SEQ ID NO:15:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:15:

TATCTGCAGT TTTTTTTTT TTTTTT                                26

( 2 ) INFORMATION FOR SEQ ID NO:16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

CTCGGCGATC TTCAGGAA                                            18

( 2 ) INFORMATION FOR SEQ ID NO:17:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

TTCTAAGCTT CGTCTCGTGC TGCAGCCC                          28

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

TCTTCGATGT GGGCTCCAAC                                        20

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:19:

ACACACACAC ACATGCATAC                                        20

( 2 ) INFORMATION FOR SEQ ID NO:20:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:20:

GGAGGTGGTG GAGGGAGAGA AAAG                              24

( 2 ) INFORMATION FOR SEQ ID NO:21:

( i ) SEQUENCE CHARACTERISTICS:
        ( A ) LENGTH: 16 base pairs (B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:21:

GGTGGAGGGA GAGAAA    16

(2) INFORMATION FOR SEQ ID NO:22:

(i) SEQUENCE CHARACTERISTICS:
(A) LENGTH: 16 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:22:

GGGGAAGGGA GAAAGA    16

(2) INFORMATION FOR SEQ ID NO:23:

(i) SEQUENCE CHARACTERISTICS:
(A) LENGTH: 16 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:23:

GGGGGAGGGA GAAAGG    16

(2) INFORMATION FOR SEQ ID NO:24:

(i) SEQUENCE CHARACTERISTICS:
(A) LENGTH: 16 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:24:

GGGAGAGGGA GAAGGG    16

(2) INFORMATION FOR SEQ ID NO:25:

(i) SEQUENCE CHARACTERISTICS:
(A) LENGTH: 16 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:25:

GGGAGAGGGA GAGGGA    16

(2) INFORMATION FOR SEQ ID NO:26:

(i) SEQUENCE CHARACTERISTICS:
(A) LENGTH: 16 base pairs
(B) TYPE: nucleic acid
(C) STRANDEDNESS: single
(D) TOPOLOGY: unknown (ii) MOLECULE TYPE: DNA (genomic)

( x i ) SEQUENCE DESCRIPTION: SEQ ID NO:26:

GGCAGAGGGA GAGGGA 16

( 2 ) INFORMATION FOR SEQ ID NO:27:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:27:

GGAGGAGGGA GAGGAA 16

( 2 ) INFORMATION FOR SEQ ID NO:28:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:28:

GGAGCAGGGA GGGCAG 16

( 2 ) INFORMATION FOR SEQ ID NO:29:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:29:

GGACGAGTGA GTTGGA 16

( 2 ) INFORMATION FOR SEQ ID NO:30:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:30:

AGGTGAGGGA GAAGAA 16

( 2 ) INFORMATION FOR SEQ ID NO:31:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:31:

AGGGGAGAGA GATAAT 16

( 2 ) INFORMATION FOR SEQ ID NO:32:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:32:

GGNNGAGGGA GARRRR                                                                 16

( 2 ) INFORMATION FOR SEQ ID NO:33:

( i ) SEQUENCE CHARACTERISTICS:
        ( A ) LENGTH: 7 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:33:

Pro  Lys  Lys  Lys  Arg  Lys  Val
  1                        5

( 2 ) INFORMATION FOR SEQ ID NO:34:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:34:

GGAGGTGGTG GAAAAAGAGA AAAG                                        24

( 2 ) INFORMATION FOR SEQ ID NO:35:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:35:

TGATGAGGGA GAGGGAGAAG GGAT                                        24

( 2 ) INFORMATION FOR SEQ ID NO:36:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:36:

ATCCTTCTC CCTCTCCCTC ATCA                                         24

( 2 ) INFORMATION FOR SEQ ID NO:37:

( i ) SEQUENCE CHARACTERISTICS:
        ( A ) LENGTH: 20 base pairs (B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:37:

TACTGAATTC ACTTAACACT                                        20

(2) INFORMATION FOR SEQ ID NO:38:

(i) SEQUENCE CHARACTERISTICS:
(A) LENGTH: 24 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:38:

CTTTCTCTC CCTCCACCAC CTCC                                    24

(2) INFORMATION FOR SEQ ID NO:39:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:39:

TCTCAAGCTT GGTCCCTCAC                                        20

(2) INFORMATION FOR SEQ ID NO:40:

(i) SEQUENCE CHARACTERISTICS:
(A) LENGTH: 24 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:40:

GGAGATAGTG GAGGGAAAGA AAAG                                   24

(2) INFORMATION FOR SEQ ID NO:41:

(i) SEQUENCE CHARACTERISTICS:
(A) LENGTH: 24 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:41:

GGAGATAGTA GAGGGAGAGA AAAG                                   24

(2) INFORMATION FOR SEQ ID NO:42:

(i) SEQUENCE CHARACTERISTICS:
(A) LENGTH: 14 base pairs
(B) TYPE: nucleic acid
(C) STRANDEDNESS: single
(D) TOPOLOGY: linear (i i) MOLECULE TYPE: DNA ( x i ) SEQUENCE DESCRIPTION: SEQ ID NO:42:

CCCTTCGCCG CCTC 14

( 2 ) INFORMATION FOR SEQ ID NO:43:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:43:

GGAGGTGGTG GAGGGTTTTT TTTT 24

( 2 ) INFORMATION FOR SEQ ID NO:44:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:44:

GGAGGTGGTG GAGGTTTTTT TTTT 24

( 2 ) INFORMATION FOR SEQ ID NO:45:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:45:

GGAGGTGGTG GAGTTTTTTT TTTT 24

( 2 ) INFORMATION FOR SEQ ID NO:46:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:46:

TTTTTTTTG GAGGGTTTTT TTTT 24

( 2 ) INFORMATION FOR SEQ ID NO:47:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:47:

TTTTTGGTG GAGGGTTTTT TTTT 24

( 2 ) INFORMATION FOR SEQ ID NO:48:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:48:

TTTGGTGGTG GAGGGTTTTT TTTT      2 4

( 2 ) INFORMATION FOR SEQ ID NO:49:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:49:

GGGGGGGGGG GGGGGGGGGG GGGG      2 4

( 2 ) INFORMATION FOR SEQ ID NO:50:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:50:

AAAAAAAAAA AAAAAAAAAA AAAA      2 4

( 2 ) INFORMATION FOR SEQ ID NO:51:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:51:

GGAGGCGGAG GCGGAGGCGG AGGC      2 4